US012702822B2

(12) United States Patent
Lu et al.

(10) Patent No.: US 12,702,822 B2

(45) Date of Patent: Aug. 11, 2026

(54) PARA-AORTIC BLOOD PUMP DEVICE

(71) Applicant: 3R Life Sciences Corporation, Campbell, CA (US)

(72) Inventors: Pong-Jeu Lu, Kaohsiung City (TW); Hsiao-Chien Lin, Kaohsiung City (TW)

(73) Assignee: 3R LIFE SCIENCES CORPORATION, Campbell, CA (US)

(*) Notice: Subject to any disclaimer, the term of this patent is extended or adjusted under 35 U.S.C. 154(b) by 1098 days.

(21) Appl. No.: 17/695,344

(22) Filed: Mar. 15, 2022

(65) Prior Publication Data

US 2022/0296877 A1 Sep. 22, 2022

Related U.S. Application Data

(60) Provisional application No. 63/162,098, filed on Mar. 17, 2021, provisional application No. 63/162,086, filed on Mar. 17, 2021.

(51) Int. Cl.

*A61M 60/863* (2021.01)
*A61M 60/165* (2021.01)

(Continued)

(52) U.S. Cl.

CPC ........ *A61M 60/863* (2021.01); *A61M 60/165* (2021.01); *A61M 60/178* (2021.01);

(Continued)

(58) Field of Classification Search

CPC ............ A61M 2205/02; A61M 60/863; A61M 60/585; A61M 60/531; A61M 60/427;

(Continued)

(56) References Cited

U.S. PATENT DOCUMENTS

| | | | | |
|---|---|---|---|---|
| 2012/0138533 A1 | 6/2012 | Curtis et al. | | |
| 2013/0178694 A1* | 7/2013 | Jeffery | ................ | A61M 60/857 600/16 |
| 2019/0282743 A1* | 9/2019 | Agarwal | ............. | A61M 60/237 |

FOREIGN PATENT DOCUMENTS

| | | |
|---|---|---|
| WO | 2007089500 A2 | 8/2007 |
| WO | 2015127965 A1 | 9/2015 |

OTHER PUBLICATIONS

International Searching Report and Written Opinion issued Jun. 6, 2022 in PCT Application No. PCT/US 2022/020403.

* cited by examiner

*Primary Examiner* — William J Levicky
*Assistant Examiner* — Jessandra F Hough
(74) *Attorney, Agent, or Firm* — Anova Law Group, PLLC

(57) ABSTRACT

A para-aortic blood pump device includes a blood pump, an aortic adapter, a driveline, and a driver. The blood pump includes a blood sac, a pump housing and a pressure sensor, whereas the pressure sensor is installed in the pump housing for monitoring the blood pressure inside the blood pump. The aortic adapter is a T-manifold shaped conduit connected to the blood pump and is used for connecting the blood pump with human aorta to facilitate circulatory support. The driveline allows a pneumatic communication to the blood pump in addition to transmitting the electrical blood pressure signal to the driver. The driver receives and processes the electrical blood pressure signal, decides the timing, speed and duration of blood pump fill and eject actions so as to provide counter-pulsatile circulatory support to assist human circulation.

16 Claims, 53 Drawing Sheets

(51) Int. Cl.

| | |
|---|---|
| ***A61M 60/178*** | (2021.01) |
| ***A61M 60/268*** | (2021.01) |
| ***A61M 60/31*** | (2021.01) |
| ***A61M 60/32*** | (2021.01) |
| ***A61M 60/427*** | (2021.01) |
| ***A61M 60/515*** | (2021.01) |
| ***A61M 60/531*** | (2021.01) |
| ***A61M 60/546*** | (2021.01) |
| ***A61M 60/585*** | (2021.01) |
| ***A61M 60/857*** | (2021.01) |
| ***A61M 60/859*** | (2021.01) |
| ***A61M 60/861*** | (2021.01) |
| ***A61M 60/878*** | (2021.01) |

(52) U.S. Cl.
CPC .......... *A61M 60/268* (2021.01); *A61M 60/31* (2021.01); *A61M 60/32* (2021.01); *A61M 60/427* (2021.01); *A61M 60/515* (2021.01); *A61M 60/531* (2021.01); *A61M 60/546* (2021.01); *A61M 60/585* (2021.01); *A61M 60/857* (2021.01); *A61M 60/859* (2021.01); *A61M 60/861* (2021.01); *A61M 60/878* (2021.01); *A61M 2205/02* (2013.01)

(58) Field of Classification Search
CPC .. A61M 60/268; A61M 60/32; A61M 60/859; A61M 60/878; A61M 60/546; A61M 60/178; A61M 60/861; A61M 60/857; A61M 60/515; A61M 60/31
See application file for complete search history.

97
971
973
90
99
92
94
95
EX
98
93

78

SECTION A-A

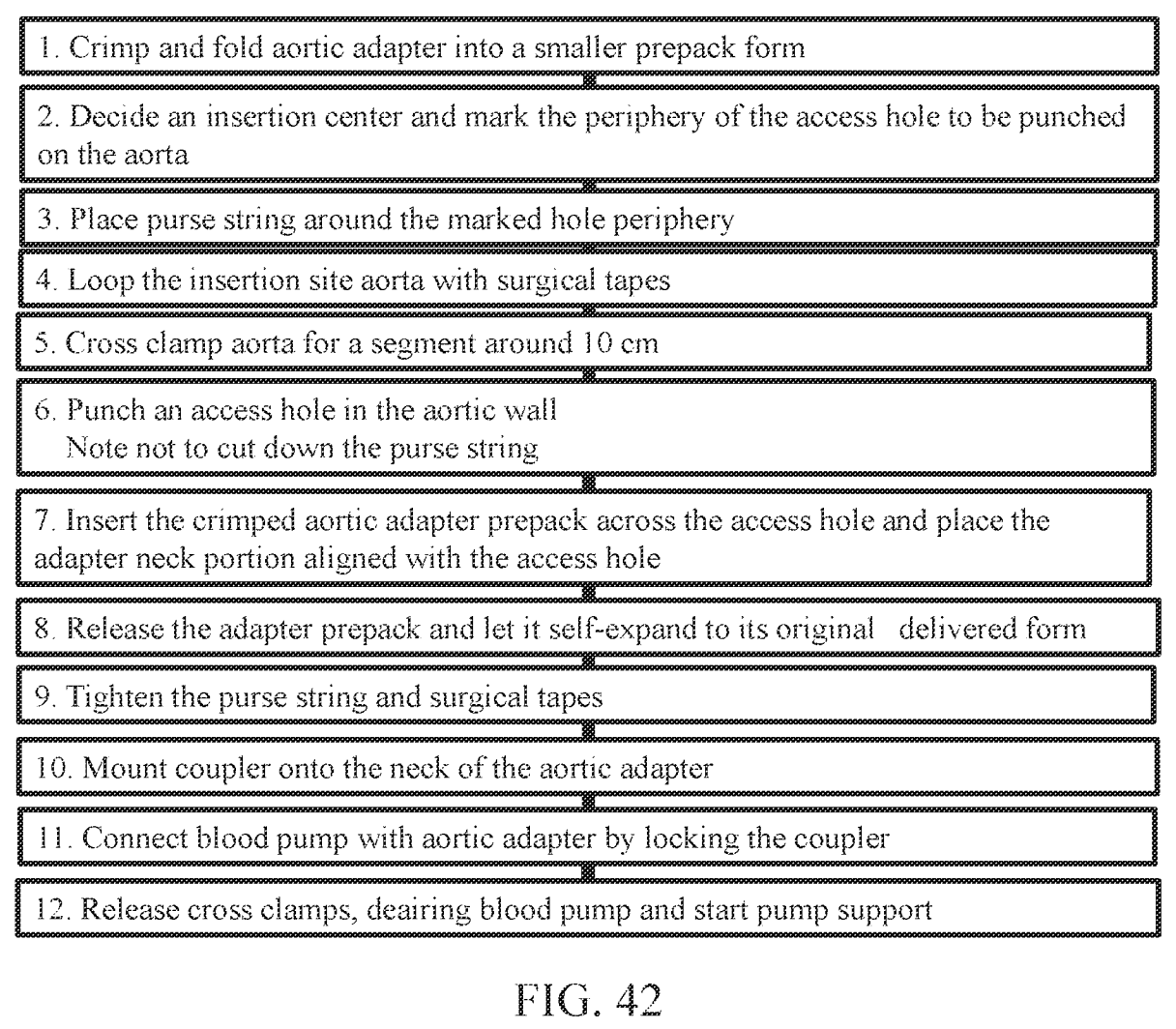

1. Crimp and fold aortic adapter into a smaller prepack form

2. Decide an insertion center and mark the periphery of the access hole to be punched on the aorta 3. Place purse string around the marked hole periphery 4. Loop the insertion site aorta with surgical tapes 5. Cross clamp aorta for a segment around 10 cm 6. Punch an access hole in the aortic wall
Note not to cut down the purse string 7. Insert the crimped aortic adapter prepack across the access hole and place the adapter neck portion aligned with the access hole 8. Release the adapter prepack and let it self-expand to its original delivered form 9. Tighten the purse string and surgical tapes 10. Mount coupler onto the neck of the aortic adapter 11. Connect blood pump with aortic adapter by locking the coupler 12. Release cross clamps, deairing blood pump and start pump support

FIG. 42

PARA-AORTIC BLOOD PUMP DEVICE

CROSS REFERENCE TO RELATED APPLICATIONS

This application claims the benefit of U.S. Provisional Application No. 63/162,086 and No. 63/162,098 filed on Mar. 17, 2021, the entirety of which is incorporated by reference herein.

BACKGROUND OF INVENTION

Field of the Invention

The present invention relates to a ventricular assist device (VAD), in particular to a left ventricular assist device (LVAD) based on the principle of counterpulsation support.

Description of the Related Art

Mechanical Circulatory Support in Heart Failure Treatment

The disease progression of heart failure is characterized by a vicious cycle. Medical therapy for early-to-moderate stage heart failure is to suppress the neurohormonal compensatory mechanism, which slows down rather than remedies the death spiral of the heart failure viscous cycle. Heart transplant or ventricular assist device (VAD) implantation is intended to be used for the terminal-stage heart failure. There exists an "unmet need" gap region between the medically ineffective and transplant/VAD treatments along the course of heart failure progression. As heart failure deteriorates beyond effective medical treatment stage, often, patients cannot receive any therapy but waiting for heart failure to deteriorate further into the refractory stage where transplant/VAD can be considered. This treatment gap is categorized as Interagency Registry for Mechanical Assisted Circulatory Support (INTERMACS) profiles 4-7, and patients in this class of heart failure typically show symptoms of apnea, pulmonary hypertension, renal hypoperfusion and exercise intolerance with elevated inflammatory responses.

The best policy for treating heart failure by mechanical circulatory support (MCS) is to implant a left ventricular assist device (LVAD) in time before a failing heart becomes refractory. However, this policy is not practically realizable because the current rotary pumps, or continuous-flow LVADs, are invasive in implantation and involve with considerable post-operative morbidity rates, making the LVADs only indicated for terminal-stage heart failure patients.

Counter-pulsatile support therapeutics has been clinically proven effective for more than fifty years by the bedside intra-aortic balloon pump (IABP) administration. The recent success in extending IABP use from bedside to ambulatory support, via implanting the balloon pump from axillary or subclavian artery, has achieved bridging patients to heart transplant. Balloon counterpulsation together with patient ambulation showed surprisingly good benefit in improving the heart functional status. Nevertheless, this balloon delivery site improvement is only a temporary solution. Patients treated by ambulatory IABP are still bounded in hospital and the axillary or subclavian insertion cannot be used safely in a long-term period.

Currently, there exist no clinically approved partial-support (blood pump providing 2-3 Liter per minute pump flow), early intervention devices that are specifically indicated for less-sick advanced heart failure patients. A great portion of such less-sick heart failure patients will deteriorate and develop acute myocardial ischemia or cardiogenic shock requiring emergent mechanical circulatory support. The life-sustaining, acute circulatory support systems such as IABP, extracorporeal membrane oxygenation (ECMO), and percutaneous micro-axial catheter pumps could be emergently administered, however, the mortality rate of the supported patients is generally high in the range of 40-70%. Moreover, it is often difficult for patients, families, and clinicians to decide if invasive and expensive rotary pumps should be used after the exhaustion of the acute circulatory support devices. Therefore, it is a main subject for related manufacturers to overcome the therapeutic gap in heart failure treatment, by innovating new long-term implantable VAD design that encompasses the early intervention and less traumatic surgery concept.

Early Intervention Partial-Support LVAD

An early intervention partial-support blood pump, also known as a para-aortic blood pump device, was presently invented according to the counterpulsation support principle. The para-aortic blood pump device of the present invention provides a counter-pulsatile circulatory support including augmentation of systemic blood flow during diastole (heart relaxation) to improve myocardial and organ perfusion while reducing left ventricular workload during systole (heart contraction). For mechanical circulatory support device recipients, earlier hemodynamic support and post-operative ambulatory ability is important for survival and disease improvement. Less invasive surgery, a premise of early intervention, hence, constitutes another critical element aside from the hemodynamic therapeutics the partial-support LVADs can provide. With the aid of specially designed surgical tools, the para-aortic blood pump device of the present invention can be safely implanted via a less traumatic surgical procedure (such as a beating-heart mini-left thoracotomy). Evidences gathered from several contemporary clinical trials performed for late-stage heart failure patients have shown that chronic LVAD-supported heart, either by displacement type blood pump or by rotary pump, can encourage the nonischemic myocardium undergo cellular reverse remodeling, resulting in a significant portion of device-treated patients gaining robust myocardial recovery or remission. This finding implies that if early ambulatory support feature can be included in LVAD design and instituted in treating heart failure, the mechanical unloading would be potentially more effective and beneficial for salvaging the less-sick (INTERMACS profiles 4-7) patients.

It is plausible and beneficial that before heart transplant or implanting highly invasive rotary pumps, patients can be treated by the less traumatic para-aortic blood pump device for an extended period. Some patients may recover with the circulatory assistance offered by the para-aortic blood pump device, executed via therapeutic counterpulsation for months or longer (1-2 years) in the form of ambulatory support. For those hemodynamically stabilized but non-recoverable recipients, the para-aortic blood pump device can be used in a long-term manner as a destination therapy device or as a bridging to transplant. The para-aortic blood pump device, hence, can serve as an interim salvage modality before heart transplant or an expensive and invasive rotary pump implantation. The role of the para-aortic blood pump device in heart failure treatment is multi-faceted, it can be used as a means for bridge-to-recovery (or remission), bridge-to-decision (rotary pump), bridge-to-transplant, or alternative-to-transplant (destination therapy).

BRIEF SUMMARY OF INVENTION

It is one of primary objectives of the present invention to overcome the shortcomings of the prior art by disclosing a para-aortic blood pump device comprising: a blood pump, an aortic adapter, a driveline, and a driver. The blood pump comprises a pump housing, a blood sac, and a pressure sensor, and the pressure sensor is installed in the pump housing of the blood pump for monitoring blood pressure inside the blood pump. The sensed blood pressure is transduced into an electrical signal to be transmitted through a driveline into a driver. The aortic adapter is a T-manifold shaped flow conduit coupled to the blood pump and used for integrating the blood pump with the human aorta. The aortic adapter is thin-walled and may have structural reinforcement embedded for strength enhancement. The driveline is coupled to the housing of the blood pump, providing a pneumatic communication to the blood pump and transmitting the electrical blood pressure signal received from the pressure sensor. The driver is coupled to the driveline for receiving the electrical blood pressure signal. The driver comprises an electro-mechanical actuator commanded by a controller in the driver to generate counter-pulsatile pneumatic pressure pulse according to the sensed electrical blood pressure signal. The pressure pulse is sent to and from the blood pump through the driveline, fulfilling the ejection and filling action of the blood pump when supporting the human circulation.

In some embodiments, the driver further comprises a driveline controller and a vibrator, and the driveline controller is used for processing the electrical blood pressure signal, and the vibrator is used for providing an audible alarm or a tactile feedback.

In some embodiments, the driveline and a part of the driver are substituted by a distal driveline, a driveline interconnector and a proximal driveline, and the distal driveline is provided for transmitting the electrical blood pressure signal and the pressure pulse to the blood pump, and the driveline interconnector comprises a driveline controller and a vibrator, and the driveline controller is used for processing the electrical blood pressure signal, and the vibrator is used for providing an audible alarm or a tactile feedback.

In some embodiments, the blood pump and the aortic adapter are integrally formed.

In some embodiments, the para-aortic blood pump device comprises a coupler, and the coupler includes a coupling adapter installed at a neck of the aortic adapter for coupling the blood pump to the aortic adapter.

In some embodiments, two gradually flared ends of the aortic adapter constitute a smooth transition of an elastic property, being progressively softer in proportion to a wall thickness toward the end.

In some embodiments, the pump housing of the blood pump is installed with the blood sac therein, and the blood sac is an oval-shaped membrane body of revolution to a centerline of the blood pump, at two ends there are two polymeric stems that are bonded with the membrane body, working as a flexing/stretching relief mechanism to alleviate stress concentration when attached onto the pump housing of the blood pump.

In some embodiments, the pump housing of the blood pump has an opening, and the opening continuously integrates with the aortic adapter that provides a smooth interface with a neck of the aortic adapter.

In some embodiments, the electro-mechanical actuator comprises a pressure equalization valve connected to an air chamber, and the pressure equalization valve is opened periodically so that an air pressure in the air chamber can be set to be in equilibrium with atmospheric pressure.

In some embodiments, the para-aortic blood pump device provides a counter-pulsatile augmentation of systemic blood flow during diastole (heart relaxation) to improve myocardial and organ perfusion while reducing left ventricular workload during systole (heart contraction).

In some embodiments, the driver further comprises a trigger-detection micro controller unit, and the electrical blood pressure signal provides the sensed pressure waveform within the blood pump for the trigger-detection micro controller unit to compute and determine the eject and fill timings for the electro-mechanical actuator.

In some embodiments, the electro-mechanical actuator comprises a motor and ball screw/nut unit that drives a reciprocating piston within a cylinder of electro-mechanical actuator; the movement of the piston pushes and withdraws air via the driveline coupled to the blood pump.

In some embodiments, wherein the electro-mechanical actuator is a pneumatic actuator includes: a brushless servo motor and a ball screw piston/cylinder assembly, wherein atmospheric air is used as a driving medium to reciprocally eject/fill the blood pump; and a pressure equalization valve is equipped on the electro-mechanical actuator to solve the problems of air leakage at a piston ring and condensation of vapor permeated out from a blood sac membrane.

In some embodiments, the driver receives the electrical blood pressure signal and processes the electrical blood pressure signal using trigger detection algorithm to generate a trigger signal that commands a driver actuation in synchronization with heart rhythm.

In some embodiments, upon receiving the assigned trigger timing, the micro controller unit sends commands to a motor controller to drive a piston of the electro-mechanical actuator, from eject-to-fill or from fill-to-eject positions, to provide counter-pulsatile circulatory support including contraction unloading during the cardiac systolic phase and perfusion augmentation during the cardiac diastolic phase, respectively.

In some embodiments, the driver further comprises a user interface, and the user interface comprises an indicator, an audio alarm, a button and a liquid crystal display (LCD).

In some embodiments, when the micro controller unit loses the electrical blood pressure signal from the blood pump, a washout mode is launched automatically by the micro controller unit to drive the electro-mechanical actuator, operating at a predetermined pumping rate and driver stroke volume.

In some embodiments, the washout mode is used to prevent the formation of thrombus in the blood pump, which is a device protection mode instead of providing circulatory support.

In some embodiments, the blood sac is anchored via a proximal stem to a proximal shell of the pump housing and via a distal stem to a distal shell of the pump housing.

BRIEF DESCRIPTION OF THE DRAWINGS

FIG. 42 describes the step-by-step instruction of implanting the aortic adapter into a targeted aortic segment and the connection with a blood pump.

DESCRIPTION OF THE PREFERRED EMBODIMENTS

There are four embodiments that can be employed to realize the present para-aortic blood pump invention, as described below.

Figure 1:
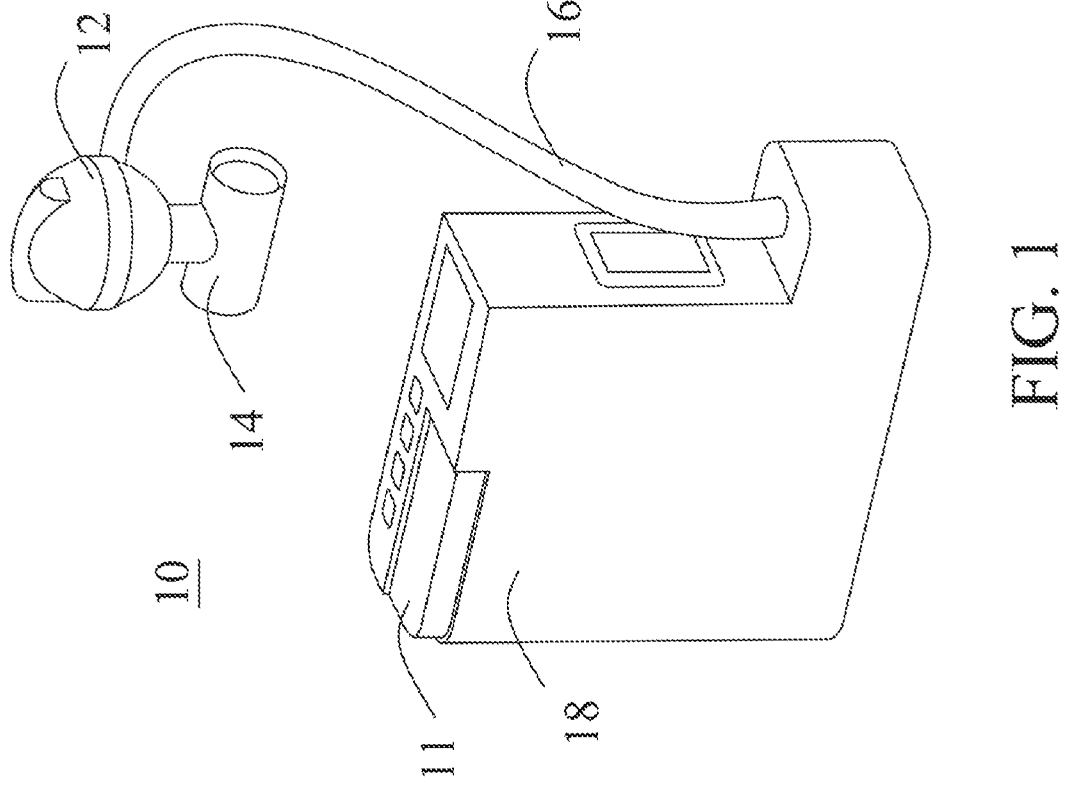
FIG. 1 is a schematic view of a para-aortic blood pump device in accordance with a first embodiment of the present invention.

With reference to FIG. 1 for the schematic view of a para-aortic blood pump device in accordance with the first embodiment of the present invention, the para-aortic blood pump device 10 comprises: a blood pump 12, an aortic adapter 14, a driveline 16 and a driver 18. The blood pump 12 further comprises a pump housing and a pressure sensor. The blood pump housing consists of two chambers, one for blood storage and another to receive driving air. These two chambers are separated by an oval-shaped flexible membrane suspended via a pair of stress-relief stems attached to the pump housing. The pressure sensor is installed in the pump housing for monitoring blood pressure inside the blood pump 12 to generate electrical blood pressure signal. The aortic adapter 14 is a valveless, T-manifold shaped flow communicator coupled with the blood pump 12 and human aorta. In the first embodiment, the aortic adapter 14 and the blood pump 12 are integrally formed, having a seamless blood contacting surface, and the aortic adapter 14 is provided for connecting the blood pump 12 with the human aorta. The aortic adapter 14 is made of flexible materials, allowing the aortic adapter 14 be deformed during insertion delivery from a hole made on the aortic wall. This aortic adapter conduit, after inserted, is self-expandable and strong enough to withhold the radial compression exerted from oversized fitting to the contacted aortic lumen. The driveline 16 is coupled to the pump housing of the blood pump 12 for providing a pressure pulse to the blood pump 12 and transmitting the electrical blood pressure signal received from the pressure sensor. The driver 18 is coupled to the driveline 16 for receiving the sensed electrical blood pressure signal, and the driver 18 comprises an electro-mechanical actuator to generate a pressure pulse according to the electrical blood pressure signal and provides a regulated pressure pulse to the blood pump 12 through the driveline 16. The wearable driver 18 provides timed air pressure pulses in synchronization to cardiac rhythm to drive and control the eject and fill of the implanted blood pump 12.

The driver 18 comprises a battery power system 11 and a redundant battery power system (the battery power systems 21, 31, 41 in the FIGS. 2-4, and 8 are the same or similar), wherein the redundant battery power system ensures a continuous power supply of the driver 18. Power can also be supplied to the driver 18 by an AC adapter for the convenience of the device recipient when mobility is not required. Further, a clinical monitor unit, not shown in FIGS. 2-4, can be connected to the driver 18 to provide a user interface to the clinician for displaying device monitoring or diagnostic information and for accessing to driver parameters in order to initiate and optimize a patient-specific operational mode setting.

Figure 2:
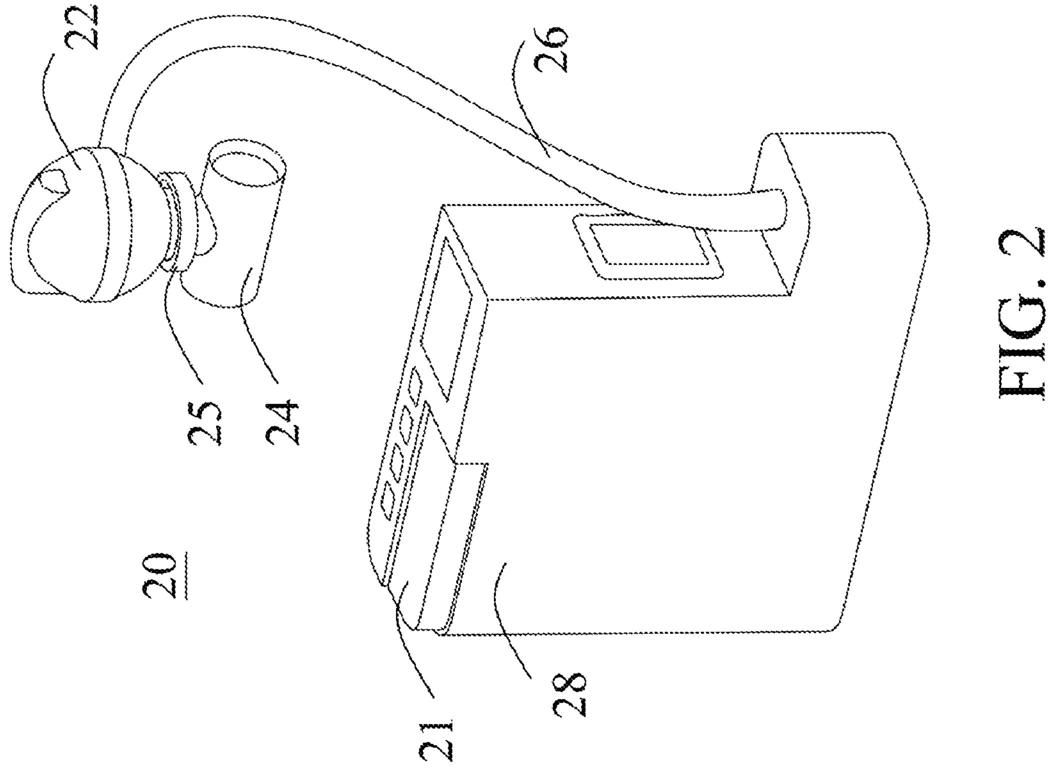
FIG. 2 is a schematic view of a para-aortic blood pump device in accordance with a second embodiment of the present invention.

In FIGS. 1 and 2 illustrated two different blood pump 12, 22 designs coupled with the same driveline 16, 26 and driver 18, 28 system. FIG. 2 is the schematic view of a para-aortic blood pump device 20 in accordance with the second embodiment of the present invention, and the difference between the second embodiment and the first embodiment of the present invention resides on that the para-aortic blood pump device 20 of the second embodiment further comprises a coupler (or coupling adapter) 25. The blood pump 22 and the aortic adapter 24 of the second embodiment are not integrally formed, but are detachable from each other; and the coupler 25 is provided for coupling the blood pump 22 to the aortic adapter 24. Care must be exercised in the coupler design to minimize the interface discontinuity around the connected region. During device implantation, the aortic adapter 24 is first inserted into the aorta via an access hole made in the aortic wall. Using specially developed implantation tools, a coupling adapter 25 is disposed around the protruded neck of the aortic adapter 24, to which the blood pump 22 can be connected. Following the introduction of the blood pump 22 into the thoracic cavity, the blood pump 22 and the aortic adapter 24 are firmly integrated using the coupler 25. Such detachable blood pump 22 and aortic adapter 24 design encompasses surgical and post-operative advantages. During device implantation, the detachable pump design renders the aortic adapter insertion easier because the surgical field is clearer without the interference of the pump body. Further, in the post-operative period, blood pump can be detached and exchanged in case of pressure sensor malfunction or blood sac rupture requiring emergent surgical replacement. The detachable blood pump design of the second embodiment is advantageous in this regard. The aortic adapter can stay in the aorta without explantation, avoiding troublesome and risky redo surgery associated with aortic adapter removal.

Figure 3:
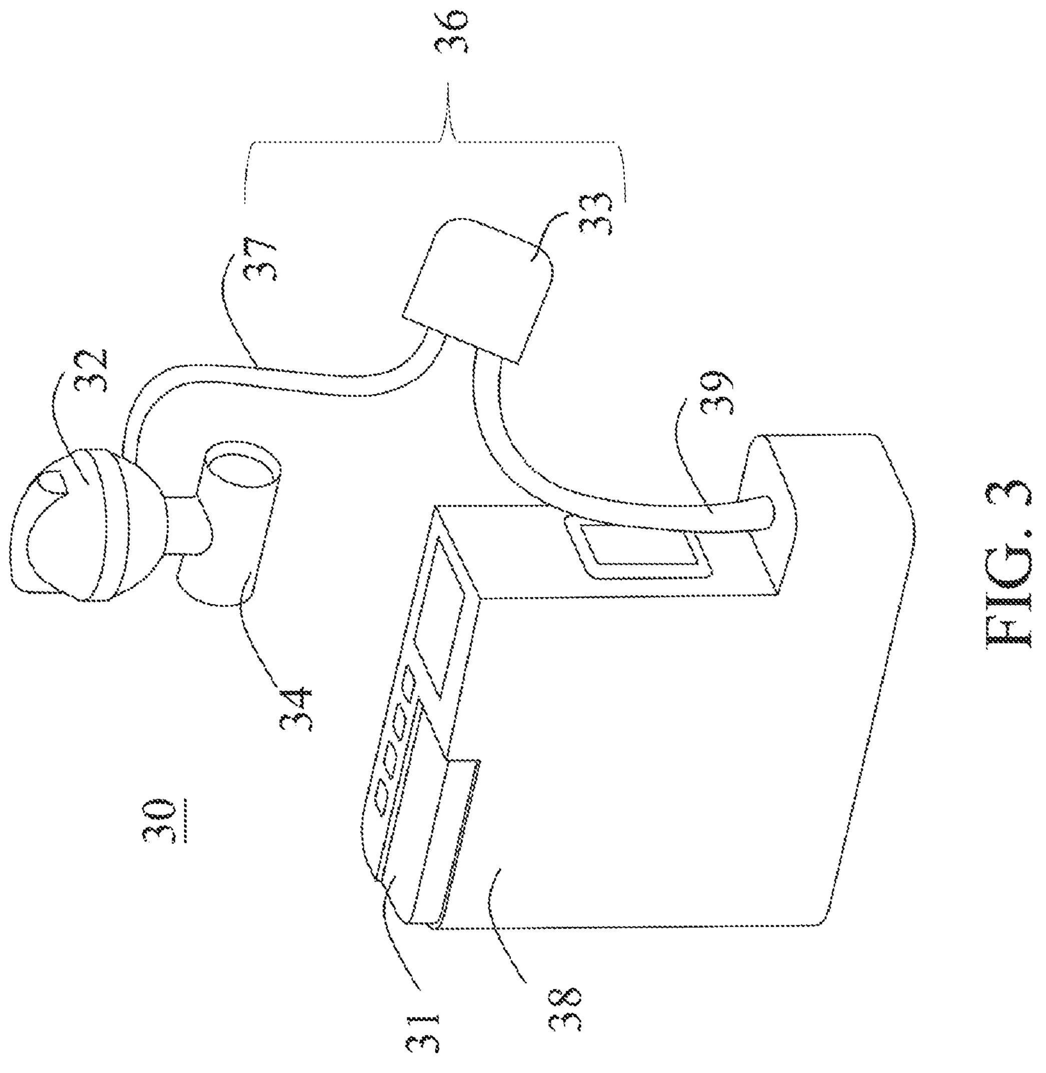
FIG. 3 is a schematic view of a para-aortic blood pump device in accordance with a third embodiment of the present invention.

With reference to FIGS. 1 and 3 for the schematic views of the para-aortic blood pump devices 10, 30 in accordance with the first and the third embodiment of the present invention respectively, the difference between the third embodiment and the first embodiment of the present invention resides on that the driveline 16 of the first embodiment are substituted by the driveline 36 including the distal driveline 37, the driveline interconnector 33 and the proximal driveline 39 of the third embodiment. The distal driveline 37 is coupled to the driveline interconnector 33 for transmitting the electrical blood pressure signal acquired from the pressure sensor and the pressure pulse sent from the driver 38; and the driveline controller and the vibrator (for alarm warning purpose) included in the driveline interconnector 33 are originally included in the driver 18 of the first embodiment, so that the driver 18 of the first embodiment has the additional driveline controller and vibrator (compared with the driver 38 of the third embodiment). The driveline controller is used for processing the electrical blood pressure signal, and the vibrator is used for providing an audible alarm or a tactile feedback. In other words, the mechanical power transmission to fill and eject the blood pump and the analog/digital signal conversion and alarm annunciation, achieved respectively by the driveline 16 and the driver 18 of the first embodiment, are substantially the same as those by the distal driveline 37, the driveline interconnector 33 and the proximal driveline 39 of the third embodiment.

The first embodiment has a cleaner driveline configuration and disposes electronic signal processor in the driver, hence minimizing the risk of environmental contamination (water ingress or moisture condensation) of the sensed pressure signal and the air leak incurred at the joint, both associated with the driveline interconnector 33. Nevertheless, this long driveline is more vulnerable to contact damage such as wear, kink, cut, abrasion arising from the contact with foreign objects in daily activities. Any major damage to the driveline 16 of the first or second embodiment, either electronically or mechanically, may warrant surgical blood pump replacement that is highly undesirable in view of surgical redo risk and the associated medical costs. The third or fourth embodiment, by employing a mid-way connector (driveline interconnector), mitigates such driveline damage-related blood pump replacement drawback. In general, the length of externalized distal driveline 37 is short and the interconnector 33 is protected better by the coverage of the skin dressing and/or the patient vest. In the extreme case of severe damage of the driveline beyond repairable, the most possibly damaged proximal driveline 39 can be easily exchanged without resorting to surgery. In addition, the third or fourth embodiment is more immune to electromagnetic interference because the analog-to-digital signal conversion is already accomplished in the circuitry in the interconnector 33. The fidelity of pressure signals can be better assured in the third or fourth embodiment because digital signal transmission in the proximal driveline 39 is less susceptible to the electromagnetic interferences.

Figure 4:
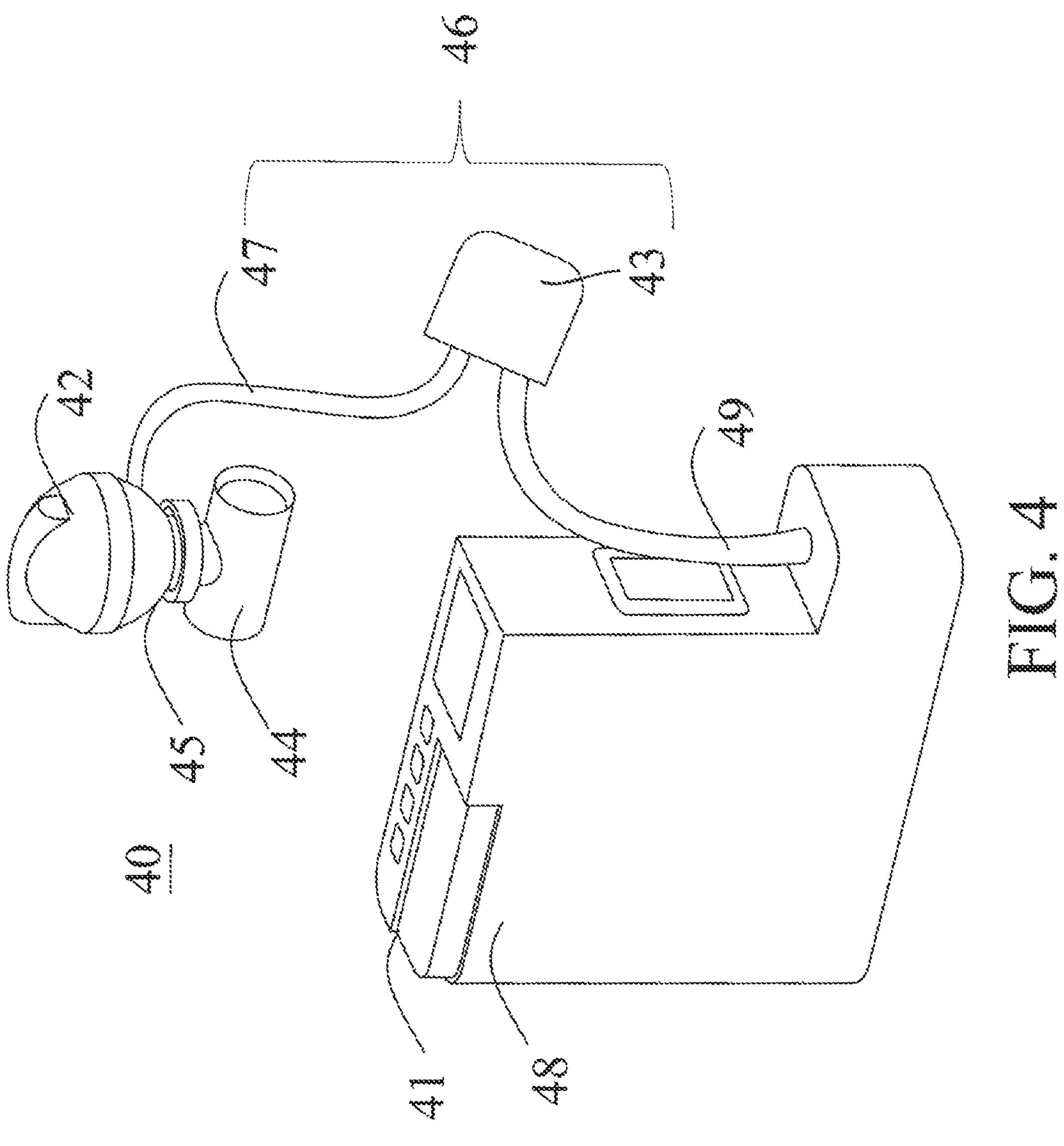
FIG. 4 is a schematic view of a para-aortic blood pump device in accordance with a fourth embodiment of the present invention.

With reference to FIGS. 3 and 4 for the schematic views of the para-aortic blood pump device 30, 40 in accordance with the third and the fourth embodiment of the present invention respectively, the difference between the third embodiment and the fourth embodiment resides on that the aortic adapter 34 and the blood pump 32 of the third embodiment are integrally formed; whereas the blood pump 42 and the aortic adapter 44 of the fourth embodiment are detachable; and the fourth embodiment further comprises a blood pump 42, an aortic adapter 44 and a coupler 45 which are the same as the blood pump 22, the aortic adapter 24, and the coupler 25 of the second embodiment, and thus their descriptions will not be repeated. The driveline 46 including the distal driveline 47, the driveline interconnector 43 and the proximal driveline 49 of the fourth embodiment is the same as the driveline 36 including the distal driveline 37, the driveline interconnector 33 and the proximal driveline 39 of the third embodiment.

Figure 5:
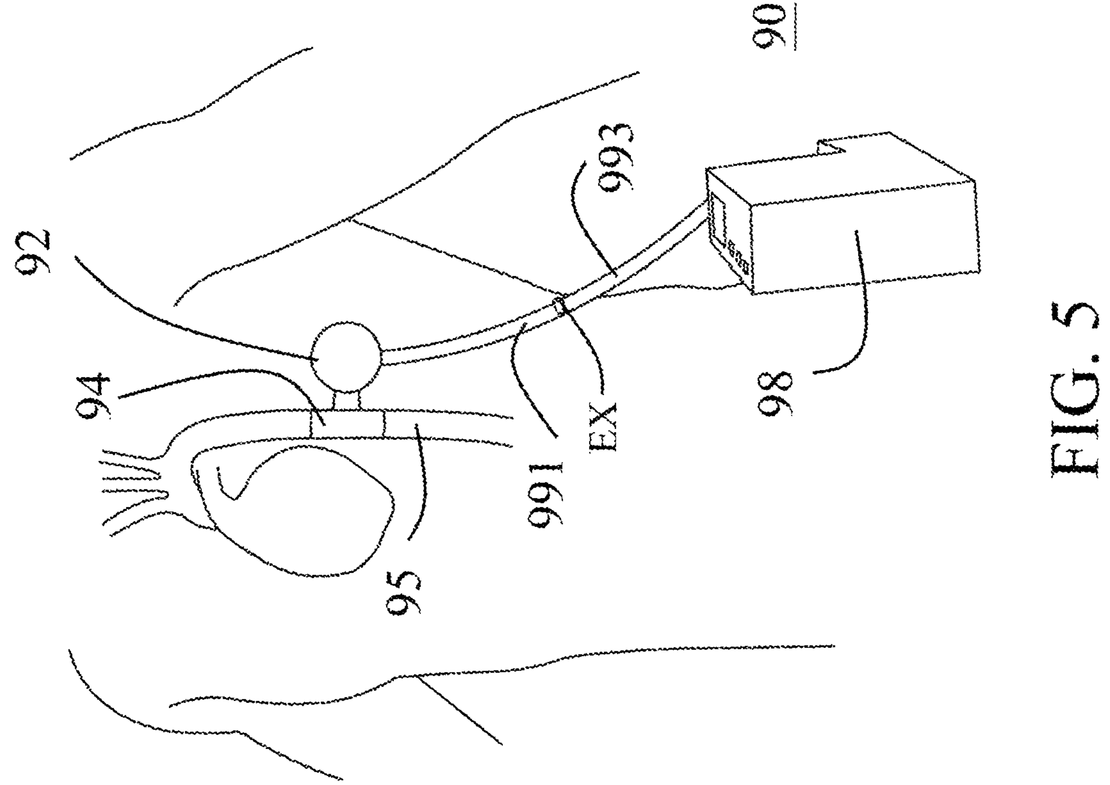
FIG. 5 is a schematic view of a para-aortic blood pump device installed in human body in accordance with the first and second embodiments of the present invention.

With reference to FIG. 5 for the schematic view of a para-aortic blood pump device installed in human body in accordance with an exemplary embodiment of the present invention, the para-aortic blood pump device 90 comprises a blood pump 92, an aortic adapter 94, an internal driveline 991, an external driveline 993, and a driver 98. In another embodiment, the para-aortic blood pump device further comprises a coupler. The part of the para-aortic blood pump device 90 implanted into the human body includes the blood pump 92, the aortic adapter 94 and the internal driveline 991. In another embodiment, the para-aortic blood pump further comprises a coupler. After a surgical operation, the aortic adapter 94 is installed into an aorta 95, and an exit site EX is created at an appropriate position of an epidermis of the human body. The part of the para-aortic blood pump device 90 situated outside the human body includes the external driveline 993, and the driver 98. The exit site EX is used as a boundary, and the internal driveline 991 has a segment covered by a fabric velour for tissue ingrowth to attain infection control. The implanted velour portion is placed 2-5 cm subcutaneously from the exit site EX. The driver 98 is a wearable or portable device.

Figure 6:
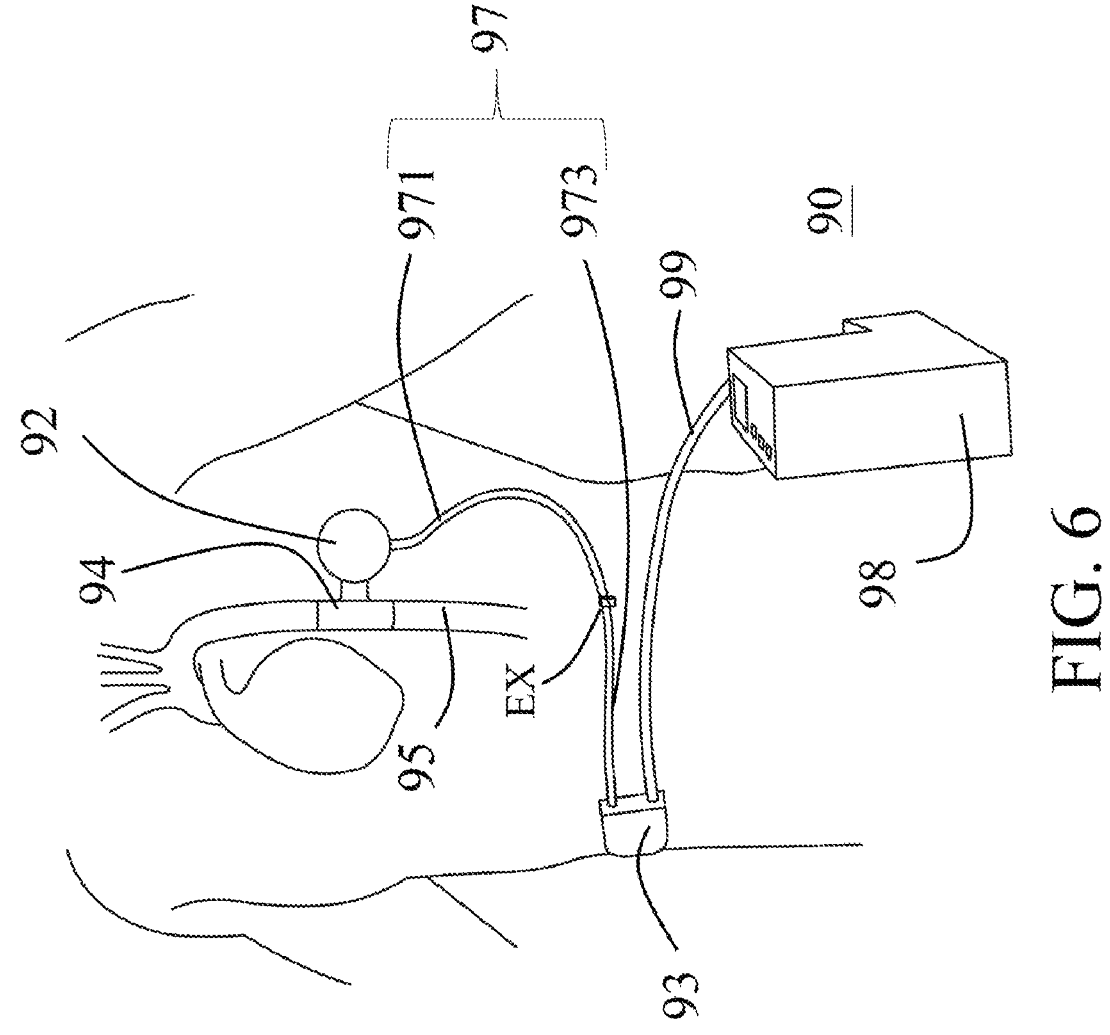
FIG. 6 is a schematic view of a para-aortic blood pump device installed in human body in accordance with the third and fourth embodiments of the present invention.

With reference to FIG. 6 for the schematic view of a para-aortic blood pump device installed to human body in accordance with an exemplary embodiment of the present invention, the para-aortic blood pump device 90 comprises a blood pump 92, an aortic adapter 94, a distal driveline 97 (including an internal distal driveline 971, an external distal driveline 973 outside the human body), a driveline interconnector 93, a proximal driveline 99 and a driver 98. In another embodiment, the para-aortic blood pump device 90 further comprises a coupler. The part of the para-aortic blood pump device 90 implanted into the human body includes the blood pump 92, the aortic adapter 94 and the internal distal driveline 971. In another embodiment, the para-aortic blood pump device further comprises a coupler. After a surgical operation, the aortic adapter 94 is installed into an aorta 95, and an exit site EX is created at an appropriate position of an epidermis of the human body. The part of the para-aortic blood pump device 90 situated outside the human body includes an external distal driveline 973, a driveline interconnector 93, a proximal driveline 99 and a driver 98. The exit site EX is used as a boundary, and the distal driveline is divided into an internal distal driveline 971, covered with velour for infection control, and an external distal driveline 973. The driver 98 is a wearable or portable device.

The implant subsystem is described further below.

Implantation is achieved through a relatively small thoracic opening by using less invasive surgical techniques via a left thoracotomy. A thoracic incision is made, for example, at the 7th intercostal space as the primary opening to allow placement of the aortic adapter and the blood pump. Two other small incisions are made at the 6th and 8th intercostal spaces, respectively, to introduce proximal and distal aortic cross clamps. The cross-clamped segment of aorta allows aortic adapter be inserted into the implant site through an excess hole made in the aortic wall. The aortic adapter is flexible and is able to be crimped and constrained into a smaller delivery configuration prior to insertion. Upon completion of delivery into aorta, the crimped aortic adapter shall be released and restore back to its original form with predetermined oversize to the implant site lumen diameter. The material of the aortic adapter hence is important, which shall be flexible but possessing sufficient radial strength to make the delivered adapter conduit remain circular without wall buckling. Candidate aortic adapter construct may include that made by silicone or polyurethane elastomers, or those polymeric constructs reinforced with embedment.

The functional requirements of the aortic adapter of each of the aforementioned embodiments is further described below.

Hemodynamically, the aortic adapter plays a role of flow communication between the blood pump and human systemic circulation. Besides this role, the aortic adapter also serves as a mechanical base to hold the blood pump in place when connected to the aortic adapter. The structure of the aortic adapter has to be elastic but kink resistant, and strong enough to withstand the internal blood pressure and the external contact forces, exerted via contact with the surrounding lung tissue or diaphragm associated with respiratory and thoracic movement.

Figure 7:
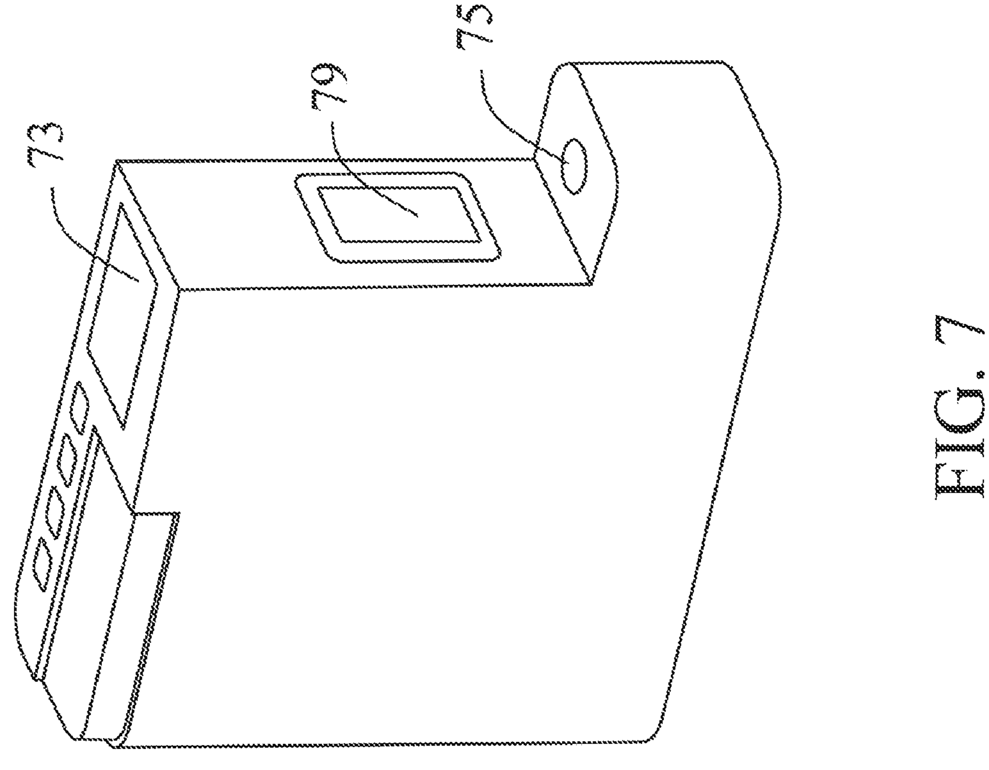
FIG. 7 is a first schematic view of a driver in accordance with an exemplary embodiment of the present invention.
Figure 8:
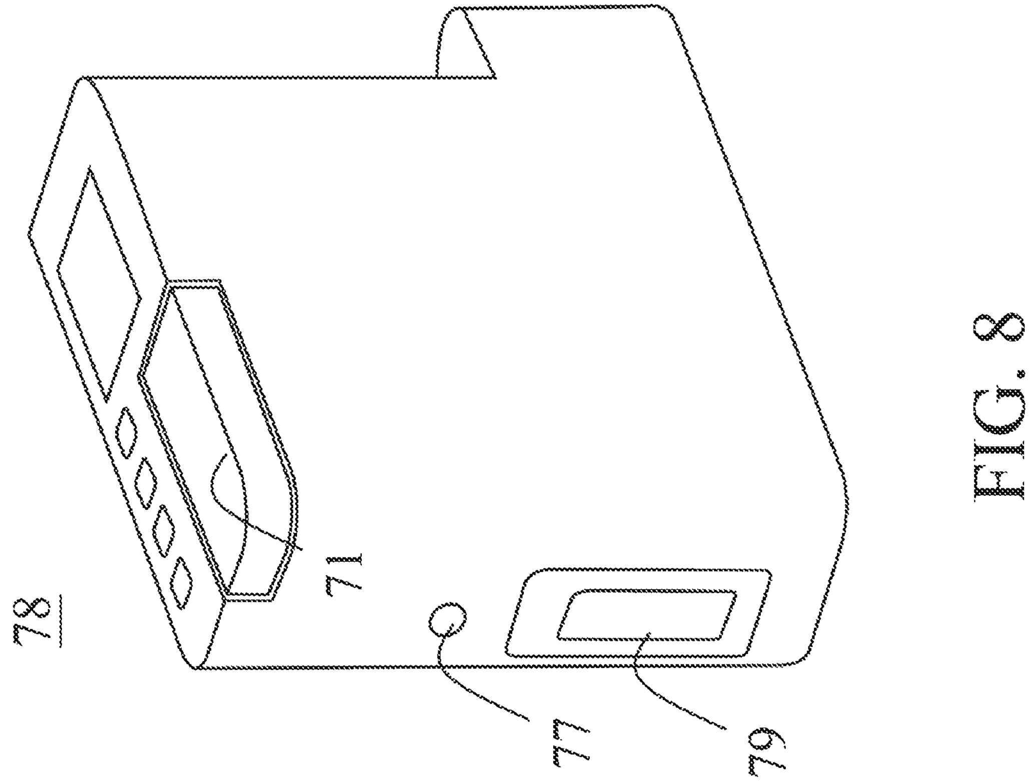
FIG. 8 is a second schematic view of a driver in accordance with an exemplary embodiment of the present invention.

The aortic adapter 54 is implanted inside the aorta with its two conduit ends 545, 645 interfaced with the aortic lumen forming a host/graft boundary in the blood stream (see FIGS. 7B and 8B). In order to minimize the host/graft interface discontinuity, both morphologically and elastically, the two conduit ends 545, 645 are configured to have a gradually flared inner surface profile and a continuously reduced wall thickness distribution. Such a conduit end design minimizes the step at the interface as well as constitutes a compliance-matching effect for joining the aortic adapter with the aortic lumen. Thrombus at the interface can thus be annihilated because the rate of interface clot aggregation is slower than the natural thrombolysis rate provided by the endothelium. In addition, the gradually thinning conduit wall structure renders the conduit ends 545, 645 softer (compliant) which enables the ends expand and contract in concert with the pulsatile blood pressure, constituting a dynamic seal effect to prevent blood from being jammed into the gap of the joint interface which often is the origin of thrombus formation.

The driver of each of the aforementioned embodiments is further described below.

Figure 9:
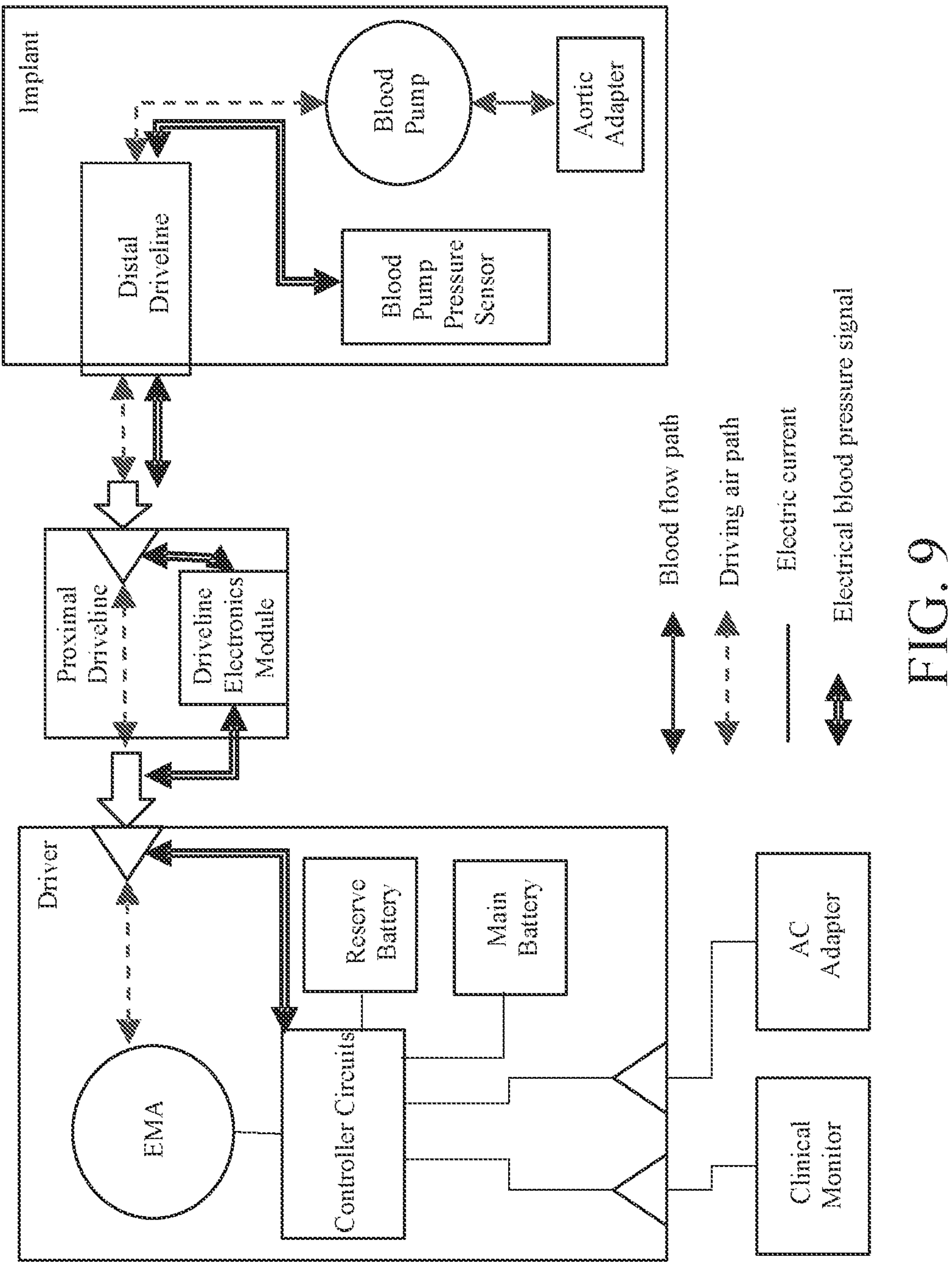
FIG. 9 is a block diagram of the driver functions and the key interconnecting signals that are necessary for the operation of the present invention.
Figure 10:
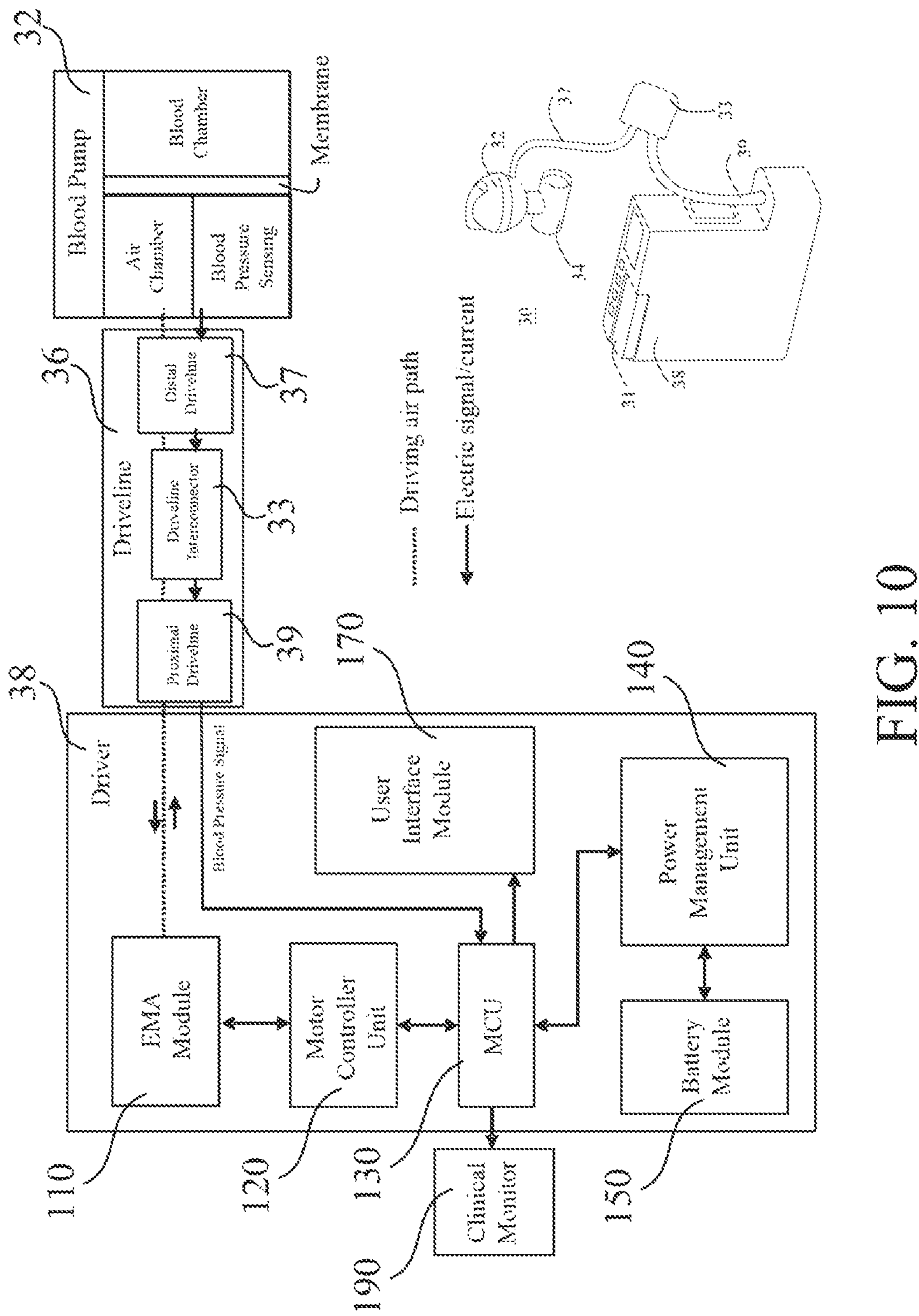
FIG. 10 is a block diagram of the driver functions and the key interconnecting signals that are necessary for the operation of the third embodiment of the present invention.

Illustrated in FIG. 9 and FIG. 10 are the right-side and left-side perspective views of the driver 78. This compact driver 78 contains internal modules including an electromechanical actuator (EMA), an electronic controller, a pair of main battery and reserve battery. This driver 78 also comprises external modules of a user interface panel 73, a battery access door 71, a driveline receptacle 75, an AC receptacle 77, and a pair of ventilation windows 79, as depicted in FIGS. 9 and 10.

Critical information in operation and alarm warning of device malfunction and aortic pressure conditions will be displayed on the user interface panel 73 of the driver 78. The primary battery can be exchanged through the battery access door 71 when primary battery power is exhausted. An electric cable is used to power the driver 78 via a connection through the AC receptacle 77 when patient is bedridden and power from wall outlet can be utilized in a long-term manner. The proximal driveline 99, 993 end is connected to the driver 78 through the driveline receptacle 75, through which both electric sensor signal and pneumatic pressure pulse are communicated. A pair of ventilation windows 79 are installed on the opposite sides of the driver 78 to allow ambient air to flow through the interior of the driver 78 for cooling purpose.

The driver 78 can be coupled externally to a clinical monitor, wherein the clinical monitor is provided for collecting and displaying real-time clinical waveform data and stores patient data for long-term condition monitoring and diagnosis. Further, a clinical monitor unit provides a user interface to the clinician for displaying device monitoring/diagnostic information and for accessing to driver parameter settings in order to initiate and optimize a patient-specific operational mode.

The EMA is a pneumatic actuator consisting of a brushless servo motor, a ball screw unit, a piston and a cylinder assembly. Atmospheric air is used as a driving medium to reciprocally eject and fill the blood pump.

The EMA module is housed within the driver carried by the implant recipient. The EMA consists of a brushless servo motor, a piston and cylinder assembly and a ball screw unit which comprises a ball screw rod and a nut. The piston is firmly mounted on top of the ball screw rod which is in rotational coupling with the nut of the ball screw unit. The servo motor includes a stator and a rotor and the rotor is integrated with the nut of the ball screw unit. Through the electromagnetic coupling of the rotor/stator induction, the rotor can be rotated in both clockwise and counter-clockwise directions, thereby driving the ball screw rod back-and-forth in a rectilinear manner to result in a reciprocating piston stroke motion in a cylinder. The stroke motion of the piston drives air to and from the implanted blood pump via a driveline connecting the blood pump and the cylinder.

There are two air driving problems associated with the present EMA pneumatic actuator design; namely, the air leak and the condensation of water vapor permeated from the blood through the blood sac wall. The former will impair the pump eject and fill function and driver power consumption leading to degradation of support effectiveness, and the latter will cause bacteria invasion risk to the driveline interior. To solve these two problems, the present EMA incorporates a pressure equalization valve installed in the cylinder chamber wall for air replenishment and moisture reduction. The pressure equalization valve is opened periodically at a predetermined frequency, allowing air mass transport between the cylinder and the ambient until the air pressure in the cylinder chamber equals the atmospheric pressure. The EMA incorporates position and optical sensors to acquire reference trajectory signals for the electronic controller to generate coordinated control commands to drive the piston stroke motion as well as to operate the pressure equalization valve. Hence, the timing and frequency for pressure equalization valve to be activated for air exchange can be programmed in the controller. With such pressure equalization valve incorporated the driving air medium can be constantly maintained in full and dry in the pneumatic actuator to guarantee a long-term safe and effective pumping support of the blood pump.

Figure 11:
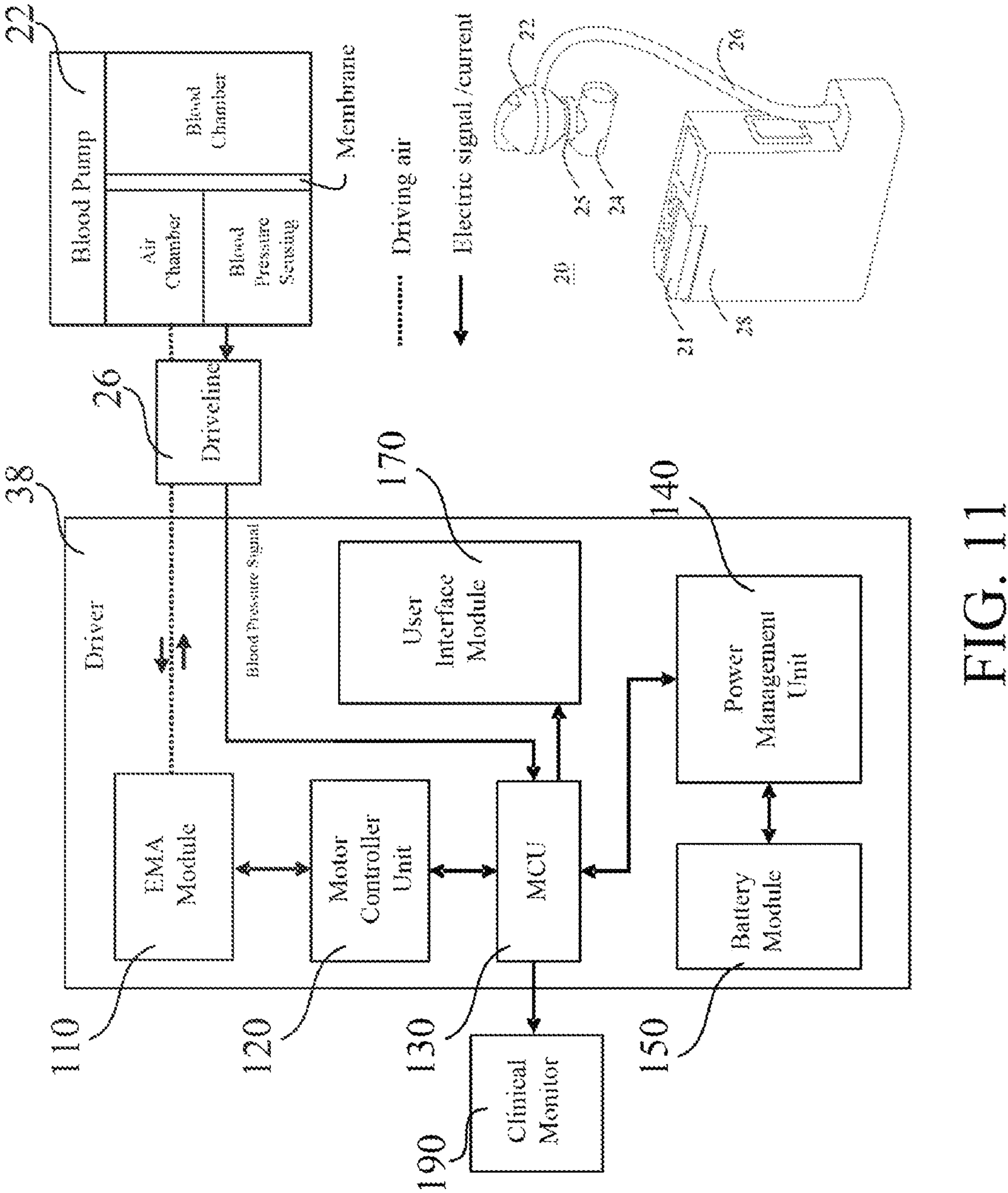
FIG. 11 is a block diagram of the driver functions and the key interconnecting signals that are necessary for the operation of the second embodiment of the present invention.

As illustrated in FIG. 11, a para-aortic blood pump device in accordance with an embodiment of the present invention is divided into three portions. The first portion is largely installed inside the human body (which is an implant) with an externalized end to communicate with the second portion; and the first portion comprises a blood pump (including a blood pump pressure sensor), an aortic adapter and distal driveline segments disposed inside and outside human body, respectively. The second portion is installed outside the human body and comprises a proximal driveline and a driveline electronics module (or known as a driveline interconnector). The third portion is installed outside the human body, which is a driver comprising an electromechanical actuator (EMA), a controller circuit, a main battery, and a reserve battery.

The blood pump pressure sensor is built into the proximal blood pump shell and immersed in a small pressure sensing chamber filled with sensing medium, allowing a continuous monitoring of the blood pump pressure. A distal driveline is attached to the pump housing and provides timed air pressure pulses to command ejection and filling of the blood sac. The distal and proximal drivelines provide a pneumatically driven pressure pulse, generated by the EMA inside the driver, to the blood pump; and transmits an electrical blood pressure signal, generated by the pressure blood pump pressure sensor, to the driver. A driving air path (indicated by a dotted arrow line) and an electrical signal path (indicated by a solid-line) is illustrated in FIG. 11 to describe the functional relationship among the interacted modules. The detailed content of the aortic adapter has been described above. The controller circuit can include a motor controller unit for driving the brushless motor and a micro controller unit as a central processor to process the received pressure signal and generate control commands for motor controller to actuate piston motion.

Figure 12:
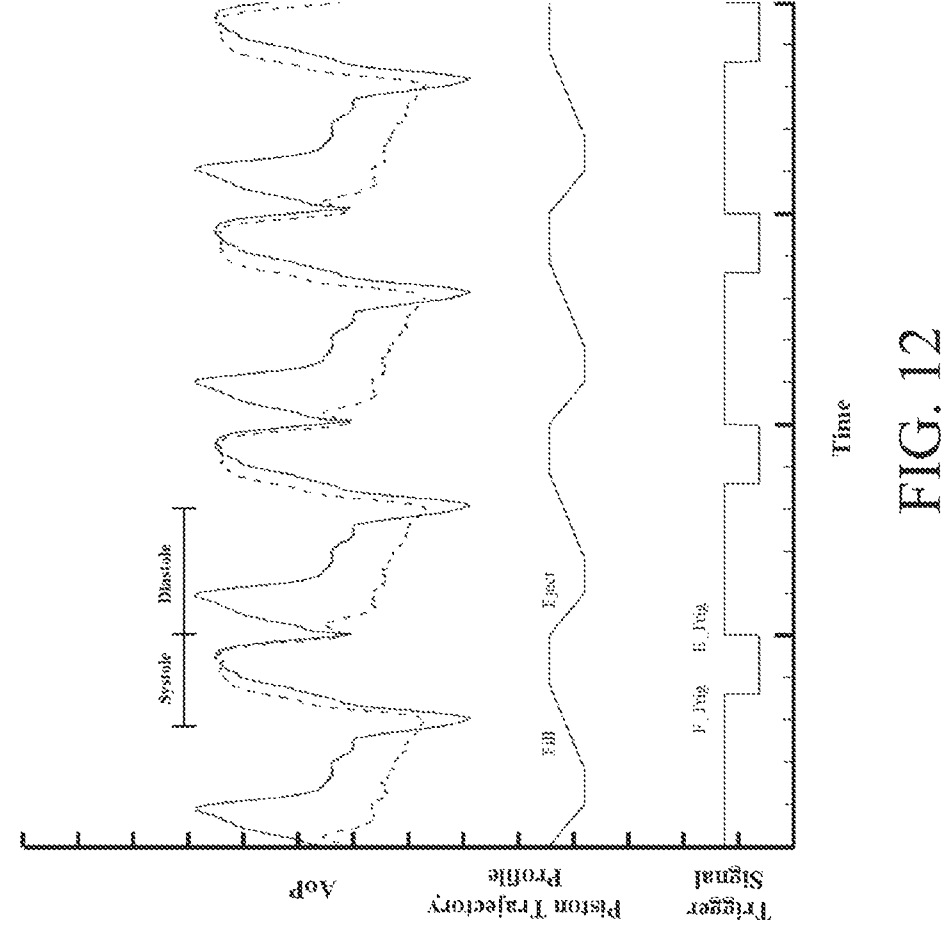
FIG. 12 depicts the trigger-detection commands for electro-mechanical actuator (EMA) piston position in relation to the counter-pulsatile pumping.

With reference to FIGS. 12 and 13, a block diagram of the driver internal functions and the key interconnecting signals that are necessary for actuating the blood pump is shown. The raised embodiments of the present invention are further described, as illustrated in FIGS. 12 and 13. In order to explain the driving relationship between the external driver and the implant, it is necessary to refer to the aforementioned contents of the blood pump, driveline, distal driveline, proximal driveline, aortic adapter and driveline interconnector.

The driver receives blood pump pressure signal (electric signal) and processes the signal using trigger detection algorithm to generate trigger signal that commands the EMA actuation in synchronization with the heart rhythm. Upon receiving the assigned trigger timing, the micro controller unit sends commands to the motor controller unit to drive the piston, from eject-to-fill or from fill-to-eject courses, to provide counter-pulsatile circulatory support.

The architecture of the electronic controller incorporates three functional blocks, namely, a micro controller unit (MCU), a motor control block (motor controller unit), and a power management unit. The following Table provides descriptive outlines for each functional block of the driver 78.

| Function Name | Description |
|---|---|
| Micro Controller Unit (MCU) 130 | The MCU processes the blood pump pressure and generates a trigger that synchronizes the device pumping with the left ventricle. According to the trigger timing, the MCU sends motor commands to the Motor Controller to drive the piston from eject-to-fill or from fill-to-eject positions according to the treatment management settings. It also manages system data storage, system condition monitoring and alarms, commands sent from Clinical Monitor, and patient user interface (LCD display, LED indicators, and audible alarms). |
| Motor Controller Unit 120 | Motor Controller Unit, a motor servo control system that responds to serial commands from MCU to drive the motor with specified position, velocity and acceleration parameters. |
| Electromechanical Actuator (EMA) 110 | EMA drives the piston within a cylinder by a brushless servomotor to provide pulsatile driving pressure to the blood pump. |
| Blood Pressure Sensor 527 | The blood pressure signal is obtained from the Blood Pressure Sensing Element, embedded within the implanted blood pump. The blood pressure signal supplies the pressure waveform for MCU to process and determine the timing for commanding EMA eject and fill action. |
| User Interface Panel 170 | Provides LED indicators, audio alarm, buttons and LCD display. |
| Power Management Circuit 140 | The circuit is to manage the system power, including power switching, battery condition monitoring and charging control. |
| Docked Battery 150 | Provides power to the system when it is not supported by external power. |
| Clinical Monitor 190 | Collects and displays real-time device waveform data; initiates driver parameters setting and stores patient identification data; perform long-term condition monitoring and diagnosis trending analysis. |

The signal acquisition, transmission, processing, and the control logic and command generation and EMA actuation to produce pressure pulse to drive the blood pump is illustrated in FIGS. 12 and 13 for the exemplified embodiments previously elucidated.

FIG. 14 depicts the trigger-detection commands for EMA piston position in relation to the counter-pulsatile pumping. In FIG. 14 the unassisted aortic pressure (AoP) waveform is expressed in dotted line whereas solid line represents the assisted aortic pressure waveform. When the driver operates with Auto Run mode, the driver operation is initiated and the system carries out a "fill-eject-fill-eject . . . " cyclic pumping, which represents a normal synchronous counter-pulsation operation. The MCU monitors blood pump pressure (BPP) signals (electric signal) and detects the left ventricle end-diastole (LVED) timing. Upon detection of LVED timing, the MCU generates a F_Trig signal. The time interval between two consecutive F_Trig signals represents an instantaneous cardiac cycle interval (or period). Based on an estimated heart rate calculated from the preceding cycle intervals, the MCU determines the timing, the E_Trig signal, for blood pump ejection. The E_Trig signal provides the timing to command the motor controller unit to drive the EMA according to the predetermined position, velocity, and acceleration profiles. When the ejection stroke is completed and after an optimized dwell time elapse, the EMA is commanded to perform a pre-fill action with a gentle filling speed until the F_Trig signal shows up. Upon receiving the F_Trig signal, the EMA starts to perform a residual fill stroke at a specified piston speed.

When the MCU loses the BPP signal (electrical signal) sent from the blood pump, a washout mode is launched automatically by MCU to drive the EMA, operating at a predetermined pumping rate and driver stroke volume. The washout mode is used to prevent the formation of thrombus in the blood sac, which is a device protection mode instead of providing synchronous circulatory support.

The para-aortic blood pump device of the present invention, with its non-occlusive para-aortic feature, in principle, has a better counter-pulsatile support efficacy as compared to the intra-aortic balloon pump (IABP). Unlike the bedridden or ambulatory IABP patients who have to stay in hospital, the portable para-aortic blood pump device allows the patients to leave the hospital and have ambulatory capability to live a better life at home. Hence, the para-aortic blood pump device of the present invention may further improve patient's disease conditions and quality of life, in addition to the economic benefits gained from a shorter hospital stay.

The trend of LVAD use has been plateaued in recent years, mainly because its application is only indicated to the terminal-stage heart failure patient cohort. Applying early intervention LVAD therapy to the less-sick heart failure patients has long been a clinical objective, which is expected to imposing substantial impact on the future cardiac medicine advancement provided by the broadened use of LVAD therapy. Clinical evidences have shown that certain non-ischemic cardiomyopathy patients supported by LVAD, administered in moderate-to-severe heart failure stage, can be improved with myocardial reverse remodeling toward functional upgrade or sustained myocardial recovery. Nevertheless, this intention of early intervention must be ushered by two enabling factors: an easy and safe surgical procedure, and an effective and adaptive support scheme accompanying disease development. Continuous-flow VAD support is non-physiologic, which deranges the supported heart away from a normal course of recovery. The counter-pulsatile support, however, is physiologic and meets the therapeutic requirement by providing systolic contraction unloading and diastolic perfusion augmentation to promote myocyte reverse remodeling. In summary, the treatment strategy provided by this para-aortic blood pump invention aligns with the early intervention trend development in cardiac medicine. Salutary attributes provided by the para-aortic blood pump device, such as adaptive partial-support, less invasive surgery and counter-pulsatile therapeutics will collectively make the present invention a prospective candidate to contribute to the future advancement of heart failure treatment.

The blood pump of each of the aforementioned embodiments is further described below.

Figure 13A:
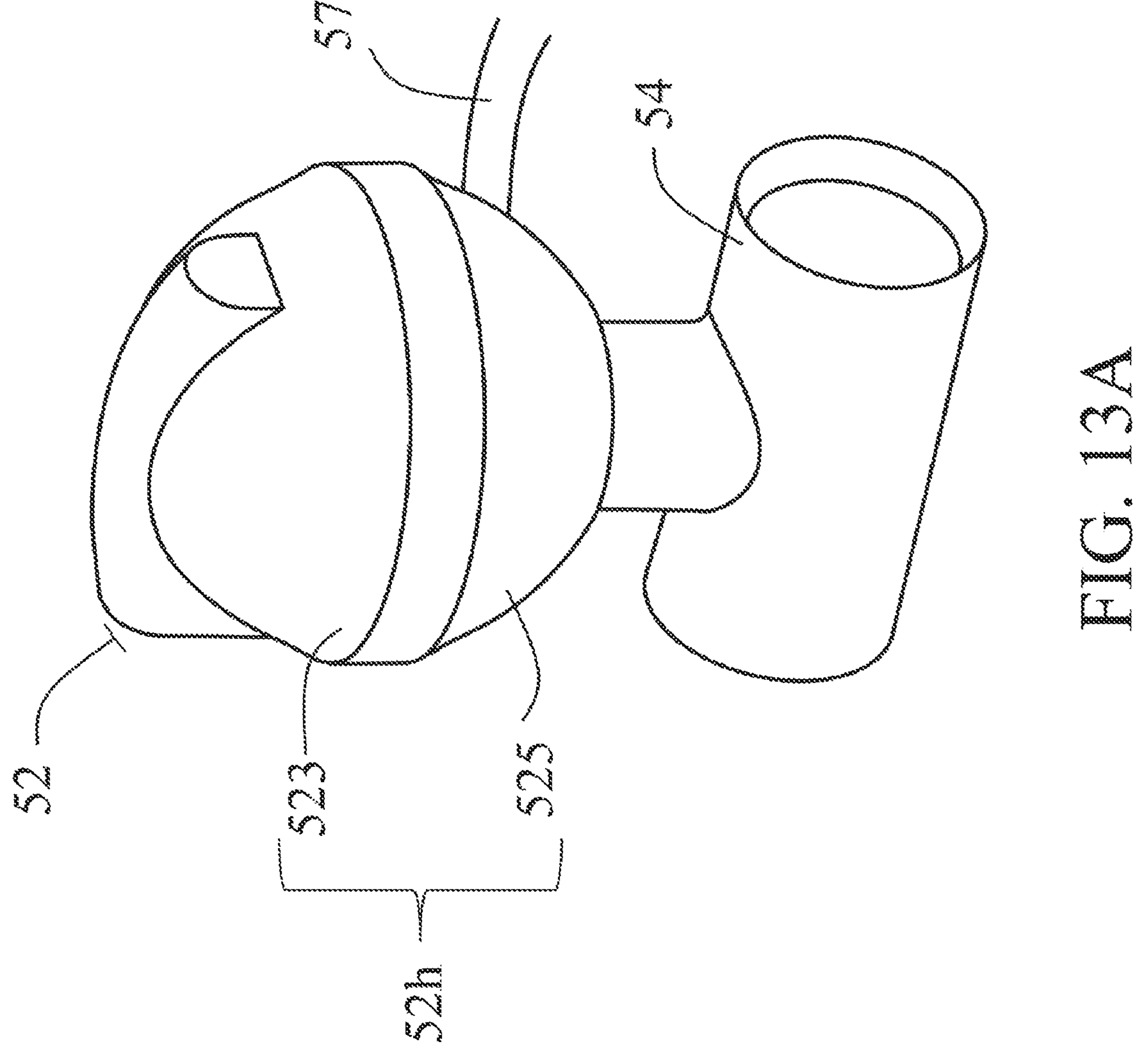
FIG. 13A is a perspective view showing a para-aortic blood pump implant in accordance with the first or third embodiment of the present invention.
Figure 13B:
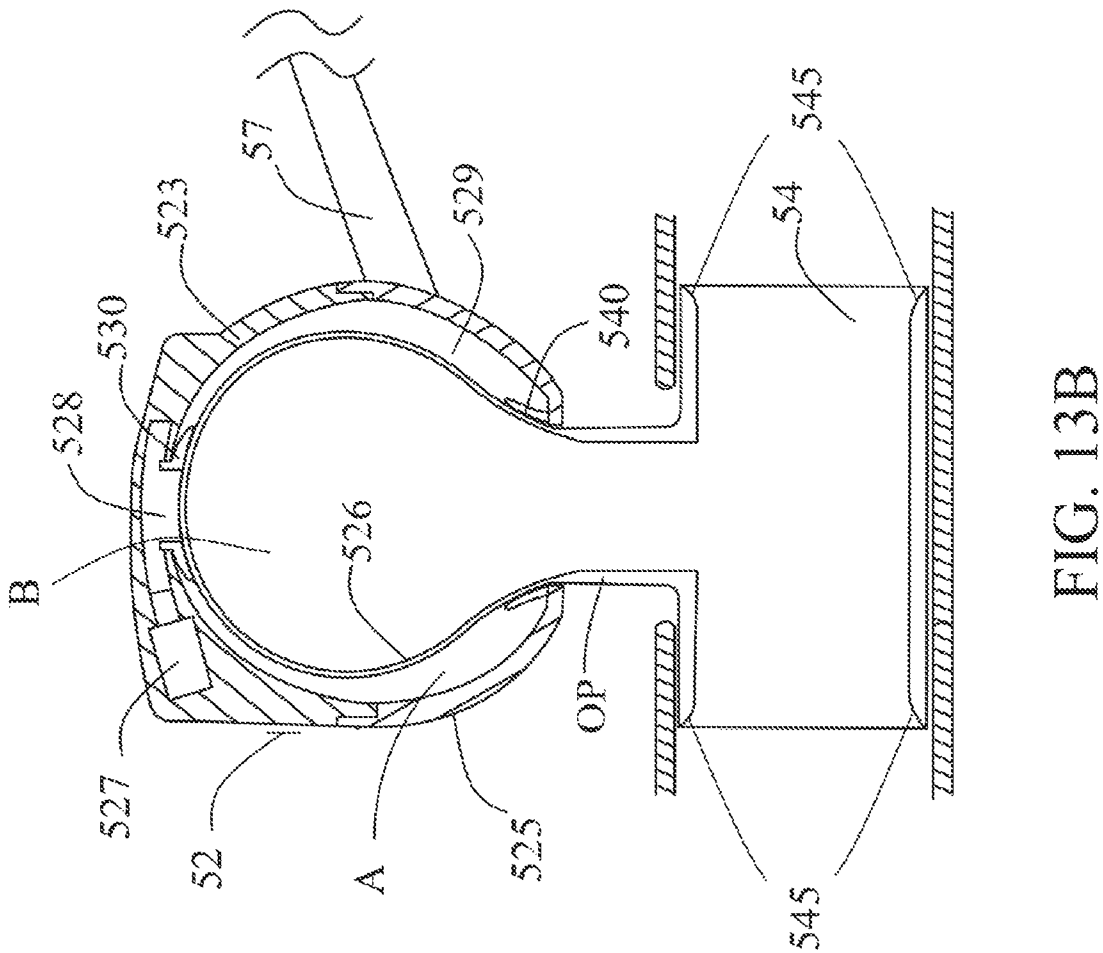
FIG. 13B is a sectional view showing a para-aortic blood pump implant in accordance with the first or third embodiment of the present invention.

With reference to FIG. 13A and FIG. 13B for the schematic and sectional view of a part of a para-aortic blood pump device installed in human body in accordance with the first and third embodiments of the present invention, the implant subsystem of the para-aortic blood pump device comprises the blood bump 52, the aortic adapter 54, and the driveline (or distal driveline) 57 attached to the blood pump 52. The blood pump 52 comprises a rigid or semi-rigid pump housing 52*h* of the blood pump 52 and a blood sac 529 having its proximal end closed and distal end open and seamlessly integrated with the aortic adapter 54. The blood sac 529 is formed by an oval-shaped sac membrane 526, moreover, the blood sac 529 is anchored via a proximal stem 530 to the proximal shell 523 of the pump housing 52*h* and via a distal stem 540 to the distal shell 525 of the pump housing 52*h*. The space in the blood pump is partitioned into a blood chamber B and an air chamber A separated by the oval-shaped flexible sac membrane 526 suspended via a pair of stress-relief stems (proximal stem 530, distal stem 540) attached to the pump housing 52*h*. The blood chamber B is for blood storage and the air chamber A is for receiving driving air. The pump housing 52*h* comprises the proximal shell 523 in which a pressure sensor (or a blood pressure sensor) 527 is hermetically embedded, and the sensed pump pressure is transmitted across the sac membrane 526, propagated in an incompressible liquid or jelly housed in a closed pressure sensing chamber 528, and finally received by the pressure sensor 527. After receiving the sensed pump pressure, the pressure sensor 527 generates an electrical blood pressure signal. The implanted subsystem components are designed with a size and a shape that can be implanted in patients with a body surface area (BSA) of 1.2 $m^2$ or larger.

Figure 14A:
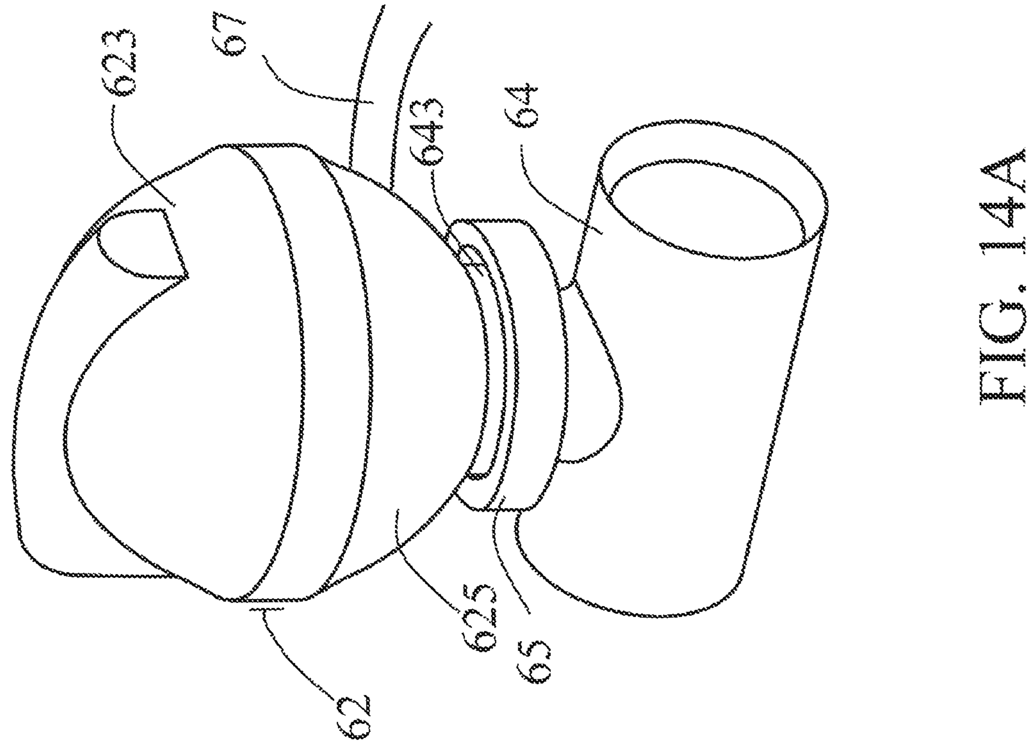
FIG. 14A is a perspective view showing a para-aortic blood pump implant in accordance with the second or fourth embodiment of the present invention.
Figure 14B:
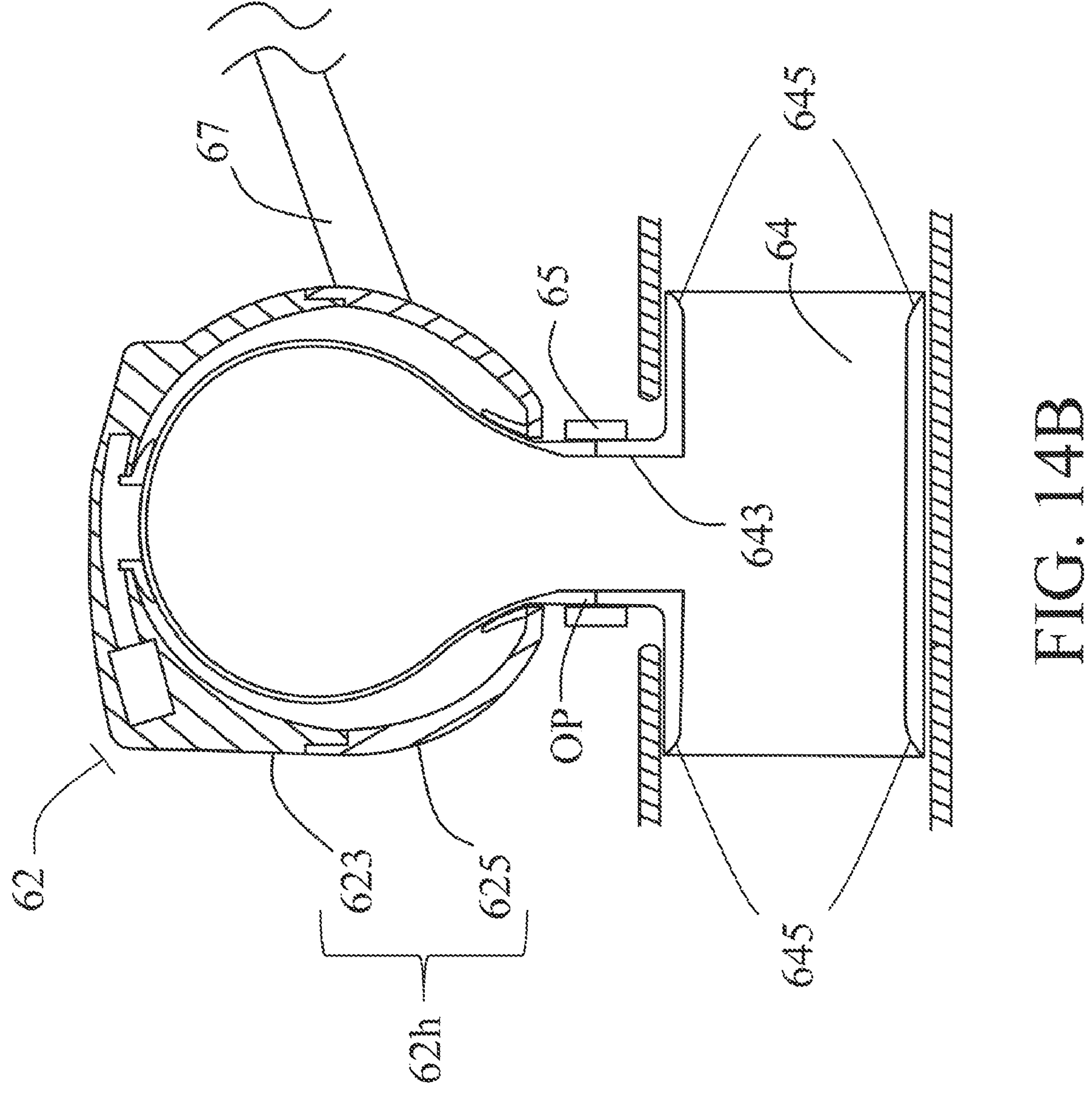
FIG. 14B is a sectional view showing a para-aortic blood pump implant in accordance with the second or fourth embodiment of the present invention.

With reference to FIG. 14A and FIG. 14B for the schematic and sectional view of a part of a para-aortic blood pump device installed in human body in accordance with the second and fourth embodiments of the present invention, the implant subsystem of the para-aortic blood pump device comprises the blood pump 62, the aortic adapter 64, the coupler 65 and driveline (or distal driveline) 67 attached to the blood pump 62. The coupler 65 is used to couple the blood pump 62 to the aortic adapter 64 to access the recipient's vascular system. The blood pump 62 comprises a pump housing 62*h*, which further comprises a proximal shell 623 and a distal shell 625. The construct of the present blood pump 62 is similar to that disclosed in FIG. 13B, except that the distal opening OP is separated from and independent with the aortic adapter. The coupler 65 is placed around the flexible neck 643 of the aortic adapter 64. In the following, we use the design disclosed in FIG. 13B to further explain the blood pump design and the underlying design rationale.

Referring to FIG. 13B, the blood pump 52 comprises a molded rigid or semi-rigid blood housing 52*h* which further comprises a proximal shell 523 and a distal shell 525. The housing 52*h* has a single opening OP connected to the aortic adapter 54 to access the recipient's vascular system. The opening OP of the blood pump 52 is seamlessly manufactured together with the aortic adapter 54 (or the blood pump 52 and the aortic adapter 54 are integrally formed), which provides a smooth and continuous interface transition to the neck of the aortic adapter 54. Such integrated blood sac 529 and aortic adapter 54 assembly is attached to the pump proximal shell 523 and distal shell 525 via a bonding to the proximal stem 530 and distal stem 540, respectively. The blood sac 529 is anchored to the top of the proximal shell 523, such that a small, non-flexing circular portion of the blood sac 529 is disposed next to a pressure sensing chamber 528 in the shell 523.

A miniaturized pressure sensor 527 is built into the pump shell 523 and fluid communicated to the enclosed pressure sensing chamber 528. This arrangement allows a continuous monitoring of the blood pressure contained in the blood sac 529. Since the pressure sensor 527 is not blood-contacting, the long-term sensor reliability and fidelity is assured by the protection of the pump housing 52*h* that isolates the sensor 527 and its electric circuit from the influence of chemical corrosion and protein adherence arising from the direct blood contact.

A driveline 57 end is attached to the pump shell 525 to provide timed air pressure pulses for actuating the eject or fill stroke of blood out of or into the blood pump 52. The driveline design can be multi-luminal or multi-layered so as to accommodate the electrical wires for pressure signal transmission. Metallic coil or fabric mesh can be adopted as the wall reinforcement to enhance the anti-kink capability of the driveline 57. The overall geometry of the blood flow passage in the present blood pump is wide, along with the valveless aortic adapter design and pulsatile pumping operation, constituting a superior blood handling property that avoids high shear-induced hemolysis as well as low flow speed generated thrombus formation or thromboembolism.

The blood sac 529 of the blood pump 52 includes an innovative design to make the sac membrane 526 durable. The blood sac 529 is an oval-shaped membrane body of revolution to the centerline of the blood pump 52. There are two polymeric stems (proximal stem 530, distal stem 540) bonded at both housing 52*h* ends, configured respectively to be in a circular disc or an annulus shape, and working as a flexing/stretching relief mechanism to alleviate stress concentration when attached to the rigid housing 52*h*. During pump ejection, the sac membrane 526 will be compressed or folded into a tri-lobe shape where the highest strain often occurs at the creased folding line near the rim of the stem attachment (proximal stem 530, distal stem 540). This local high membrane stress/strain arising from large membrane deformation is substantially reduced or absorbed by the deformation of the flexible stem rim as a bendable suspension. Notice that the tri-lobe folding pattern is non-stationary, with creases changing from place to place as influenced by the gravitational direction. In fact, a patient's body posture and orientation including the positions of standing, sleeping, sitting, exercising, etc. may change from time to time in daily activities. The gravitational effect or the body force acting on the stored blood volume in the blood pump 52 is hence constantly changing, resulting in a non-stationary crease line initiation and formation. Such running membrane folding line constitutes a unique fatigue resistance feature of the present invention. It is anticipated that the present blood pump 52 will possess a much longer durability than that of the conventional fixed folding line membrane design.

Membrane folding and expansion are intimately related to the vortex flow pattern contained in the blood sac 529. The aforementioned sac design features a running folding line formation that makes the vortex structure pattern alternatingly change in response to the folded membrane pattern. The washout effect in the blood pump 52 is thus strong and non-stationary, characterized by a random walk-like vortical flow movement. Such randomness in the pump vortex flow structure helps washout the entire blood-contacting surface without creating any fixed low-speed zone near the membrane wall or in the crease area. It has been observed in animal trails that the present blood pump is very thromboresistant.

The (distal) driveline of each of the aforementioned embodiments is further described below.

Referring to FIGS. 5 and 6 for a schematic view of the driveline used to connect the blood pump 92 with the driver 98. The intracorporeal (distal) driveline 991, 97 of the driveline pneumatically connects the blood pump 92 to the electro-mechanical actuator housed within the driver 98 and also carries the electrical signals acquired from the blood pump pressure sensor 527 (see FIG. 13B). The (distal) driveline 991, 97 has one end attached to the blood pump housing and the opposite end having a small external connector for pneumatic and electrical communication. The (distal) driveline 991, 97 is tunneled subcutaneously and exits the skin. The outer diameter of the (distal) driveline 991, 97 is designed to be small and the tubing material is flexible to minimize the exit site EX stress to the patient's comfort. A portion of the (distal) driveline 991, 971 is covered with a porous fabric to promote tissue ingrowth so as to make the exit site infection resistant. The externalized (distal) driveline 991, 973 is secured with a short distance beyond the skin exit site EX.

The (distal) driveline 991, 971 and its connector are designed to withstand the tensile loads applied during surgical externalization. Post-operatively, the (distal) driveline 991, 971 is constantly influenced by muscular motion-induced loads, and the (distal) driveline 991, 971 is designed to withstand these loads for their intended service life. The externalized portion of (distal) driveline 991, 971 is also designed to be biocompatible and chemically resistant to cleaning agents and disinfectant in clinical use.

The (proximal) driveline of each of the aforementioned embodiments is further described below.

The (proximal) driveline 993, 99 is used to connect the (distal) driveline 991, 97 to the driver 98. The (proximal) driveline 99 has a driveline interconnector 93 at one end and a driver connector at the other end. The said driveline interconnector 93 encloses a circuit board, which converts analog blood pump pressure signal into digital signal, and a vibrator that provides a tactile feedback in addition to the audible alarms. The driveline interconnector 93 comes with a flat shape to prevent torsion from being generated to the (distal) driveline 973 when the driveline interconnector 93 is anchored against the patient's skin. Further, the driveline interconnector 93 and the driveline outer cover are designed to be sealed and protected against water or moisture ingression. Since the (proximal) driveline 99 is installed externally, it can be replaced and/or maintained when deemed necessary, hence eliminating the surgical blood pump replacement required when the (proximal) driveline 99 is damaged beyond repairable.

Valveless blood pump has two advantages in blood handling characteristics: 1) having no annoying valve sound and valve-induced blood cell damage, thrombus formation and thromboembolism; 2) being more thromboresistant because the two-way pulsatile flow has better surface cleaning effect to minimize protein adhesion and avert interface discontinuity-related clot formation over the blood-contacting artificial surfaces. The flow passage in the valveless pulsatile pump is uniformly much wider that those in the valved pulsatile or continuous-flow rotary pumps. Hemolysis (rupture of red blood cell membrane) generally takes place at narrow flow passages with high flow velocity gradient, such as the gaps between the valve ring and leaflet of a valved pulsatile pump. In addition, low-speed recirculation or stasis zone often exists in the back side of the opened valve which may encourage thrombus to be generated. In a sharp contrast, in a valveless pulsatile blood pump, the shear stress applied on blood cells is literally order of magnitude smaller, and the low-speed stasis zone associated with valve geometry and motion is substantially eliminated, which leads to less blood cell damage or platelet activation, less clot formation and aggregation and translates to lower dose of anticoagulant use and easier and safer post-operative care.

Figure 15:
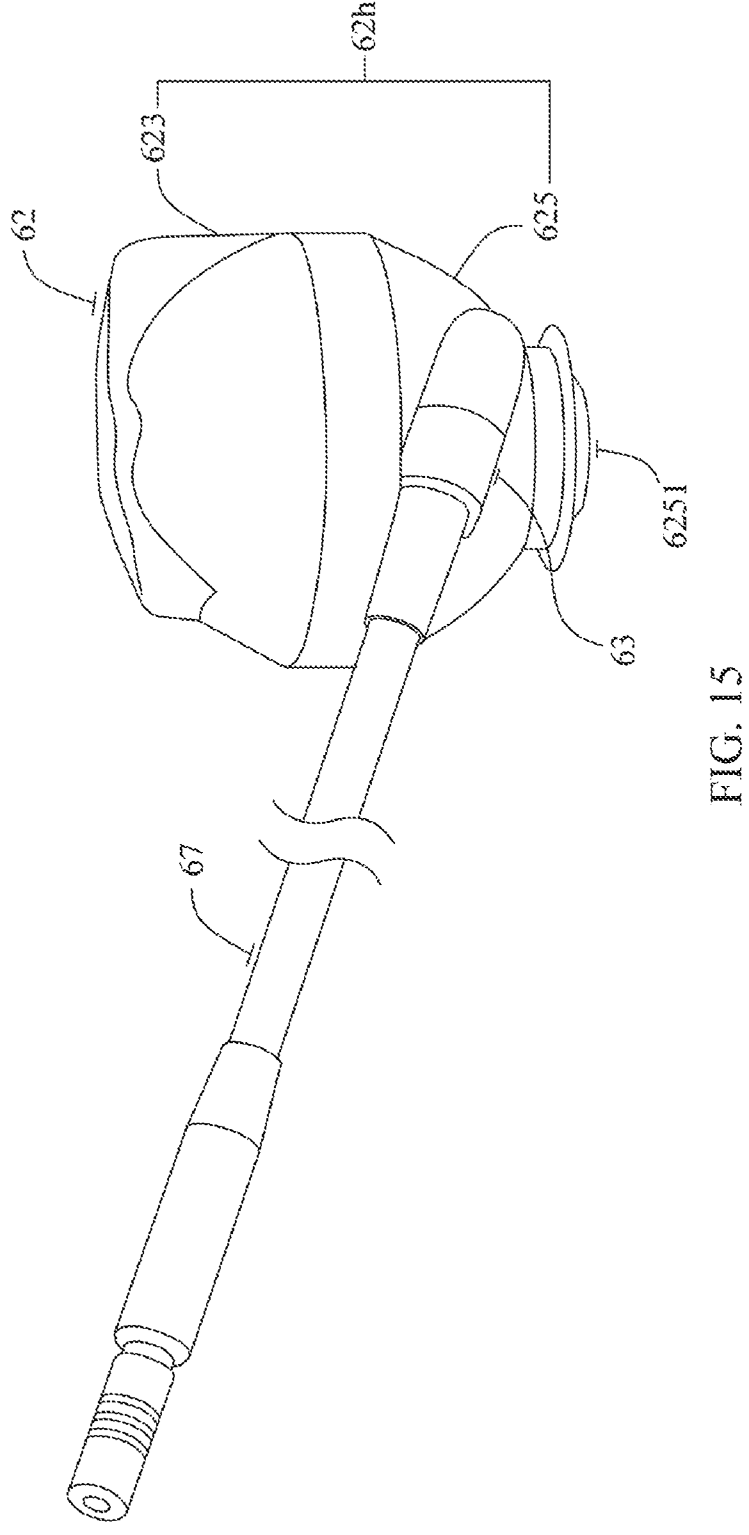
FIG. 15 shows the driveline connection to the pump housing of the blood pump being accomplished via a feedthrough on the distal shell according to another embodiment of the present invention.
Figure 16:
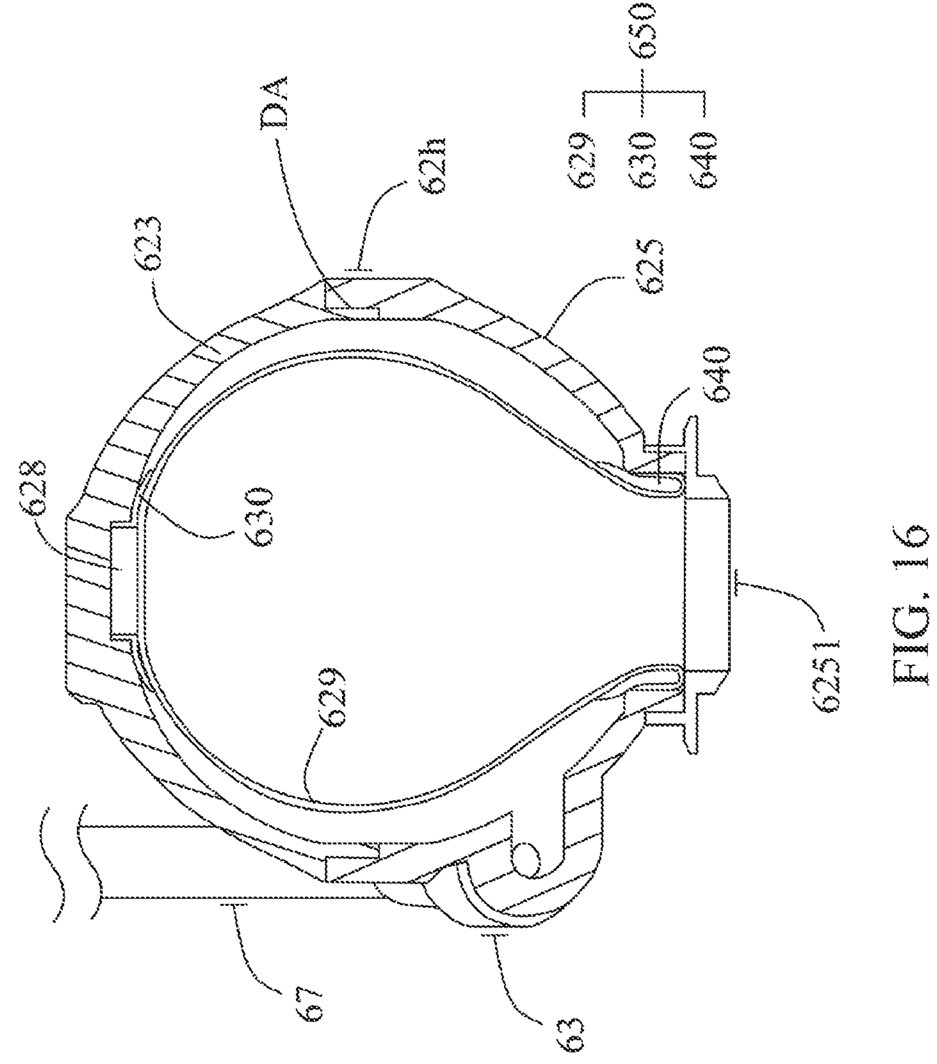
FIG. 16 shows a sectional view of the blood pump illustrated in FIG. 15.
Figure 17:
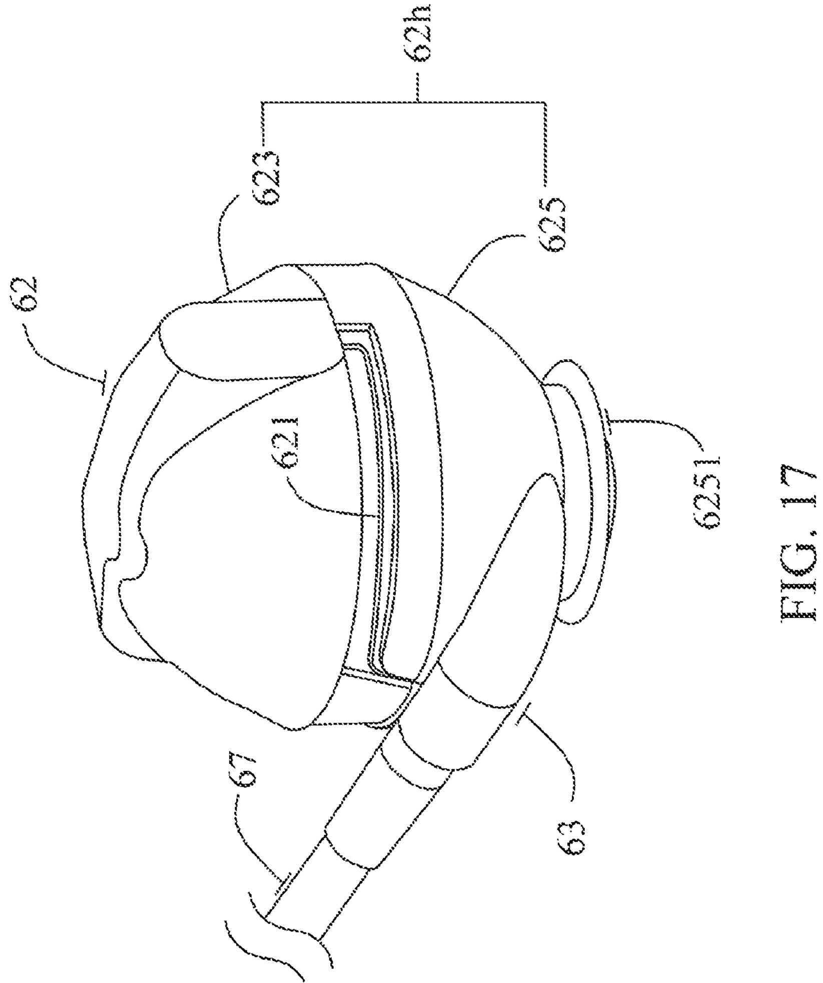
FIG. 17 shows a superficial trench design for extending the electric wires from the feedthrough disposed in the distal shell to the pressure sensing chamber in the proximal shell.

FIGS. 15 to 17 shows the blood pump 62, the driveline 67 and the feedthrough 63 according to another embodiment of the present invention. This embodiment stresses the anatomic adaptivity for an easier blood pump placement and driveline externalization.

As shown in FIGS. 15 and 16, the driveline 67 is connected to distal shell 625 of the blood pump 62. The blood pump 62 has the oval-shaped blood sac and stem assembly 650 (including sac 629 and stems 630, 640), the pump housing **62*h* (having the proximal shell 623 and the distal shell 625), and the pressure sensing system 628 embedded in the proximal shell 623. The design details of the oval-shaped blood sac and stem assembly 650, the distal shell adapter 6251, the pressure sensing system 628, and the driveline 67** are substantially identical or corresponding to those of the aforementioned embodiment, and the modular and functional descriptions are not repeated herein.

In this embodiment, the feedthrough 63 is disposed in the distal shell 625 of the pump housing **62*h* for coupling the driveline 67 to the pump housing 62*h*. Further, the feedthrough 63 is configured in a body-fitted shape adjacent to the distal shell 625, making driveline connection in a tangential direction to the pump outer surface. Such body-fitted feedthrough design renders pump housing 62*h* design adaptive to the anatomic space available for blood pump placement. The blood pump 62 can be rotatably connected to the interface adapter 501 and allow the driveline 67** be routed with best suited orientation to enable a smooth subcutaneous tunneling and skin exit. In this way, it favors to anatomic adaptivity to the implant site geometry.

In this embodiment, the feedthrough 63 is remotely suited in the distal shell 625 while the pressure sensor 6271 (see FIG. 25A) and sensing chamber 628 are located in the proximal shell 623. More engineering work has to be performed to separate signal transduction route from pneumatic communication route and assures that the blood pump 62 be sealed and protected against biochemical fluid invasion that might damage the fidelity of signal transduction after device implantation.

FIG. 17 shows the pump housing 62*h* has a superficial trench 621 formed on the outer surface of the distal shell 625 and above an overlapped bonding area DA (FIG. 16) of the proximal shell 623 and distal shell 625. The superficial trench 621 is configured to let the electric wires be extended from the outlet of feedthrough 63, along the trench above the overlapped bonding area and reach the electrodes 6274 of the pressure sensor 6273 (see FIG. 25B). In some embodiments, the trench 621 is sealed by a potting waterproof material and/or a ring-shaped cover to maintain a smooth outer surface in order not to irritate or hurt the contacted tissue.

Figure 18A:
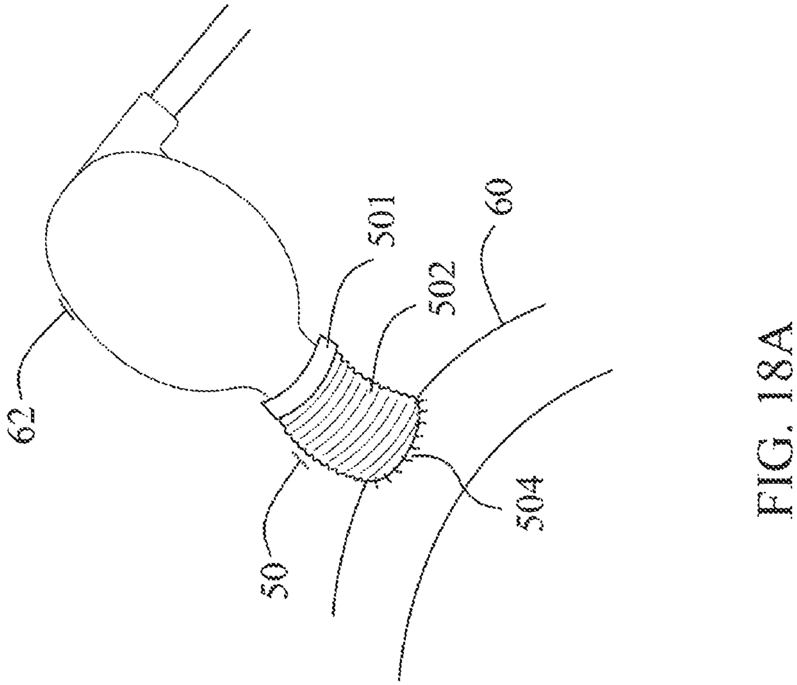
FIG. 18A shows a surgical end-to-side anastomosis of the present blood pump invention to an artery via the use of an interface adapter coupling.
Figure 18B:
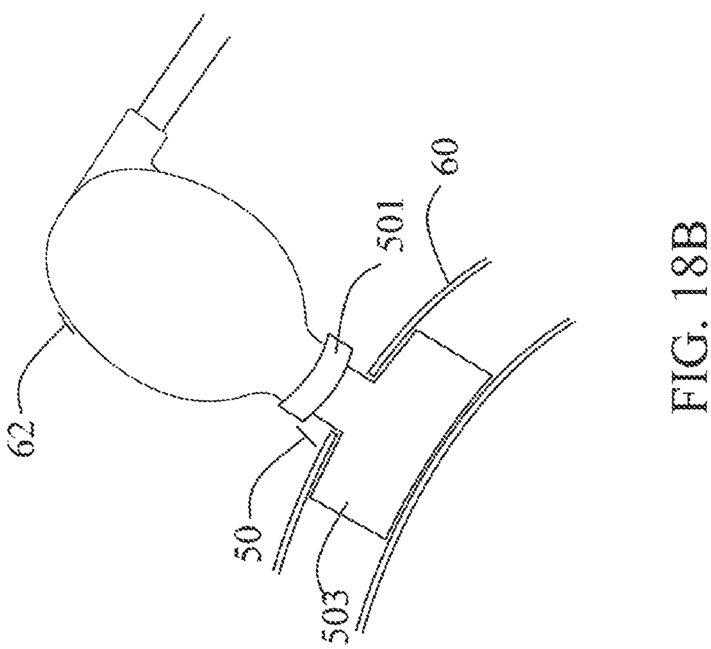
FIG. 18B shows coupling of the present blood pump to an artery via an insertion type connection method using a T-shaped endovascular connector coupled by an interface adapter.

As illustrated in FIGS. 18A and 18B, the aortic connector 50 generally requires an interface adapter 501 to serve as a coupling mechanism to connect the blood pump 62 onto the target artery 60. The distal end 504 of the connector 50 opposite to the interface adapter 501 is placed in the vascular wall of the artery 60, and in fluid connection with the human circulation. The proximal end (the interface adapter 501) of the aortic connector 50, however, has a smooth interface transition to geometrically match with the inlet morphology of the blood pump 62. A coupler is commonly required to integrate together the proximal end of the connector 50 (the interface adapter 501) with the inlet of the blood pump 62. There are some embodiments that can be used as the aortic connector 50. The one shown in FIG. 18A is the end-to-side anastomosis of a Dacron or Polytetrafluoroethylene (PTFE) graft 502 sutured with the target vessel 60, which can be used in vascular surgery. In some other embodiments, such as the one shown in FIG. 18B, an insertion type aortic connector 503 is used, such as the T-manifold shaped adapter 503 disclosed in U.S. Pat. US 2008/0300447A1, entitled "Dual-pulsation bi-Ventricular Assist Device."

Figure 19:
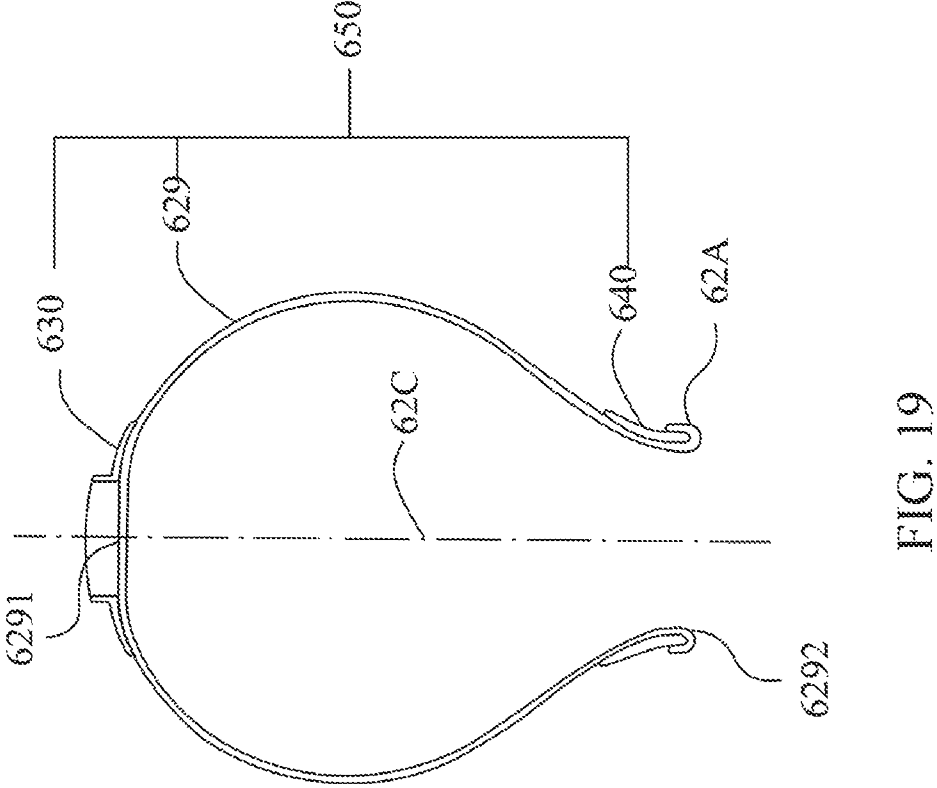
FIG. 19 illustrates a sectional view of the body of revolution of an integrated axi-symmetric oval-shaped blood sac and stem assembly including a sac, a proximal stem and a distal stem.
Figure 20:
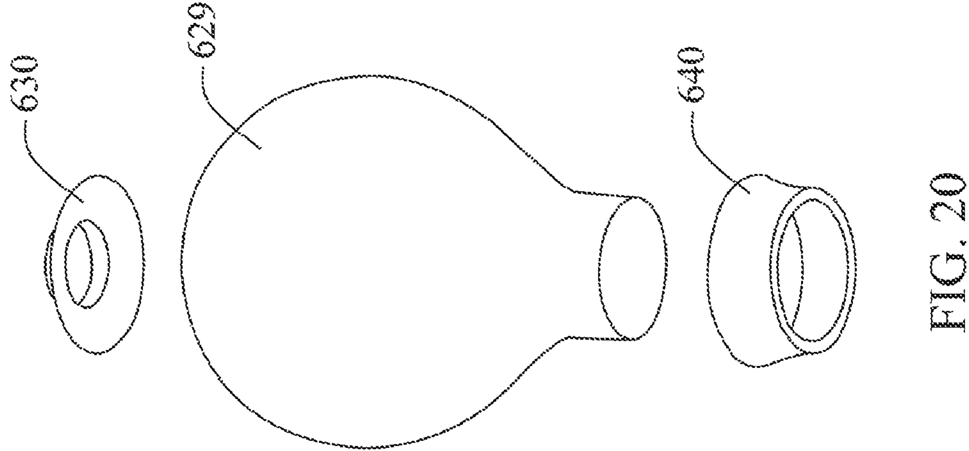
FIG. 20 is an exploded view showing the components used for the construction of the axi-symmetric oval-shaped blood sac and stem assembly (Note that the sac is in its original shape before bonding integration to the proximal and distal stems illustrated in FIG. 19)

FIGS. 19 and 20 illustrate respectively the assembly and components of the long-duration axi-symmetric oval-shaped blood sac and stem assembly 650 design. The polymeric material chosen for these components can be, but not limited to, segmented polyurethane with various appropriate durometers. The constituent parts of sac and stem assembly 650 includes a flexible membrane sac (blood sac) 629, a proximal stem 630, and a distal stem 640, which are all made in axi-symmetric shapes and integrated together into an assembly of body of revolution relative to a common centerline 62C of the blood pump 62. The proximal stem 630 is located at the proximal end 6291 of the sac 629, and the distal stem 640 is located at the distal end 6292 of the sac 629.

Figure 21:
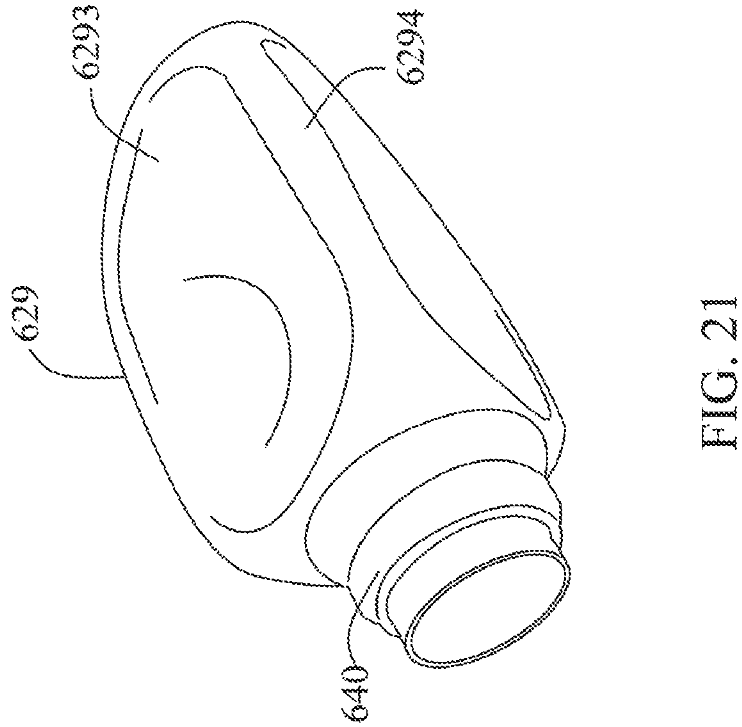
FIG. 21 illustrates the buckled tri-lobe sac configuration (eigenmode) at the end of ejection of the blood sac illustrated in FIG. 19.

FIG. 19 shows the integrated sac and stem assembly 650 of which the end of the distal stem 640 is wrapped and bonded with the inverted membrane 62A at the distal end of the sac 629. FIG. 20 illustrates the constituent parts before bonding. In general, the sac 629 is made by dip molding while the stems 630, 640 are injection molded. There is no preferred azimuthal angle for sac deformation to be biased. In theory, thin-walled sac constructed in axi-symmetric oval shape will buckle into a tri-lobe configuration 6293, as shown in FIG. 21, when pressure differential across the membrane exceeds certain threshold. Such membrane buckling only matters with the final tri-lobe configuration 6293 (eigenmode) and where the creases 6294, or folding lines, shall take place is decided by the initial perturbation that triggers the initiation of buckling instability. The thickness uniformity in cross-sectional planes cut perpendicularly to the centerline (or the axis of revolution) 62C of the assembly 650 of the blood pump 62 is critical. Care must be exercised to maintain a high-precision sac manufacturing such that an axi-symmetric shape is assured. In real life application, gravity direction stands out as the dominant factor in folding line initiation. Postures of device recipients constantly change, so is the gravity direction relative to the blood pump orientation, according to the daily activities the patient is undergoing, such as standing, sitting, exercising, sleeping, etc. The creases 6294 of sac deformation, hence, appear in a random walk-like pattern which disperses the high-strain creases non-stationarily over the entire sac. Avoidance of high-strain region dwelling at fixed location, therefore, is the key design guideline to make the sac long-duration.

The embodiment of the present invention innovates a running folding line attribute which makes the high-strain location appearing non-stationarily in the membrane to prolong sac fatigue life. The detrimental stress concentration phenomenon frequently associated with the flexing blood sac is hence improved. Based on this fundamental change in flexing pattern behavior, the fatigue life of membrane will significantly increase attributable to this non-stationary folding line formation characteristic that disperses the high strain areas all over the sac. Further, a salutary outcome accompanying this non-stationary sac deformation pattern resides on the vortex washout effect enhanced within the blood sac. The sac surface will be washed more thoroughly with a random walk-like vortex formation and traversing. The probability of producing constant low-speed recirculation zone dwelling in the near-wall region or creases of the folding lines, hence, will be greatly reduced, resulting in a long-duration, thrombo-resistant blood pump design.

Figure 22:
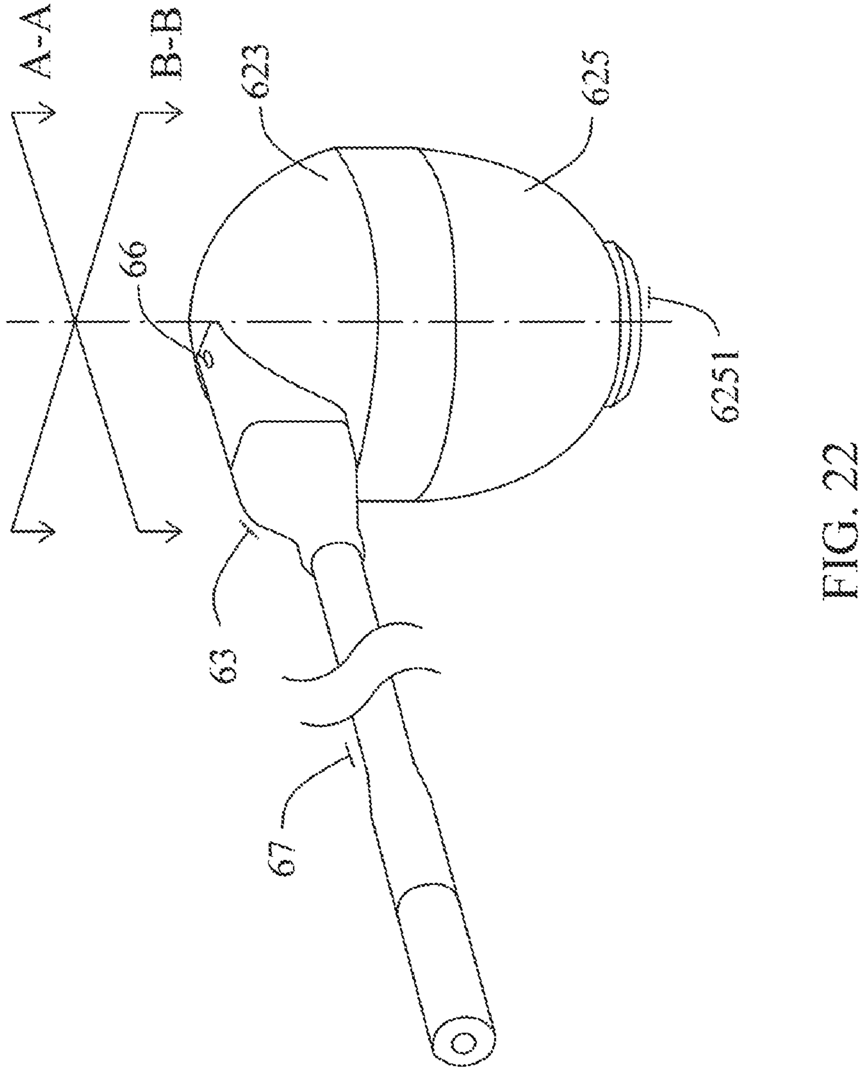
FIG. 22 depicts a perspective view of the driveline connected to the proximal shell of the blood pump via the feedthrough.
Figure 23A:
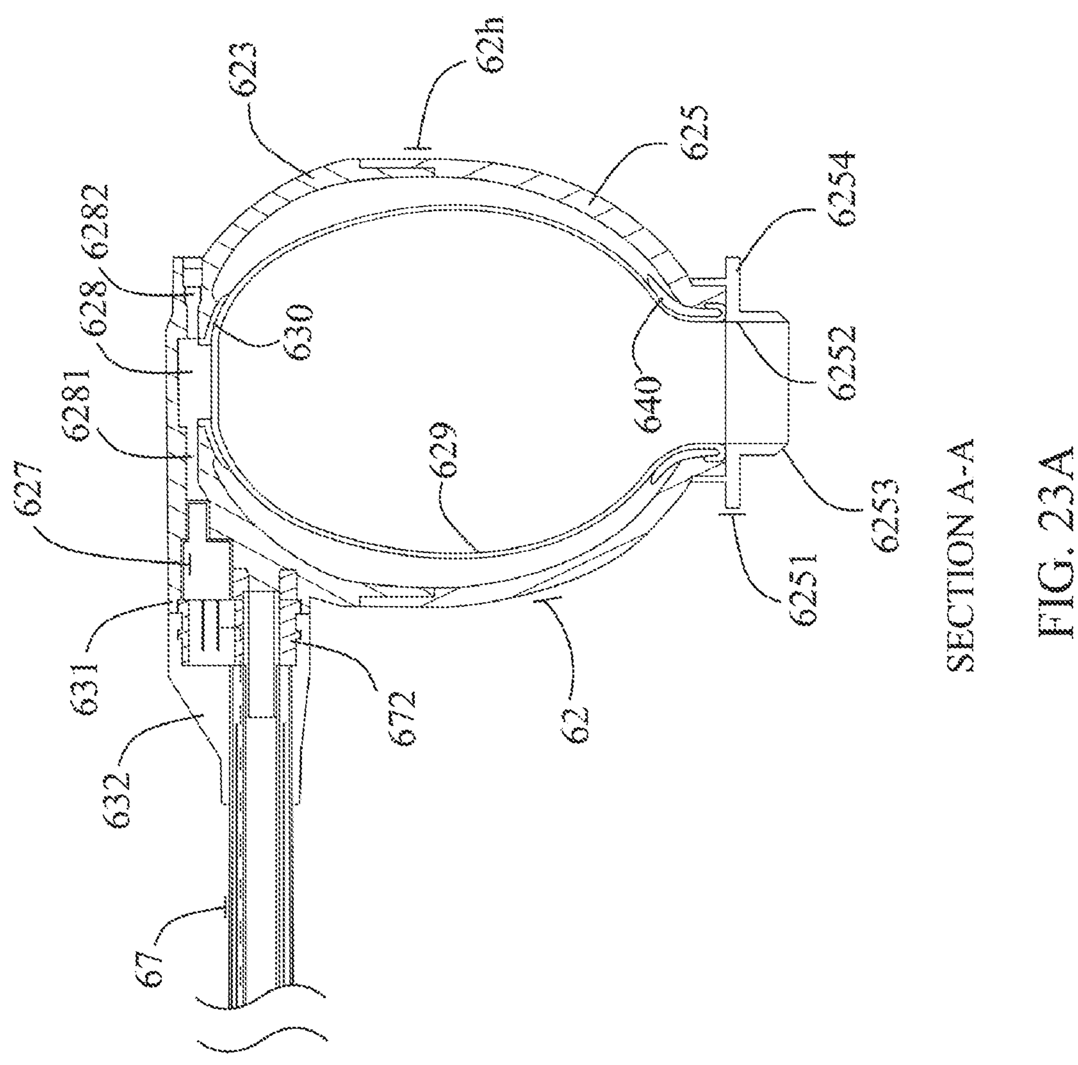
FIG. 23A illustrates a sectional view of the blood pump and distal portion of the driveline taken along the section A-A in FIG. 6.
Figure 23B:
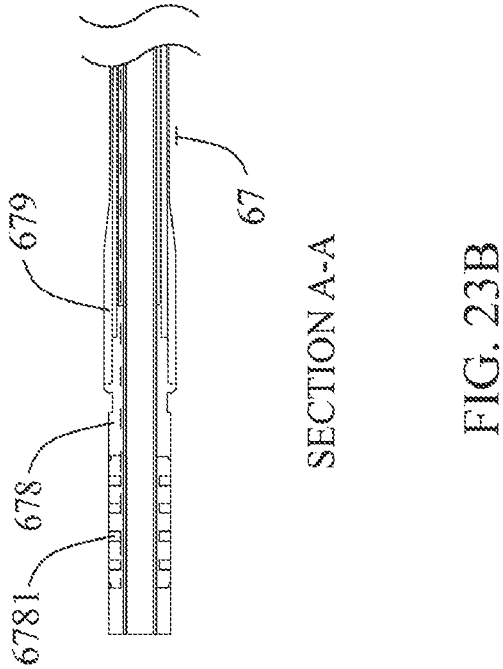
FIG. 23B shows a sectional view of the proximal end of the driveline taken along the section A-A in FIG. 22.

FIGS. 22, 23A and 23B show an exemplary embodiment of how an integration method is adopted for mounting the blood sac assembly onto the pump housing 62*h* as well as joining a driveline 67 to the proximal shell 623. The distal driveline 67 has its first end connected to the blood pump 62 at the feedthrough 63 and the second end manufactured as a solid connector 678 having electrodes 6781 flushed mounted and covered by a bend relief 679.

The blood sac 629 is anchored onto the pump housing 62*h*, which includes a proximal shell 623 and a distal shell 625, to facilitate pump fill and ejection actions. In general, the flexural properties of the sac 629 and the housing 62*h* are vastly different. To accomplish a long-duration sac design, it requires an intermediate suspension to be installed to render the pump assembly continuous in structural property transition, in particular the membrane flexural deformation. A pair of flexible stems 630 and 640 is adopted as the suspension that integrates the blood sac 629 with the housing 62*h*. As shown in FIG. 23A, the proximal stem 630, configured in a disc shape, connects with the proximal shell 623; whereas the distal stem 640, in an annulus form, connects with the distal shell 625. Mechanically, the proximal and distal stems 630, 640 work as a stress-relief suspension, which not only holds the blood sac within the pump housing 62*h* but also avoids stress concentration to occur at interface attachment, hence prolonging the service life of the sac 629.

As shown in the bottom of FIG. 23A, the distal shell 625 includes an extension, termed distal shell adapter 6251, which is to be coupled with the aortic adapter 14. This distal shell adapter 6251 has a first end 6252 attached to the sac 629 and the second end 6253 featured like a beak to be coupled with the interface adapter 501 (depicted in FIGS. 18A and 18B). The first end 6252 of the adapter 6251 matches with the distal end of the sac 629 smoothly. The opposite second end 6253, however, is configured to be paired with the interface adapter 501, and the coupling design goal is to minimize the interface discontinuity to avert clot formation. The adapter 6251 has a flange structure

6254 which is disposed in the middle region of the distal shell adapter 6251, working as a lock element to be received by the interface adapter 501.

Figure 24:
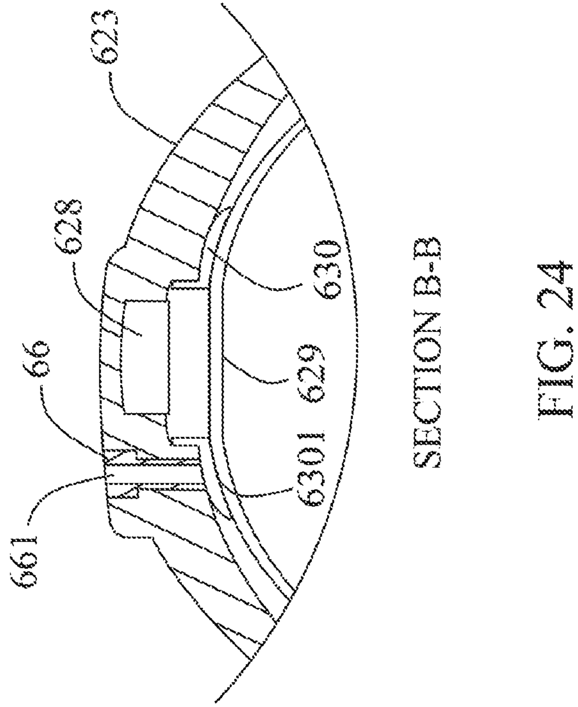
FIG. 24 shows a sectional view of a de-airing port installed in the proximal shell corresponding to the first embodiment.

During surgical operation, the closed-end sac design of the valveless blood pump 62 would attract air and agglomerate air bubbles in the sac top due to buoyancy force. As shown in FIGS. 22 and 24, a de-airing port 66 is hence installed or made in the proximal shell 623, in which a narrow channel 661 is provided above the stem 630. An integrated sac and stem septum 6301 as an extension from the channel 661 is used to allow de-airing needle to pierce through and enter into the blood chamber for air removal. In some embodiments, the channel 661 is extends alongside the centerline 62C. After the blood pump 62 is anastomosed with the target artery 60, the trapped air will be pushed by the arterial blood pressure and emerges and aggregates over the dome space of the sac 629. A thin needle is used to piece through the de-airing port 66, across the channel 661, penetrating the sac and stem septum 6301, and finally reaches the interior of the blood sac 629 to discharge the accumulated air. The integrated sac and stem septum 6301 beneath the de-airing port 66 is relatively rigid and non-flexing, which will maintain the pierced sac 629 without further structural failure due to crack propagation initiated at the pierced slit when subject to cyclic pulse pressure and the neighboring sac stretching and folding.

Figure 25A:
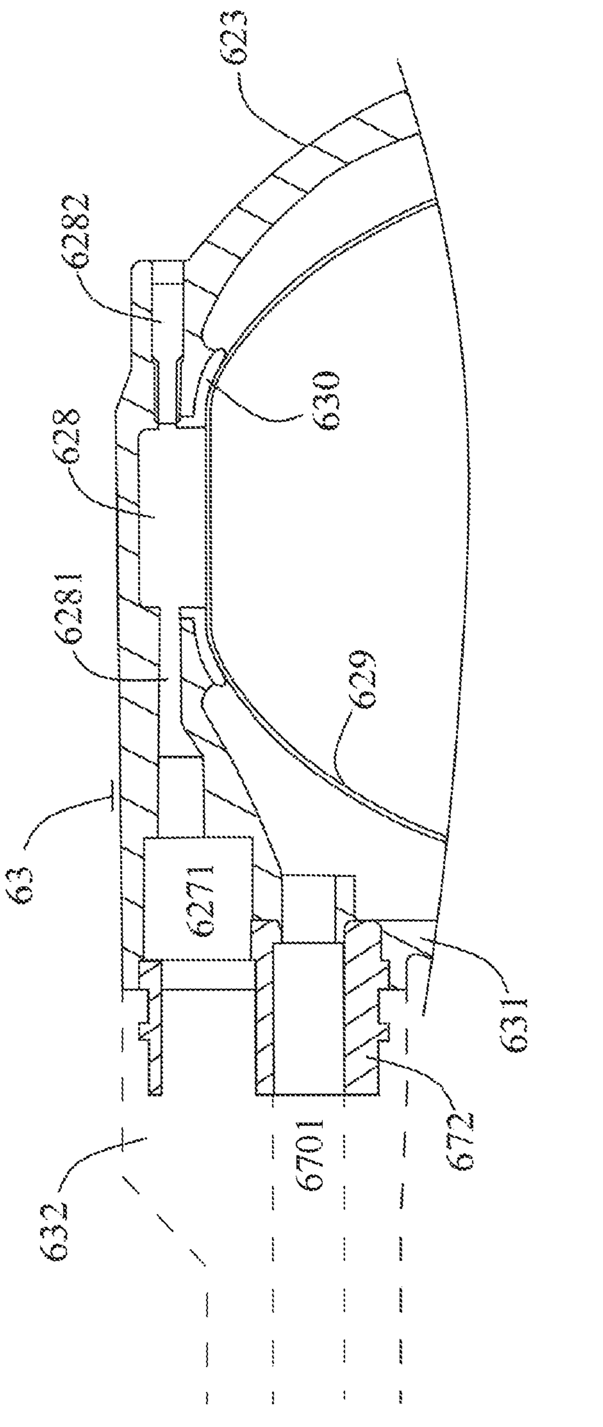
FIG. 25A shows a sectional view of a pressure sensing chamber and a feedthrough in the proximal shell of the first embodiment. Note that the driveline is not mounted and the feedthrough comprises a first portion, an extension of the proximal shell, and a second portion that is interlocked with the first portion.

As illustrated in FIGS. 23A and 25A, the pressure sensing mechanism 627 is embedded in the proximal shell 623. FIG. 23A illustrates the sectional details of an integrated proximal shell 623, feedthrough 63, and driveline 67. FIG. 25A depicts the profile of the proximal shell 623 that connects a feedthrough 63 extended from the dome of the shell 623 for pneumatic and signal communication with the driveline 67.

Figure 25B:
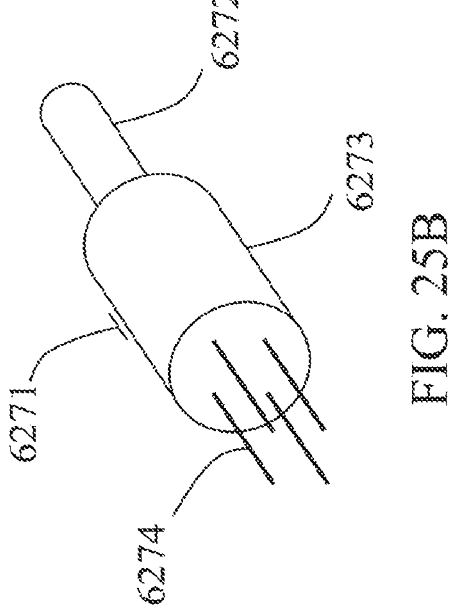
FIG. 25B shows a perspective view of a micro electro-mechanical system (MEMS) pressure sensor incorporated in FIG. 25A.
Figure 26:
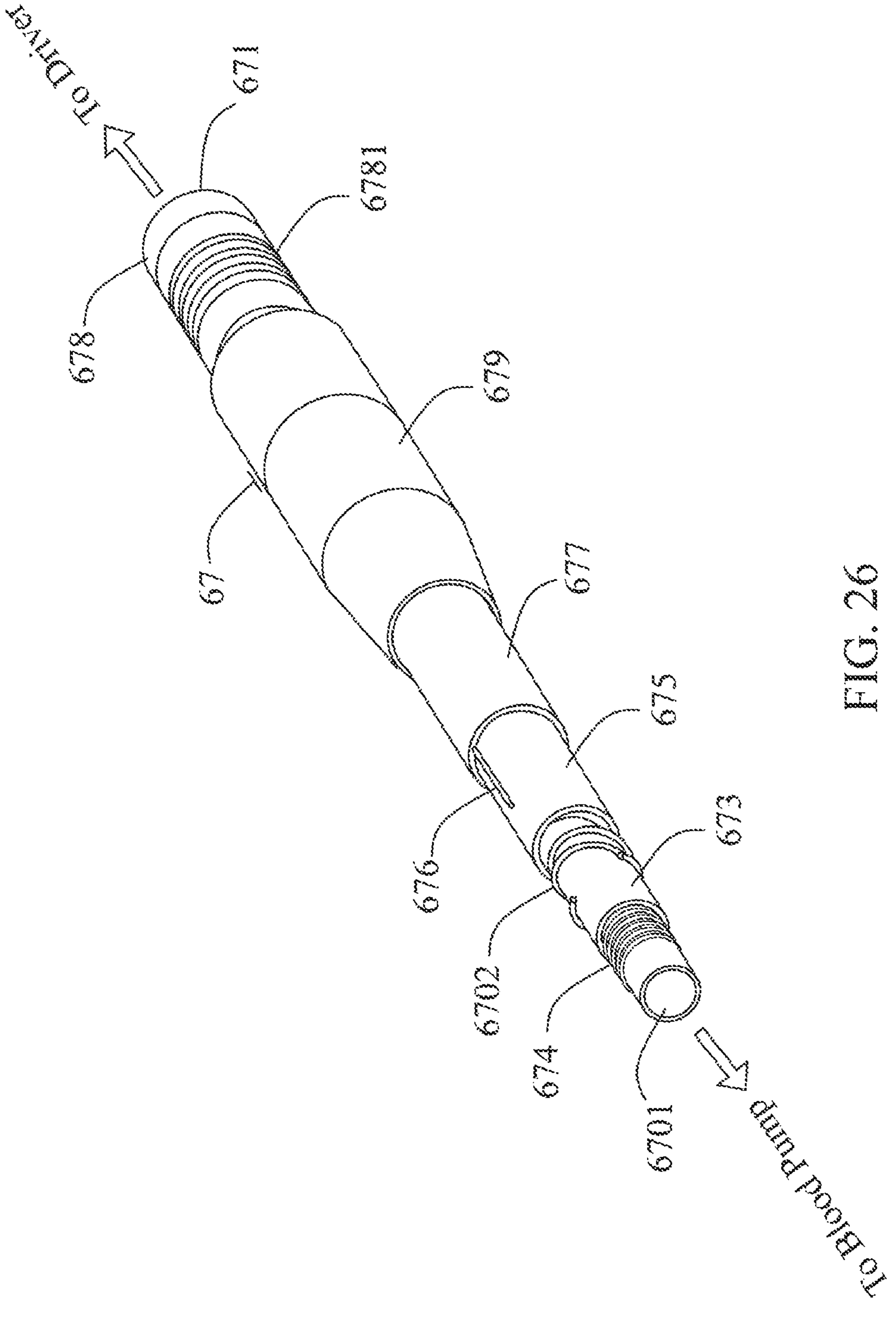
FIG. 26 shows a perspective view of a multi-layered driveline of the present invention, in which inner tubing for pneumatic air transport, middle tubing for electric signal transduction as well as coils, tethers and outer tubing are included.

The pressure sensing mechanism 627, as detailed in FIGS. 25A and 25B, has a pressure sensor 6271, which is hermetically housed in a metal canister, including a first space 6272 for fluid communication and a second space 6273 for accommodating the micro electro-mechanical system (MEMS) pressure transducer and the associated electronic circuit. There are multiple electrodes 6274 stuck out from the base of the second space 6273, to be connected with the electric wires 6702 of the driveline 67 (FIG. 26). The second space 6273 is closer to the driveline 67 than the first space 6272. The small tube of the first space 6272 is open to fluid communicate with the sensing medium. Biocompatible fluid or jelly is used as the pressure transmission medium. A cavity or a pressure sensing chamber 628, situated in the proximal shell 623 and adjacent to the first space 6272, is created to allow sensing fluid be enclosed in. This pressure sensing chamber 628 has a distal end separated with the blood chamber by the sac membrane 629. The pressure sensing chamber has two side arms: first arm 6281 and second arm 6282, wherein the arm 6281 is used for installation of pressure sensor 6271, and the arm 6282 is used for filling and sealing a sensing medium. The blood pressure pulse, hence, can be transmitted across the sac membrane 629 and hydraulically communicated with the MEMS sensor 6271 remotely located in the second space 6273.

An embodiment of the present invention innovates a pressure-based blood pump control method and sensor design. A miniature MEMS pressure sensor is adopted with electronic circuit packaged and embedded in the pump housing wall. In principle, MEMS sensor die is very durable owing to its intrinsic micro-scaled structure. Sensor durability, in fact, depends on the packaging design. The present pressure sensing system 627 is non-blood contacting and isolated from the corrosive biochemical effects associated with blood, thus providing long-duration signal acquisition and transmission that is required for long-term implantable assist devices.

The driveline 67 works as a communicator for electric signal transduction and pneumatic pulse pressure transfer between the blood pump 62 and the driver 98. A representative multi-layered driveline 67 in the present invention is shown in FIG. 26. In this embodiment, the driveline 67 has a pneumatic lumen (or inner pneumatic tubing) 6701, a plurality of electric wires 6702, a middle pneumatic tubing 673, a coil 674 (such as a metallic coil), an outer layer tubing 675, a tether 676, a silicone jacket 677, a rigid driver connector 678, and a protective bend relief 679.

Figure 27:
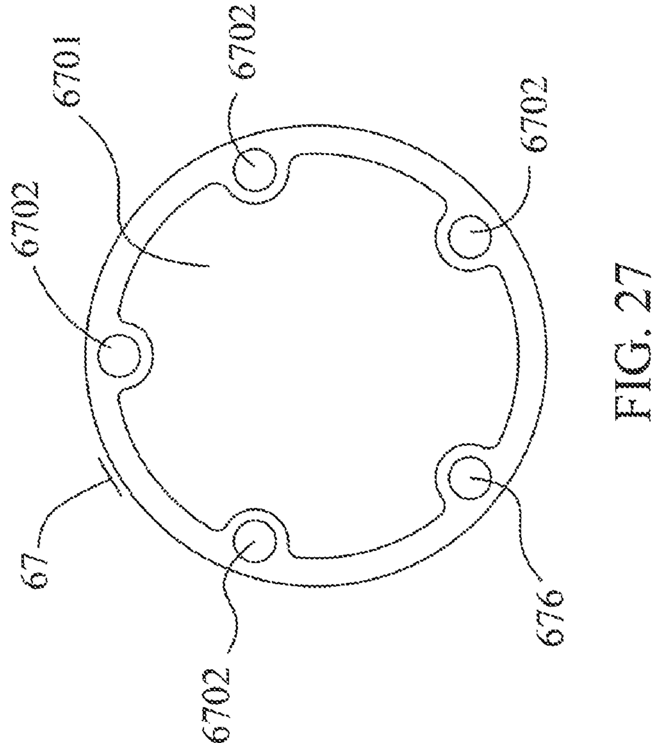
FIG. 27 shows a cross-sectional view of a multi-luminal driveline design option of the driveline.

The central portion of the driveline 67 accommodates the pneumatic lumen 6701 (or air passage, inner tubing) with a lumen diameter around 2-5 mm, depending on the preference of choice between lower energy consumption or low-profile for easiness of surgery. The electric wires 6702 for signal transmission are embedded in the wall of the driveline 67. There are variants of driveline design that may be adopted. Aside from the multi-layered driveline design shown in FIG. 26, the driveline 67, for instance, can also be multi-luminal to facilitate electric wires 6702 embedment in several smaller lumens and allow pulsed air to flow in a larger lumen 6701, as shown in FIG. 27. One of the smaller lumens can be installed with tether 676 so as to limit the stretching of the driveline 67 and protect the electric wires from damage when subject to the pull force of externalization.

The inner tubing, or pneumatic lumen 6701, is received by the middle tubing 673 with reinforcement being sandwiched in between. Between the inner and middle tubing 6701 and 673, the coil 674 (or fabric thread or mesh) can be reflowed (thermally co-molded using heat shrink) as a reinforcement to the driveline wall, making the driveline 67 flexible but kink resistant. The outer layer tubing 675 covers the inner and middle pneumatic tubing 6701 and 673, and can be employed to cover the spirally wrapped electric wires 6702 as a protective sheath. In some embodiments, a non-distensible tether 676 can be disposed between the outer tubing 675 and the silicone jacket 677 of the driveline 67, to strengthen the tensile resilience required during externalization of the driveline 67. Clinically it has been demonstrated that silicone jacket 677 is least irritative to the subcutaneous tissues and has the lowest driveline infection rate.

In this embodiment, the pneumatic lumen 6701, the metal coil 674, the middle tubing 673, the spiral electric wires 6702, the outer tubing 675, the tether 676, and the silicone jacket 677 are packaged into a body of the driveline 67. The proximal end 671 of the driveline 67 is to be plugged into a receptacle housed in the driver 98. The rigid driveline connector 678 of the driveline 67 is configured to be received by the receptacle of the proximal driveline interconnector 93 or the driver 98. The rigid driver connector 678 is flush mounted with a plurality of electrodes 6781 (for example, four electrodes 6781 in FIG. 23B) soldered with the electric wires 6702. A protective bend relief 679 (see FIGS. 23B and 26) is placed over the joint segment of the driveline 67 and the driver connector 678, in order to keep the driveline 67 from being kinked at the joint. The proximal end of the driveline, including the driver connector 678 and the bend relief 679, is kept in low-profile so that it is easy to exit the skin without creating undesirable tunneling trauma.

The connection of the driveline 67 onto the blood pump 62 is accomplished via a feedthrough 63, as illustrated in FIGS. 22, and 23A. The feedthrough 63 can be placed in the proximal shell 623 or in the distal shell 625, depending on the anatomy where the blood pump 62 is to be implanted. Integrating feedthrough 63 with pump housing **62*h* may change the overall outer blood pump configuration and direct the driveline 67** in certain direction to meet the implant requirements including driveline externalization route, post-operative skin care and device usability.

As shown in FIGS. 23A, and 25A, the feedthrough 63 has a first portion 631 as an extension of the proximal shell 623 in which the pneumatic lumen 6701, the tether 676 and the electric wires 6702 of the driveline 67 are coupled via an anchor adapter 672, wherein the anchor adapter 672 connects with the distal driveline 67 to allow driving air to pass through the pneumatic lumen 6701. The feedthrough 63 further has a second portion 632 which is interlocked with the first portion 631 working as a bend relief of the driveline 67. The first portion 631 is the location where electric wire connection, tether anchorage, and pneumatic lumen bonding and seal with the housing take place. It is required that electric wires must not be exposed to implant site tissue and have to be well protected against pull force exerted during driveline externalization. Also, the connection of pneumatic lumen 6701 with blood pump 62 need to be pneumatically and electrically leakage-free. As shown in FIG. 25A, these mentioned blood pump integration tasks are performed in the first portion 631. The second portion 632, however, is employed to accommodate and seal these interface joint elements, working as an outer protector that protects the joint from mechanical straining and environmental fluid or moisture invasion.

The modular design pertaining to the first embodiment of the present blood pump invention has been disclosed in FIGS. 19 to 27. In this illustrated embodiment, the blood pump 62 includes an axi-symmetric oval-shaped blood sac and stem assembly 650 (including a flexible membrane sac 629, a proximal stem 630 and a distal stem 640); a pump housing **62*h* having a proximal shell 623 and a distal shell 625; and a pressure sensing system 627 embedded in the proximal shell 623. A driveline 67 is connected to the blood pump 62, including a pneumatic lumen 6701 and electric wires 6702 included in the wall thereof. To integrate the driveline 67 with the pump housing 62*h*, a feedthrough 63 is used to accomplish both electric and pneumatic communication between the driveline 67 and the blood pump 62**.

As shown in FIGS. 19 and 20, the polymeric manufacturing and bonding method integrating together the blood sac 629 and stems 630, 640 has been disclosed in the previous section. The design and manufacturing essentials lie in maintaining a high-precision axi-symmetry in parts manufacturing and bonding of the sac and stem assembly. The pressure sensing system 627 and the feedthrough 63 are installed in the rigid part of the proximal shell 623. As shown in FIGS. 22, 23A, and 25A, a compact feedthrough 63 design is illustrated. It can be observed that, by the compact feedthrough 63, the electric wiring and connection can be achieved more robust and fault tolerant.

Figure 28A:
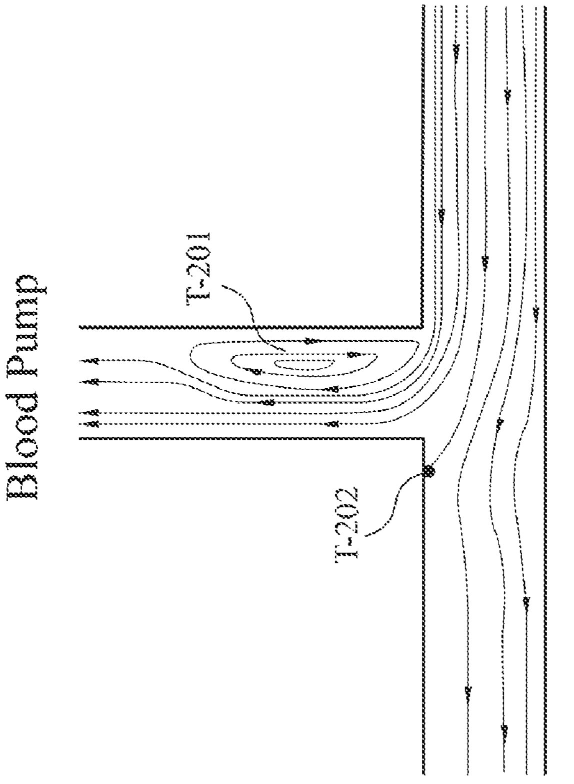
FIG. 28A shows a typical view of flow characteristics in the pump filling phase.
Figure 28B:
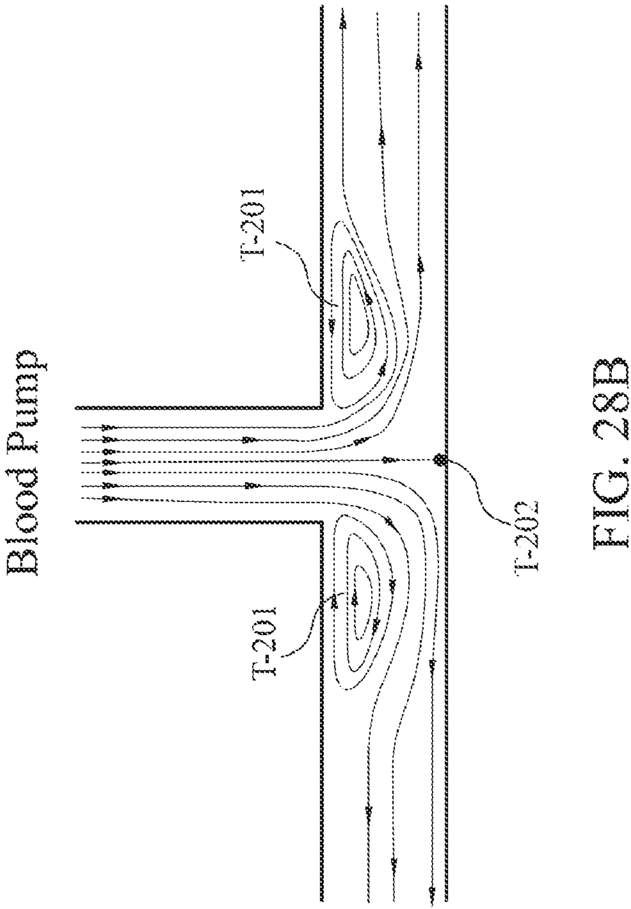
FIG. 28B shows a typical view of flow characteristics in the pump ejection phase.

FIGS. 28A and 28B depict some flow patterns associated with para-aortic counterpulsation. Over end-diastolic and early systolic phase of left ventricular ejection, the blood pump undergoes pump fill and draw aortic flow into the pump (FIG. 28A). Both upstream and downstream blood around the connector will be sucked into blood pump by making a sharp 90 degrees flow turn. Flow separation and low-speed recirculation zones T-201 hence will be created. Also, extraordinarily high-shear will appear at the corner region of the T-junction. On the other hand, during diastolic phase after aortic valve closure, the stored blood in the pump will be ejected back into the circulation, creating impinging flow on the opposite aortic wall (FIG. 28B). This side dump, impinging flow involves very high local pressure at the impingement point T-202, the so-called stagnation point where flow speed is literally zero and all kinetic energy associated with flow velocity is converted into a potential energy termed total pressure. Such high-pressure impinging flow may induce vascular maladaptation including smooth muscle cell proliferation and the resultant wall stenosis, and risk of aortic dissection due to persistent local hypertension. All these non-physiologic flow pattern and the induced high-pressure, high-shear, low-speed recirculation phenomena prevail in the vicinity of the T-juncture region. This turbulent, complex flow anomaly will decay or diminish in a distance of 3-5 times the implanted arterial lumen diameter. The present insertion type aortic adapter is designed to have an inserted conduit length of 5-7 cm, which covers most of the pump-induced non-physiologic flow region. As the implant site aorta is shielded by the inserted aortic adapter, the biologic vascular wall will be isolated from the influences of the pump-induced pathological stress conditions, hence protecting the implant site artery from remodeling complications induced in the acute or long-term period.

In counterpulsatile support, pump fill and ejection are alternatingly actuated in synchronization with cardiac rhythm, which generates a special T-juncture flow as shown in FIGS. 28A and 28B. This insertion type aortic adapter 14 is further detailed in FIG. 29, a perspective view, and in FIG. 30, a sectional view, respectively.

The aortic adapter 14 is mold injected with its internal blood-contacting surface 141 being manufactured ultra-smooth and continuous without any parting lines. Silicone or other polymeric elastomers can be used as the material. The aortic adapter 14 comprises a conduit (or an inserted conduit portion) 142 which is to be inserted in the aorta 95 (see FIG. 5) and a neck (or an extruded neck portion) 143 that connects to the blood pump. In this embodiment, the neck portion 143 has a neck body 1431 and an extension part 1432 disposed on the neck body 1431, wherein the extension part 1432 protrudes from the neck body 1431, and the maximum inner diameter of the extension part 1432 is larger than the maximum inner diameter of the neck body 1431. When the neck portion 142 is connected to the blood pump 62, the extension part 1432 snuggly embraces the inlet adapter 6251 of the blood bump 62, and the neck body 1431 is disposed around by the coupler 25 which integrates the aortic adapter 6251 to the blood pump 62.

The entire aortic adapter 14 is thin-walled to maximize the flow efficiency. To strengthen the thin-walled structure, a pair of Nitinol truss (or truss rings) 144 is embedded around the two ends of the conduit portion 142 of the aortic adapter 14.

Figure 29:
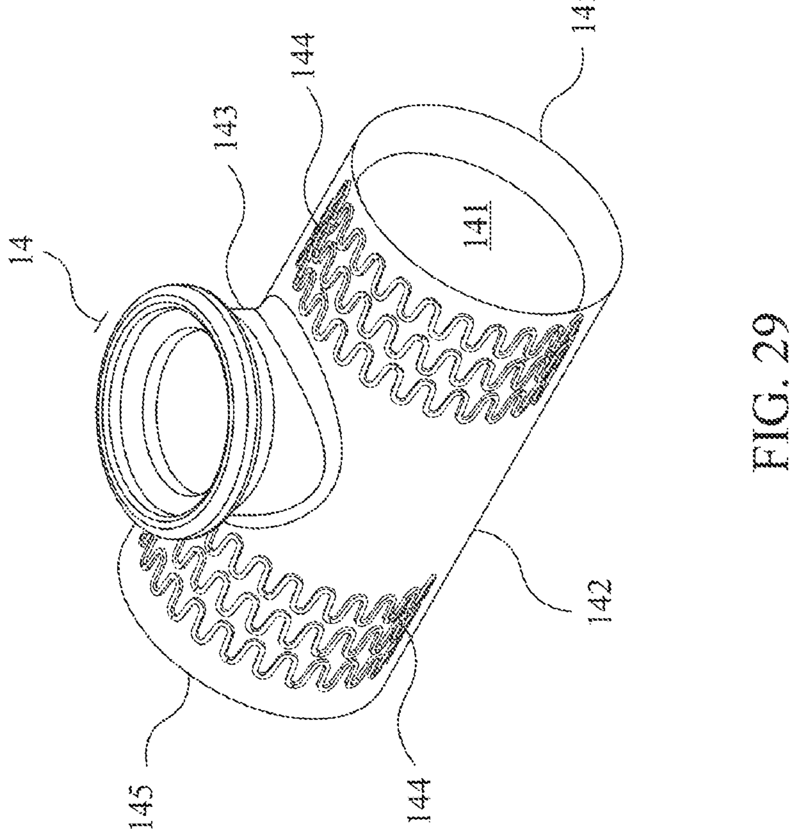
FIG. 29 is a perspective view of the present embodiment of the T-shaped aortic adapter.

FIG. 29 is a transparent view showing the locations where the Nitinol truss 144 is embedded. Further, the wall thickness of the conduit 142 is gradually thinning toward the conduit end 145. The function of the gradually thinning wall thickness is two-fold. First, it minimizes the graft/host junction discontinuity and renders the interface clot formation rate always be lower than the thrombolysis rate provided by the contacted endothelium. Second, the compliance of the conduit is becoming softer toward the conduit ends 145, resulting in a compliance-matching effect when joined with the aortic lumen.

One of the complications that plagued the large stent graft implantation is the endo-leak problem. Type-I endo-leak means the seal of the graft end to the endothelial lumen of the implanted artery is not complete, causing gap created between the graft leading-edge and the arterial lumen. Leaked blood will be trapped and jammed in the gaps and solidified into clot and finally becomes fibrous pseudo-intima which will grow uncontrollably in time. Not only the pseudo-intima will obstruct the grafted artery, but also it may signal and stimulate coagulation mechanism to attract platelet adhesion and leads to thrombotic adverse events to occur. The solution to resolve such endo-leak problem is to have a tight seal of the aortic adapter 14 with respect to the attached lumen surface. The present aortic adapter 14 comes up with a compliance-matching design concept that enables the semi-rigid conduit ends 145 seamlessly attach to the arterial lumen when subject to pulsatile blood pressurization. The outside diameter 146 of the aortic adapter conduit 142 is slightly larger than the luminal diameter with an oversize ratio (defined as percentage increment in conduit diameter 146 relative to luminal diameter) in the range of 3-10% conditioned at certain nominal blood pressure (say 120 mmHg). As blood pressure fluctuates between systole and diastole, or under the pulse pressure generated by counterpulsatile support, the compliance-matching conduit ends 145 will dynamically expand and contract in response to the pressure pulsation without creating interfacial gaps.

Figure 30:
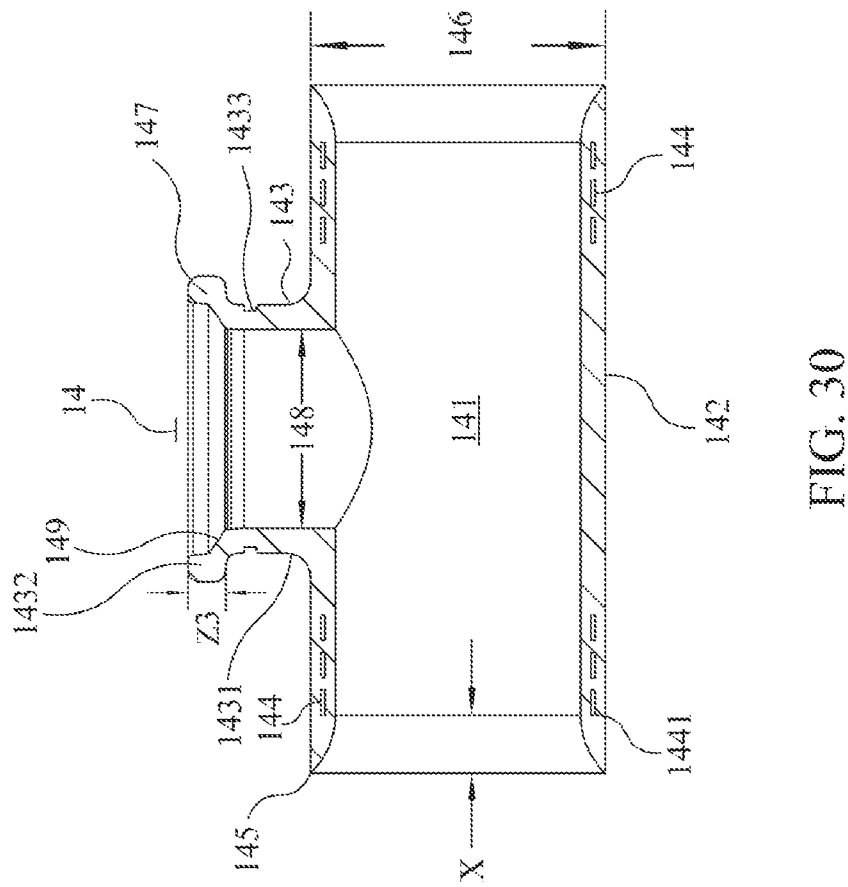
FIG. 30 is a sectional view of the present embodiment of the T-shaped aortic adapter.

Generally speaking, a thin-walled tubing made of elastomer is flexible and tends to be compliance-matching, but it is often not strong enough to withstand the compression force exerted due to device oversizing, causing wall buckling of the inserted adapter and the resultant massive bleeding. Hence, the combined use of Nitinol truss structure 144 and the elastomeric substrate with appropriate hardness is important. As shown in FIG. 30, in this design, the radial stiffness provided by the Nitinol truss 144 will help support the aortic adapter 14 without buckling, and there is a distance "X" between the outmost boundary 1441 of the truss 144 and the conduit end 145. In some embodiments, this distance X should be assessed and correctly defined. With the support of the Nitinol truss 144 as a distensible frame, the gradually thinning conduit end 145 will not collapse or wrinkle, which remains in circular shape against the attached lumen wall and dynamically seals with the lumen. Notice that the aortic adapter 14 can expand and contract in response to the pressure pulsation, and the seal effect is accomplished in a dynamic manner that the aortic adapter 14 and the wall of the aorta 95 expand and contract together as a whole to seal the conduit end 145 without causing bleeding complication.

Figure 31:
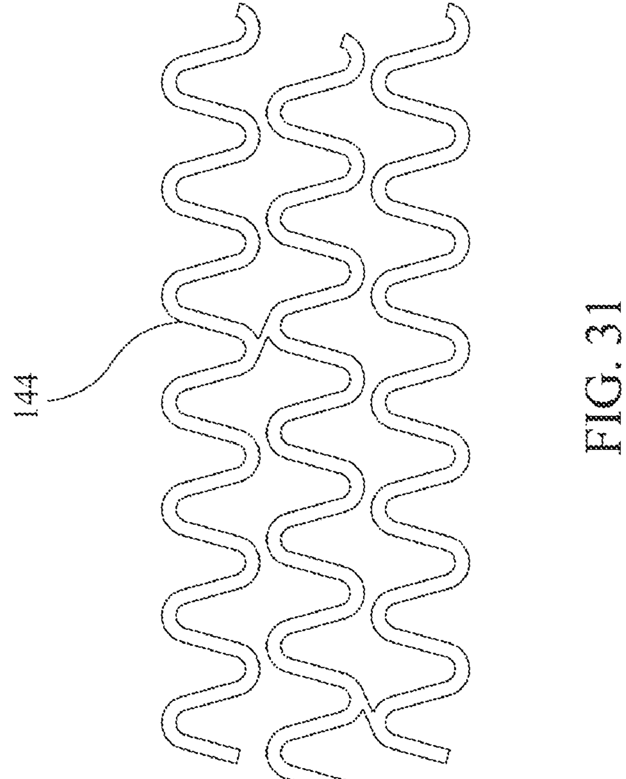
FIG. 31 is an expanded two-dimensional illustration of the embedded Nitinol truss.

Illustrated in FIG. 31 is a representative embodiment of the Nitinol truss 144 which is typically made from a laser-carved Nitinol tube further enlarged under a sequence of expansion and a heat treatment. FIG. 31 shows the two-dimensional expanded view of the truss ring 144. Each truss has a plurality of wavy structures 1441. The truss 144 is self-expandable, which can be folded or crimped into a smaller prepacked delivery configuration and expands to resume its original configuration when released after being placed at the desired location.

Figure 32:
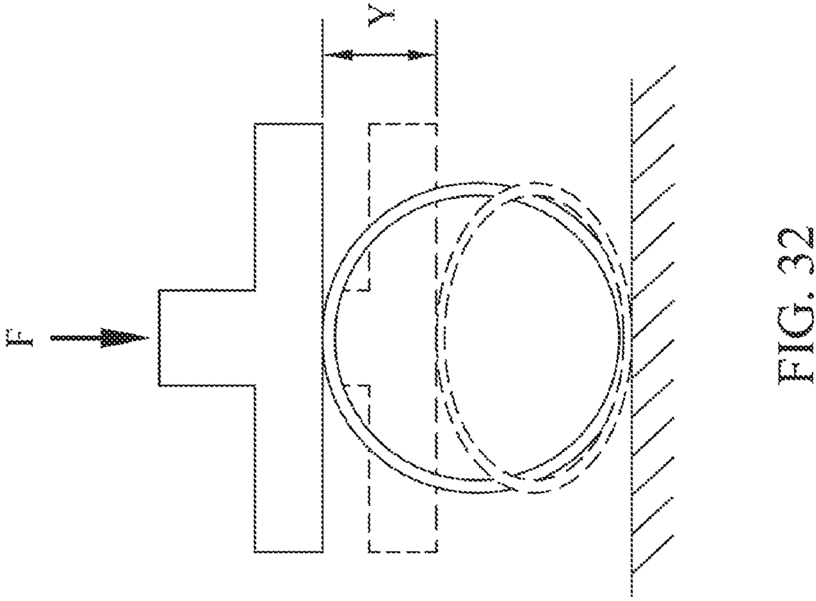
FIG. 32 defines the lateral stiffness (LS) used in the measurement of Nitinol truss embedded conduit of the T-shaped aortic adapter.

A convenient measure of conduit rigidity (inverse of compliance) can be represented by the so-called lateral stiffness (LS) whose measurement method is illustrated in FIG. 32. LS is defined by the applied force per unit length F divided by the corresponding radial deflection Y. For the present aortic adapter, suitable LS range is 0.01-0.05 Nt/mm2. Both embedded Nitinol truss 144 and silicone or elastomer substrate will contribute the structural compliance to the co-injected aortic adapter 14. It is best to have an equally distributed compliance so that the stretch and contraction of the composite conduit wall will result in a minimal interlayer delamination tendency to increase the fatigue life of the adapter 14.

Figure 33:
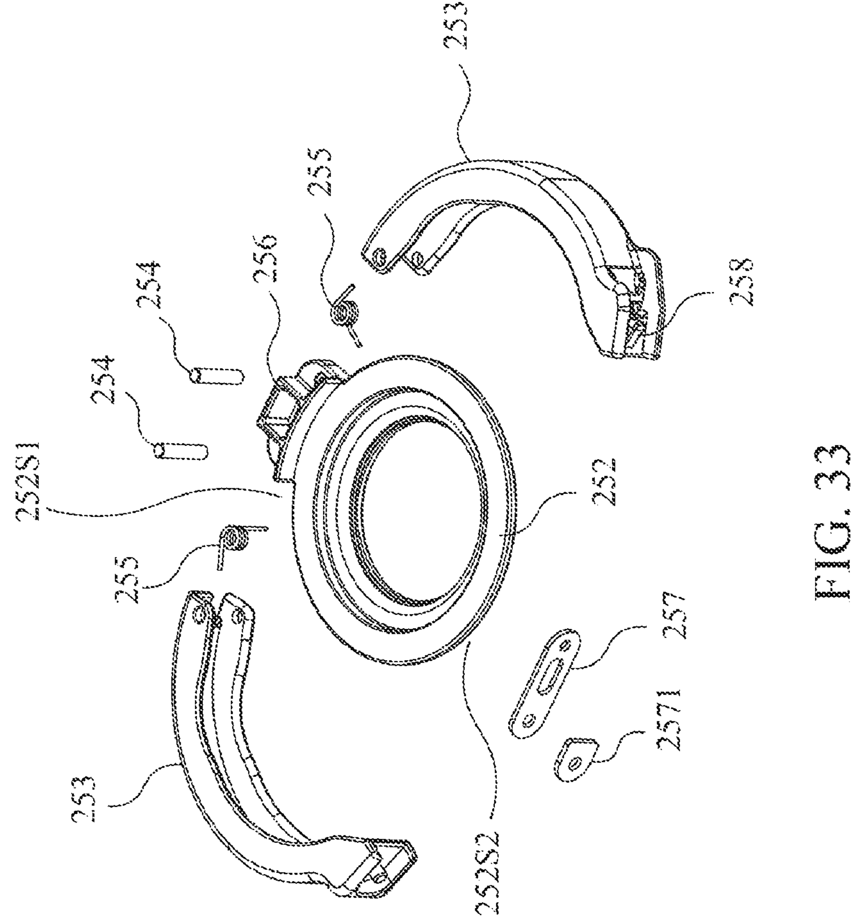
FIG. 33 shows an exploded view of the parts included in the coupler.
Figure 34A:
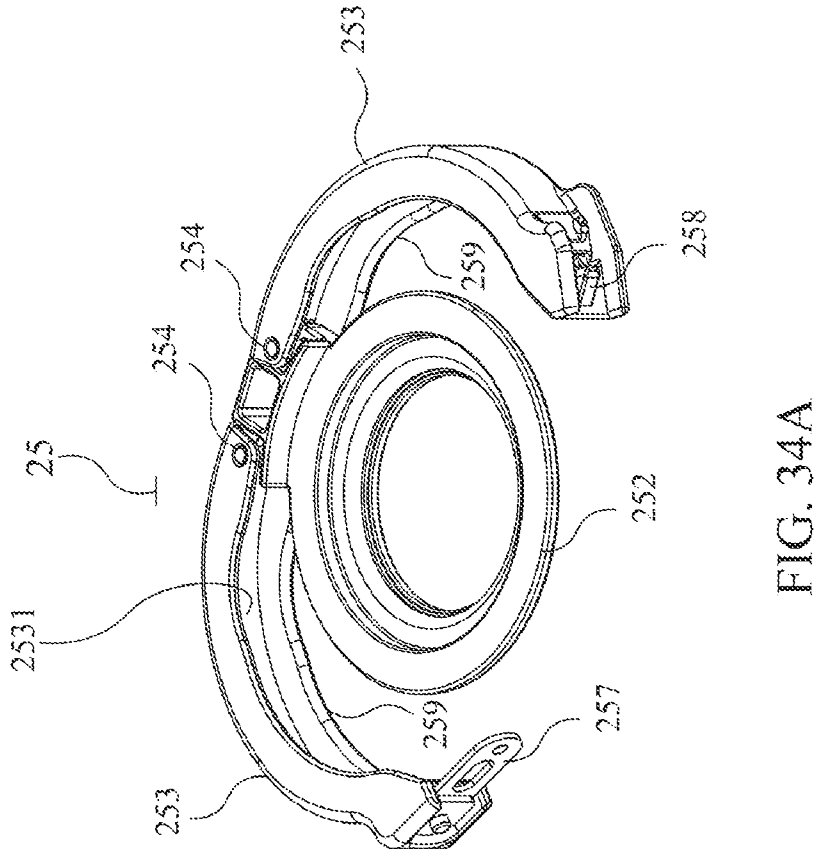
FIG. 34A shows an integrated view of coupler in the open configuration.

The aortic adapter 14 is configured to be connected to the blood pump 62 to facilitate circulatory support. A quick-connector type coupler is invented herein. Illustrated in FIG. 33 are the exploded view of the components of the coupler 25 that integrate together the aortic adapter 14 and the blood pump 62. The present coupler 25 includes a flange base 252, a pair of collars 253, and hinges (or a hinge assembly) 254 that join together the collars 253 with the flange base 252. Spring coils (or a spring coil assembly) 255 are loaded in a hinge joint 256, maintaining the collars 253 in an open position when unlocked (FIG. 34A). The locking mechanism is a latch 257, made of slotted leaf spring and fixed by a slab 2571 welded to one of the ends of the collars 253. The flange base 252 has a substantially circular-shaped structure, and each collar 253 has an arc-shaped structure. The hinge joint 256 is located at the first side 25251 of flange base 252, and the collars 253 are pivotally connected to the hinge joint 256 and rotatable to the hinge joint 256 and the flange base 252. In some embodiments, the coupler 25 and the aortic adapter 14 belong to portions of an aortic adapter assembly.

Figure 34B:
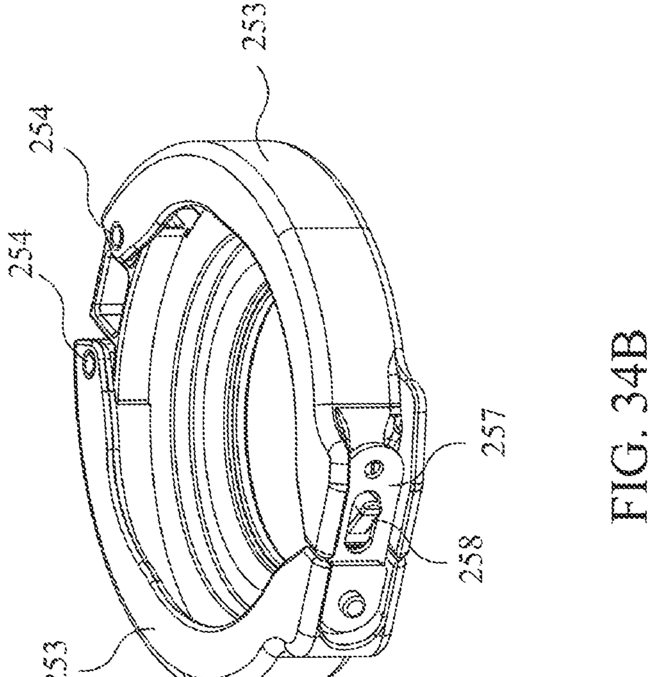
FIG. 34B shows an integrated view of coupler in the latched configuration.
Figure 35:
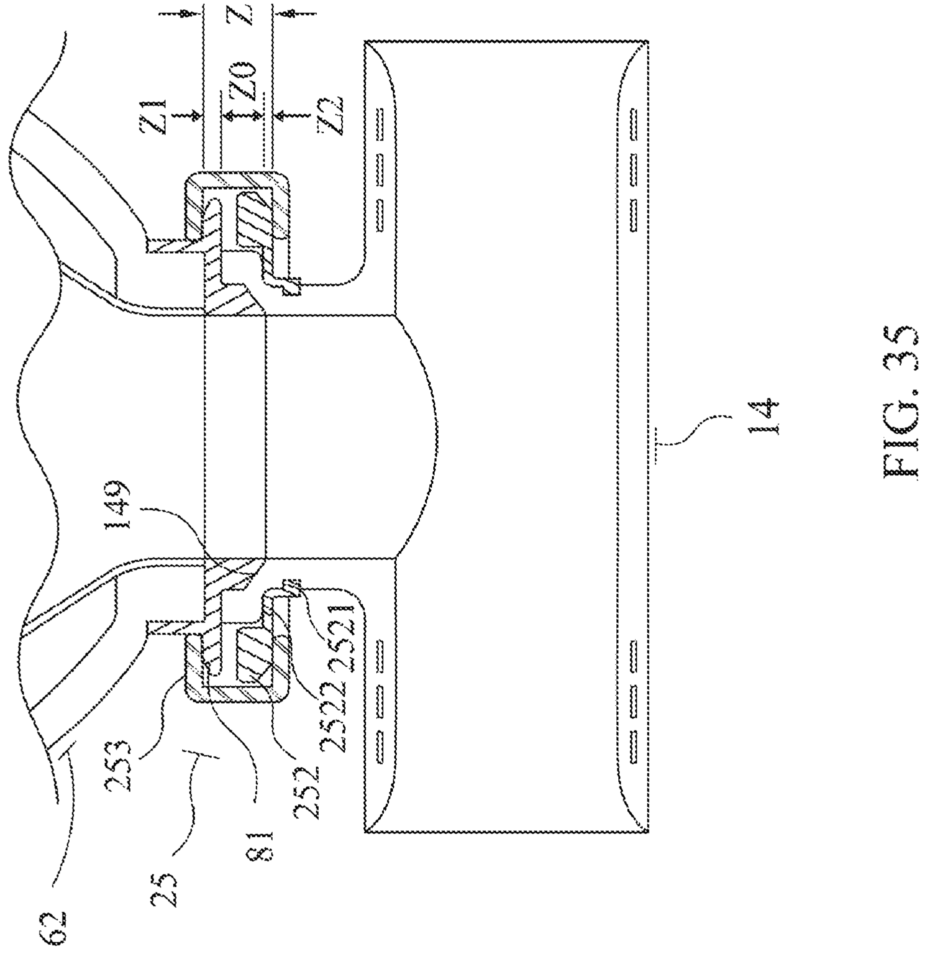
FIG. 35 is a sectional view of the aortic adapter integrated with a para-aortic blood pump using the coupler.

FIG. 34B shows the picture of the coupler 25 in locked configuration, in which a leaf spring latch 257 is dropped down from a ramp 258 to assure the coupling is safe without the concern of detachment. The collars 253 are grooved internally as shown in FIG. 35. Integration of aortic adapter 14 to the blood pump 62 is accomplished through a clamping mechanism using the deformable adapter proximal end 147 (FIG. 30) serving as a "gasket" between the connected rigid flanges 252, and 81 of the coupler 25 (see FIG. 35) and the blood pump inlet adapter 6251, respectively.

In particular, quick-connection type locking can easily be carried out by closing the collars 253 that will be latched without a concern of unintentional unlocking, as depicted in FIGS. 34B and 35. The leaf spring latch 257 is installed at the tip of one collar 253. During collar closing, this latch 257 will be bent as it slides on a ramp 258 on the opposing collar 253 in the course of locking. As the latch 257 clears the top of the ramp 258, it will drop down to the base of the ramp 258 by elastic restoring force, working as a safe for preventing incidental latch unlock or collar opening attributed to pump vibration or rocking in long-term use. For a pump explant or exchange that requires module decoupling, the latch 257 can be bent and lifted upward by a tool, permitting an unlocking force to be exerted to rotationally open the collars 253 and hence disengage the blood pump 62 from the aortic adapter 14.

A butt joint design is not feasible for connecting two smooth-surfaced tubing adapters in a blood stream. In most clinical applications, the connected graft is with rough surface to promote endothelialization so that tiny interface discontinuity in the blood stream will be "smoothed out" by the ingrown cells and proteins. The present aortic adapter 14 adopts smooth surface approach to avoid thrombotic adverse events to occur. The blood flow in the aortic adapter is bi-directional in response to the ejection and filling action of the counterpulsatile pumping, as depicted in FIGS. 28A and 28B. Such strong bi-directional flow and surface washing effect will easily dislodge any neon blood clot newly formed on the rough surface. Hence, smooth surface design is considered more suitable and safer for the present invention. The interface of two joined smooth surfaces in blood stream requires a careful mechanical and hemodynamic design to avert the thrombotic events to occur in situ. In the following, the rationale and design method associated with such a novel joint invention is disclosed.

Figure 36A:
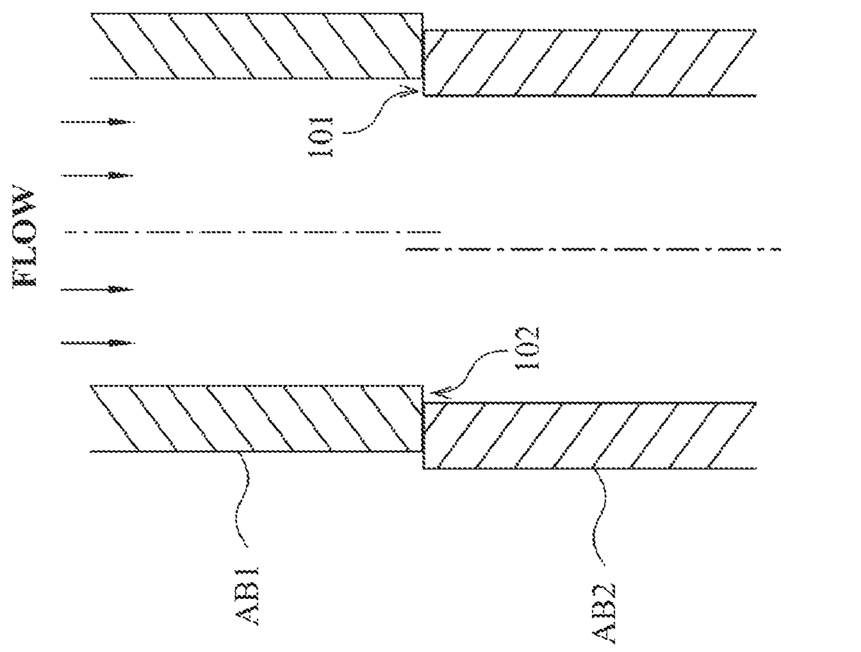
FIG. 36A depicts a step discontinuity generated by butt joint method.
Figure 36B:
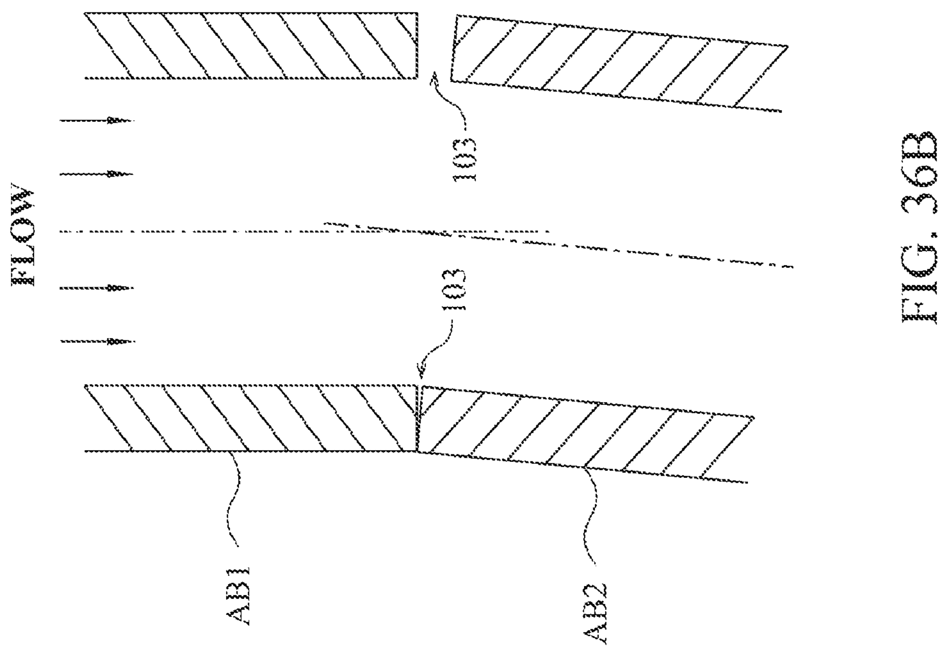
FIG. 36B depicts a gap discontinuity generated by butt joint method.

FIGS. 36A and 36B show respectively the two fundamental interface discontinuities that exist in a butt joint connection, such as the steps 101, 102 or the gap 103 produced between an adapter AB1 (such as an adapter 6251 of the blood bump 62) and an adapter AB2 (such as the aortic adapter 14). The discontinuities shown in FIGS. 36A and 36B are exaggerated and typically in precision machining such joint discontinuities are within 10-50 microns, which is big enough to cause clot and thrombus formation.

In practice, tolerance inevitably exists in matching two separate bodies even if the machining of each body is perfectly performed. FIG. 36A depicts a misaligned joint of two bodies, of which everything related to parts manufacturing is correctly done except the centerline misalignment. Forward-facing and backward-facing steps 101, 102 will be produced and the stagnation flow in the step regions 101, 102 is the origin that clot or thrombo-emboli will be generated. In FIG. 36B, an interface gap 103 is created due to non-parallel matching of the connected bodies. The gap 103 attracts blood cells to accumulate and further grow into pseudo-intima and such intima growth often is uncontrollable, resulting in blocking the entire blood flow passage in addition to the thrombo-emboli shed from the intimal surface. Interface errors associated with butt joint may exacerbate when the connected bodies are non-rigid. The present aortic adapter 14 is semi-rigid, which can be forced into butt joint connection with deformed configuration and enlarged interface discontinuities. Hence, to accomplish the present semi-rigid aortic adapter connection with blood pump, a novel connection method must be invented, as disclosed in the following.

Figure 37:
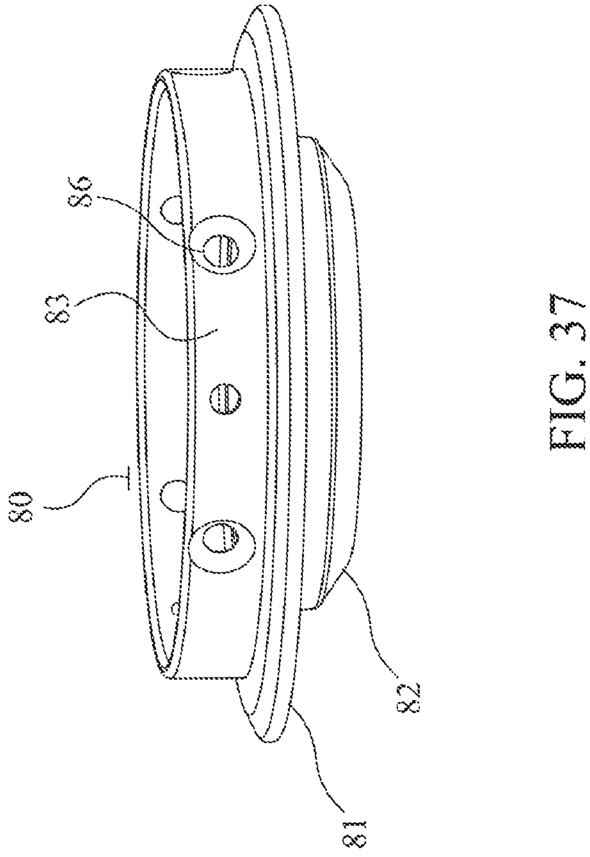
FIG. 37 shows a perspective view of an inlet adapter to be installed at the distal end of a para-aortic blood pump.
Figure 38:
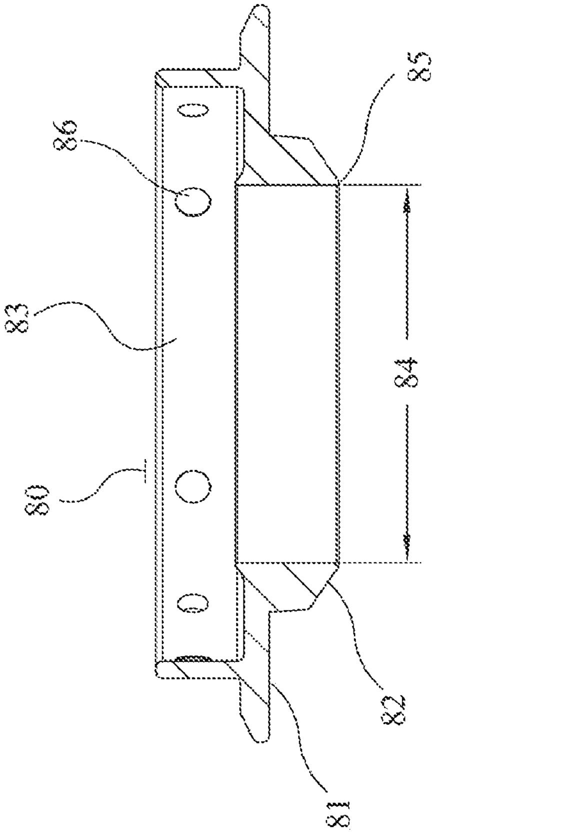
FIG. 38 shows a sectional view of an inlet adapter to be installed at the distal end of a para-aortic blood pump.

As shown in FIGS. 37 and 38, in some embodiments, the blood pump 62 has an inlet adapter 80, comprising a flange 81, a beak 82 and a base 83, forming an extension of the housing of the blood pump 62. Multiple eyelets 86 are equipped for joining the inlet adapter 80 with the blood pump 62.

The inner diameter 84 of the beak 82 is slightly greater than the inner diameter 148 (see FIG. 30) of the neck 143 of the aortic adapter 14. The contact area between the beak 82 and the adapter proximal end 147 is an annular cone surface (or a shallow inclined surface or ramp) 149 (FIGS. 30, and 35). The cone angle of the surface 149 is substantially in the range of 30-60 degrees measured from the centerline of revolution of the inlet adapter 80. In the initial locking engagement, the collars 253, which have inward grooves 2531 (FIG. 34A), will catch the flange of the base 252 and the beak flange 81 loosely. Along with collars 253 closing, the flanges 81, 252 (of the beak 82 and the coupler 25) will be received and squeezed by the collar grooves 2531, hence compressing the sandwiched silicone end 147, and generating the clamping force required for a firm connection.

The clamping force generation mechanism is graphically shown in FIG. 35. There are two steps 2521 and 2522 that are responsible for creating clamping forces. Prior to collar closing initiation, the step 2521 should be engaged in the slot 1433 of the aortic adapter neck 143 (FIG. 30). Such engagement is accomplished by folding the neck 143 first, and then insert the deformed neck 143 across the adapter flange 252, letting the elastic restoring force of the aortic adapter 14 to resume the folded neck 143 back to its original circular shape and allow the step 2521 be engaged into the slot 1433. The groove height Z of collar 143 controls the squeezed deformation of the aortic adapter end 147. Referring to FIG. 35 it can be found that the clearance Z0, in full locking configuration when collars 253 are closed and latched, is smaller than the aortic adapter end width Z3 (FIG. 30). Speculation of the assembled geometry shows that Z0=Z−Z1−Z2, wherein the Z1 and Z2 are the flange thicknesses of the clamped counterparts as shown in FIG. 35. In general, Z3 is greater than Z0, hence, the strained aortic adapter end 147 will generate clamping force required for a sealed connection of the beak flange 81 together with the collar flange base 252. The strain of the silicone flow adapter end 147, defined as (Z3−Z0)/Z3, in the range of 10-30%, suffices to guarantee a reliable sealed connection.

Figure 39:
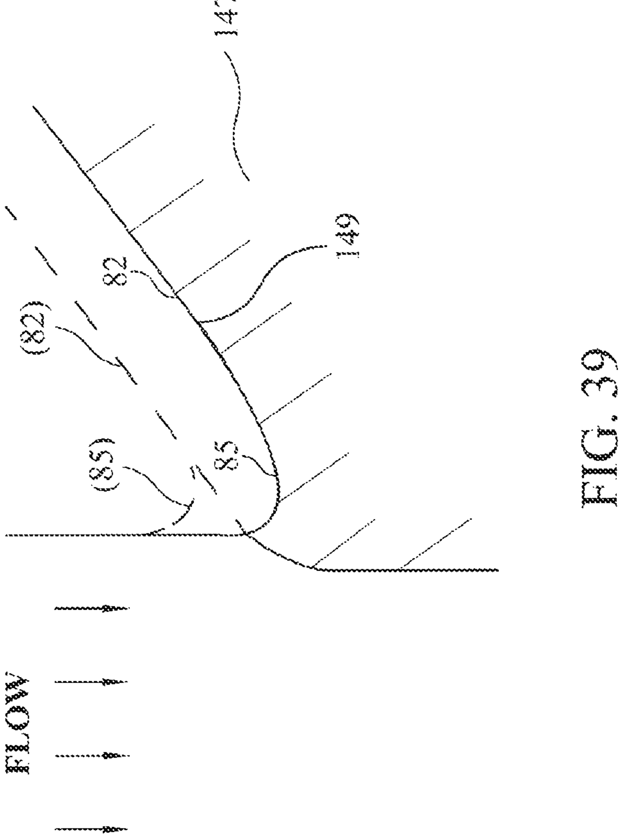
FIG. 39 shows a sunk beak of the inlet adapter as connected with the ramp surface at the neck of the T-shaped aortic adapter.

FIG. 39 illustrates the joint characteristic of the present connection of the beak 82 with the adapter cone surface 149. When connected, the beak leading edge 85 and the cone surface 82 will sink into the semi-rigid ramp surface 149 of the aortic adapter 14 with a depth comparable to the leading-edge radius, typically 30-50 microns, of the beak leading edge 85. In FIG. 39, dotted line and number in parentheses represent the beak in initial contact while solid line and numbers without parentheses represent the locked relationship. Notice that the interface discontinuity is reduced by the cone surface depression from its original shape (the dotted line). The width of the collar groove 2531 controls the interference fit of the coupling. As previously explained, the elastic aortic adapter end 147 will be compressed approximately with an 10-30% strain to provide the required coupling force for a leak-free integration against pulsatile pumping.

The present design of interface connection between the blood pump 62 and the aortic adapter 14 has two hemodynamic merits for reducing thrombus formation in-situ. First, there will be literally no step or gap type joint discontinuities generated as observed in the conventional butt joint connection. Second, stasis flow located in the interface of the beak leading-edge 85 can be minimized. Hence, blood stream flowing over the connected interface will be maintained with high-speed, substantially improving the butt connection drawback, namely the forward-facing or backward-facing steps 101, 102 or the gap 103 created at the interface.

The present cone surface 149 is ramped with an inclination angle to the stream direction. Such ramp interface design averts step or gap be generated at joint due to limited manufacturing precision or matching eccentricity associated with conventional butt connection. Nevertheless, this shallow, cone-shaped ramp 149 has an intrinsic shortcoming in fulfilling a concentric centerline alignment of the joined counterparts. The present coupling of the aortic adapter 14 with the inlet beak 82 has no strict lateral constraint to assure coupling alignment. To connect a rigid beak 82 with a semi-rigid aortic adapter flange ramp 149 concentrically, a simultaneous catching of the collars around the entire peripheral rim of flange base 252 is critical. When a simultaneous catching/locking engagement fails to be accomplished, the initially caught adapter flange ramp 149 will be strained more than other free portion, creating a tendency to tilt or disposition the rest contact surface leading to an eccentric pump connection. Such an eccentric connection often is the causal factor that generates step or gap at the interface that induces thrombus formation. This drawback is remedied by having the flange contour 259 (FIG. 34A) of the distal flange of the collars 253 configured in such a way that the locking engagement simultaneously includes all circumferential contact areas. When locked, the contacted edge of the metallic beak 82 will sink slightly into the compressed silicone ramp 149 with controlled depth and further reduces the interface discontinuity when exposed to blood stream. Hence, the conventional interface thrombus can be substantially minimized or annihilated with a moderate administration of anticoagulant regimen.

Structural deformability and method of delivery involved in the present aortic adapter confers a special design feature of the present invention. Material elasticity consideration, in fact, need to be carefully incorporated in the present design. Surgically deliver an insertion type graft into aorta via incised aortic wall is challenging in the sense of peri-operative safety and long-term reliability. The material chosen for the present aortic adapter 14 should have a preset memorized shape. During device delivery, the adapter 14 is first crimped into a smaller delivery configuration, and such delivery configuration guarantees a quick and safe device implantation. After the crimped aortic adapter 14 is placed at the intended implant site, the delivery configuration shall be released to self-expand to its original memorized shape.

Prior to aortic adapter insertion a hole of diameter 12-14 mm ought to be made in the aortic wall. In making such an access hole, care must be taken to avoid making any cut edges that may become a crack initiation point when wall distension is required for device insertion. A side-biting aortic punch, as disclosed in U.S. patent application Ser. No. 17/034,036, is an ideal tool for making a large hole in the aorta. With one bite of punch a sound hole without any fractured edges can be made successfully.

Figure 40:
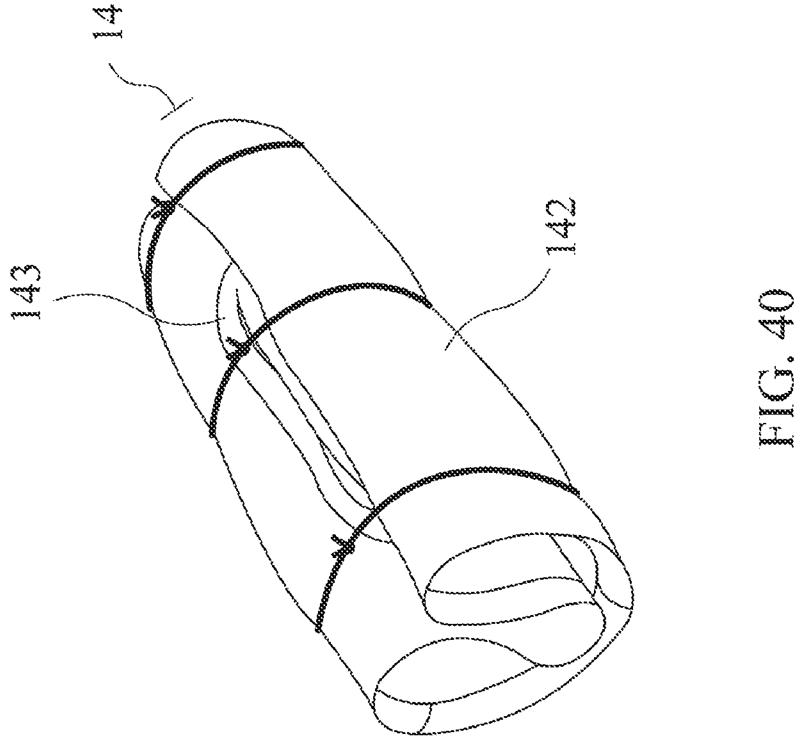
FIG. 40 depicts a perspective view of a crimped aortic adapter as packed into a delivery configuration by string constraints.

The aortic adapter 14 morphologically includes two circular tubes joined together into a T-shaped flow communicator for para-aortic circulatory support enforcement. The conduit wall is typically 1-2 mm in thickness and the material used is polymer such as silicone or polyurethane with appropriate hardness, for example, of Shore A 80-90. The crimped delivery configuration differs substantially from the commercially available large stent graft covered by Dacron or PTFE (Polytetrafluoroethylene) fabric. In FIG. 40 illustrated the crimped form of the aortic adapter 14 (Nitinol truss 144 is embedded and deformed with the polymer substrate). The aortic adapter 14 is folded by crushing the inserted conduit portion 142 and the T-neck (extruded neck portion) 143 is squeezed and flattened accordingly and sunk into the folded adapter 14 as shown in FIG. 40. Approximately, the folded configuration has a diameter roughly half of the original unfolded circular diameter.

Figure 41A:
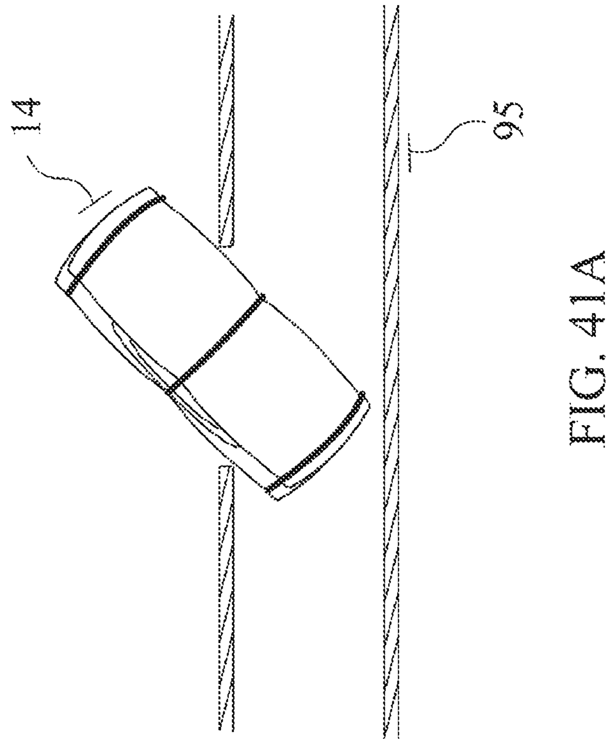
FIG. 41A depicts a packed aortic adapter being inserted half-way across an access hole made in the aortic wall.
Figure 41B:
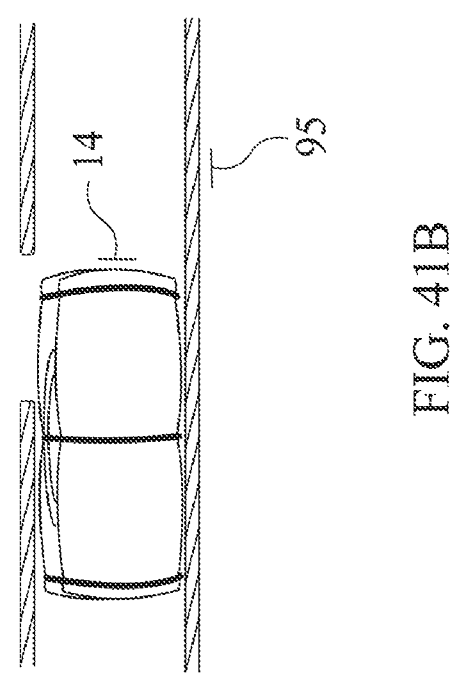
FIG. 41B depicts a packed aortic adapter inserted fully into aortic lumen.
Figure 41C:
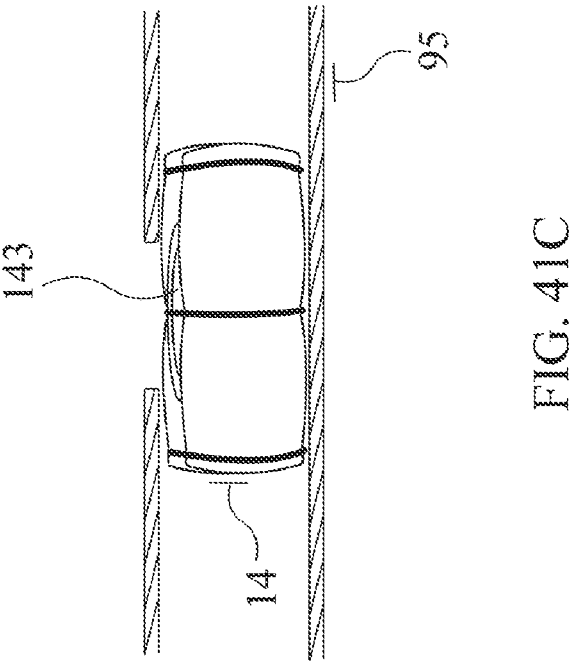
FIG. 41C depicts a packed aortic adapter repositioned with its T-neck facing the aortic access hole.
Figure 41D:
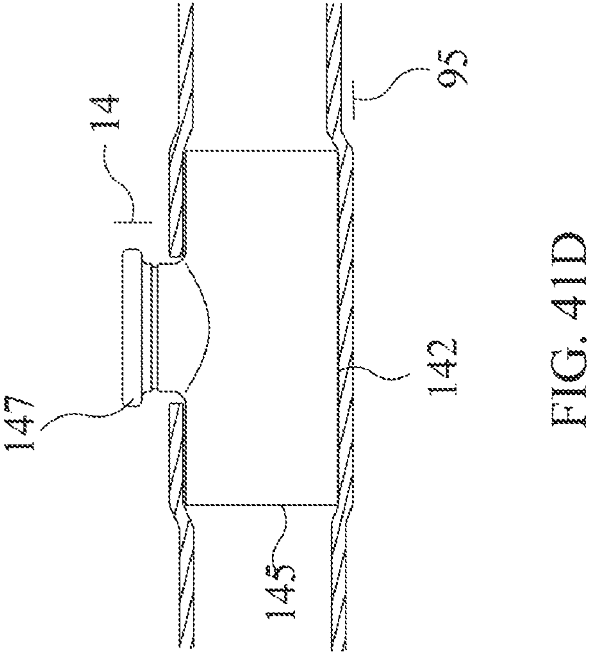
FIG. 41D depicts an expanded, deployed aortic adapter with its T-neck popped out of the aortic access hole after string release.

This folded adapter can be held fixed by string tightening. For example, as shown in FIG. 40, three fixation strings can be placed around the two edge and center of the conduit and many other fixation methods can be thought of. FIGS. 41A, 41B, 41C and 41D show the four representative stages of a delivery of the aortic adapter 14. The first stage (see FIG. 41A) depicts the initial penetration of the crimped prepack across the access hole while the prepack is inclined with an angle to the axis of the aorta 95. The second stage (FIG. 41B) illustrates the complete insertion of the delivery configuration into the aorta, where the prepack is pushed through the access hole with the proximal end being rotated and just dropped into the access hole. The completely inserted prepack is then retracted to have its crimped neck 143 aligned with the punched access hole (FIG. 41C). The string constraints will be released and the prepacked delivery configuration resumes back to its original deployed configuration by elastic self-expansion (FIG. 41D). The released aortic adapter 14 will snuggly be embraced by the aortic lumen, guaranteed by a proper oversize ratio selected prior to delivery. By slightly deforming the T-neck 143 the flange 252 of coupler 25 (FIGS. 33 to 34B) can be mounted onto the T-neck 143 ready for the blood pump 62 to be connected. The blood pump connection can therefore be easily accomplished by seating the inlet beak 82 onto the T-neck cone surface 149 followed by closing the two collars 253 of the coupler 25 for a firm device integration.

Additional safety measures can be applied to enhance the hemostasis and stability of the implanted para-aortic blood pump system. Para-aortic placement of blood pump inevitably involves lateral force (perpendicular to the longitudinal direction of the aorta) and torque exerted on the aortic adapter 14 due to the weight of blood pump 62 and the pumping forces generated by counterpulsatile support. Such device related external forcing may affect the long-term remodeling of the implant site vascular structure. A purse-string suture can be placed in the adventitial layer around the access hole. The purse-string suture can additionally tighten the aortic wall against the inserted adapter 14 and works as a protective measure to prevent the enlargement of the access hole. Moreover, surgical tapes can be looped and tightened around the two ends of the conduit 142, strengthening the integration of the inserted aortic adapter 14 and aorta as a whole. Freedom from endo-leak can be doubly assured by the compliance-matching design and the banding of the looped tapes. Sometimes, blood pressure may elevate beyond the upper bound that endo-leak free can be assured by compliance-matching. Under such extreme condition, surgical tapes come into play working as a hard limiter that seals the detached adapter ends and assures hemostasis be maintained.

The step-by-step demonstration of implanting the aortic adapter 14 is detailed in FIG. 42. A crimped prepack form is prepared prior to the start of implantation. After left thoracotomy to expose the target thoracic artery, a cross-clamping distance around 10 cm spanning the implant site is defined. The access hole to be punched in the aorta is first marked with hole periphery identified. A purse string suture is then sewn outside the hole periphery in the adventitial layer. The aorta can be partially dissected from the surrounding connective tissue and a pair of surgical tapes can be looped around the aorta. Cross-clamping and aortic adapter insertion is performed after the above preparation work is done. These insertion steps are described in a sequential order illustrated in FIG. 42. First, the aorta is cross clamped to provide an isolated segment without bleeding concern. Then, a large access hole for aortic adapter insertion is made using a custom aortic punch. The folded adapter prepack is then inserted and placed into the cross-clamped aortic segment as illustrated in FIGS. 41A, B, and C, followed by the release and restoration of the folded adapter to its original deployed form (FIG. 41D). Purse string and tapes are then tightened as an extra protection against endo-leak at hypertension. The coupler is then installed with its adapter flange 2521 seated into the slot 1433 of the aortic adapter neck, ready to receive the blood pump 22 to be connected. The self-alignment capability of the coupler design enables the beak 80 of the blood pump 62 be properly positioned and locked together with the aortic adapter 14. The rest implantation steps are conventional, including cross clamp release, blood pump deairing and the initiation of pump support. In general, for a trained surgeon, the cross-clamping period required for aortic adapter insertion is around 10 minutes. During this cross-clamping period the abdominal organs will be deprived of blood perfusion and ischemic injury could potentially be incurred. To mitigate this potential surgical insult to the organs, partial femoral-femoral extra-corporeal membrane oxygenation (ECMO) support can be administered to perfuse the abdominal organs and the lower limb. However, whether or not to employ ECMO support is to the discretion of the surgeon. Usually, an ischemic time of 20 minutes can be tolerated by a healthy patient.

In summary, an embodiment of the present invention provides a ventricular assist device, including a blood pump, a driveline and a feedthrough. The blood pump includes an axi-symmetric oval-shaped blood sac and stem assembly, including a flexible membrane sac, proximal stem, and a distal stem, wherein the flexible membrane sac is attached with the proximal stem and the distal stem as a stress-relief suspension mechanism; a pump housing, including a proximal shell and a distal shell, wherein the stress-relief suspension mechanism is coupled to the pump housing; and a pressure sensing system, embedded in the proximal shell, wherein the pressure sensing system includes a pressure sensor and a pressure sensing chamber which is filled with an incompressible fluid for pressure transmission. The driveline includes a pneumatic lumen, at least one electric wire and a tether, wherein the electric wires and the tether are disposed in the driveline wall. The feedthrough connects the driveline to the pump housing.

An embodiment of the present displacement pump invention discloses a pulsatile blood pump design that incorporates a non-stationary folding line concept in the construct of a long-duration blood sac that may substantially prolong the durability of a displacement type blood pump. Also, a miniature pressure sensing system is disclosed, which can be used to serve as reference waveform for real-time pump control as well as for long-term trending analysis, disease monitoring and diagnosis, based on evidence-based mega data. Further, the embedded pressure sensing system is non-blood contacting, which, hence, greatly improves the reliability requirements in building an implantable sensor system.

The embodiment of the present blood pump invention has at least one of the following advantages or effects. By the feedthrough connection of the driveline to the pump housing, a compact feedthrough design is provided to make the electric wiring and signal transduction more robust and fault tolerant. Further, a compact feedthrough design integrates the sensory electric wires and the pneumatic tubing with the blood pump. This compactness attribute is particularly essential for implant devices. It not only simplifies surgical operation and mitigates peri-operative implantation risks, but also contributes to the reduction of post-operative morbidity associated with driveline infection.

In some blood pump embodiments, the feedthrough is integrated with a distal shell of the pump housing and the feedthrough has a first portion as an extension of the distal shell in which the pneumatic lumen, the tether and the electric wire of the driveline are coupled, and a second portion being interlocked with the first portion working as a bend relief of the driveline, to the advantage of anatomic adaptivity and fitness to the implant site geometry.

An embodiment of the present flow communication invention provides an aortic adapter assembly, for an implantable ventricular assist device, comprising: a T-shaped aortic adapter, including: an inserted conduit portion, an extruded neck portion, wherein the inserted conduit portion is joined with the extruded neck portion, both having a blood-contacting surface which is smooth; and a truss, disposed in the inserted conduit portion; wherein the T-shaped aortic adapter has a polymeric elastomer reinforced by the truss having a Nitinol material; wherein the inserted conduit portion has a wall which is gradually thinning at two conduit ends of the inserted conduit portion, with a proper distance of a tip of the conduit end to the outmost boundary of the truss, and the conduit end possesses a compliance-matching effect to an implant site artery; wherein a proximal end of the extruded neck portion is configured to be joined with an inlet adapter of a blood pump.

The embodiment of the present flow communication invention has at least one of the following advantages or effects. The present invention discloses a flow communicator assembly that enables blood flow transport into and out of a para-aortic ventricular assist device 10, in particular, a counterpulsatile blood pump. Unlike many existing flow communicators that employ rough surface approach to promote endothelialization so as to avert thrombotic adverse events to occur, the present aortic adapter invention adopts a smooth surface, insertion type prosthetic graft concept to construct the flow communicator. Further, a compliance-matching design is embodied around the inserted conduit ends, which combines the gradually thinning wall characteristic with a super-elastic Nitinol supported thin-walled polymer to accomplish the endo-leak free requirement. Abnormal high pressure, high shear, and low-speed recirculation flow phenomena associated with para-aortic counterpulsatile pumping are contained within the artificial surface of the inserted conduit. Hence, the pathologic device-induced hemodynamic influences and risk factors are substantially eliminated and long-term vascular maladaptation related adverse events such as endothelial cell erosion, lipid infiltration, smooth muscle cell proliferation, vascular stenosis, arterial wall dissection, etc. are significantly reduced. To accomplish a sound connection of the semi-rigid flow adapter to a blood pump, a quick connector type coupler is invented. This coupler has a self-alignment interface design that minimizes the step and gap discontinuity and hence reduces the possibility of thrombotic adverse events to occur at interface joint. Accompanying this aortic adapter invention is a specially designed delivery method that assures a quick and safe delivery procedure. The crimped aortic adapter is made into a prepack delivery configuration whose overall size is reduced into half of its deployed configuration. This prepacked adapter can be inserted into the implant site aorta easily and self-expands into its original deployed configuration, resulting in a snuggly fitted flow communicator without the concern of endo-leak. It is not only beneficial for surgical operations that mitigate peri-operative implantation risks, but also contributes to the reduction of post-operative morbidity associated with device-induced flow and implant site vascular maladaptation.

Use of ordinal terms such as “first”, “second”, “third”, etc., in the claims to modify a claim element does not by itself connote any priority, precedence, or order of one claim element over another or the temporal order in which acts of a method are performed, but are used merely as labels to distinguish one claim element having a certain name from another element having the same name (but for use of the ordinal term) to distinguish the claim elements.

Embodiments of this invention are described, and variations of those embodiments may become apparent to those of ordinary skill in the art upon reading the foregoing description. Accordingly, this invention includes all modifications and equivalents of the subject matter recited in the claims.

What is claimed is:

1. A para-aortic blood pump device, comprising:

a blood pump, comprising a pump housing, a blood sac, and a pressure sensor, the blood sac disposed in the pump housing, and the pressure sensor being installed in the pump housing for monitoring blood pressure inside the blood pump to generate an electrical blood pressure signal;

an aortic adapter, being a T-manifold shaped conduit, coupled to the blood pump, and provided for integrating the blood pump with human aorta;

a driveline, coupled to the pump housing of the blood pump, for transmitting the electrical blood pressure signal received from the pressure sensor;

a driver, coupled to the driveline for receiving the electrical blood pressure signal, and comprising an electro-mechanical actuator to generate a pressure pulse according to the electrical blood pressure signal, and providing the pressure pulse to the blood pump through the driveline;

a coupler for coupling the blood pump to the aortic adapter;

wherein the coupler comprises a flange base, a pair of collars, and a hinge assembly that join together the collars with the flange base.

2. The para-aortic blood pump device according to claim 1, wherein the driver further comprises a driveline controller and a vibrator, and the driveline controller is used for processing the electrical blood pressure signal, and the vibrator is used for providing an audible alarm or a tactile feedback.

3. The para-aortic blood pump device according to claim 1, wherein two gradually flared conduit ends of the aortic adapter constitute a smooth transition of an elastic property, being progressively softer in proportion to the wall thickness of the aortic adapter toward the conduit end.

4. The para-aortic blood pump device according to claim 1, wherein the pump housing of the blood pump is installed with the blood sac therein, and the blood sac is an oval-shaped membrane body of revolution to a centerline of the blood pump, at two ends there are two polymeric stems that are bonded with the blood sac, working as a flexing/stretching relief mechanism to alleviate stress concentration when attached onto the pump housing of the blood pump.

5. The para-aortic blood pump device according to claim 1, wherein the pump housing of the blood pump has an opening, and the opening continuously integrates with the aortic adapter that provides a smooth interface with a neck of the aortic adapter.

6. The para-aortic blood pump device according to claim 1, wherein the electro-mechanical actuator comprises a pressure equalization valve connected to a cylinder of the electro-mechanical actuator, and the pressure equalization valve is opened periodically so that an air pressure in the cylinder can be set to be in equilibrium with atmospheric pressure.

7. The para-aortic blood pump device according to claim 1, wherein the para-aortic blood pump device provides a counter-pulsatile augmentation of systemic blood flow during diastole (heart relaxation) to improve myocardial and organ perfusion while reducing left ventricular workload during systole (heart contraction).

8. The para-aortic blood pump device according to claim 1, wherein the driver further comprises a trigger-detection micro controller unit, and the electrical blood pressure signal provides the sensed pressure waveform within the blood pump for the trigger-detection micro controller unit to compute and determine the eject and fill timings for the electro-mechanical actuator.

9. The para-aortic blood pump device according to claim 1, wherein the electro-mechanical actuator comprises a motor and a ball screw unit that drives a reciprocating piston within a cylinder of the electro-mechanical actuator; the movement of the piston pushes and withdraws air via the driveline coupled to the blood pump.

10. The para-aortic blood pump device according to claim 1, wherein the electro-mechanical actuator is a pneumatic actuator includes:

a brushless servo motor, a ball screw unit, a piston and cylinder assembly, wherein atmospheric air is used as a driving medium to reciprocally eject and fill the blood pump; and a pressure equalization valve is equipped on the electro-mechanical actuator to solve the problems of air leakage at a piston ring of the piston cylinder assembly and condensation of vapor permeated out from a blood sac.

11. The para-aortic blood pump device according to claim 7, wherein the driver receives the electrical blood pressure signal and processes the electrical blood pressure signal using trigger detection algorithm to generate a trigger signal that commands a driver actuation in synchronization with the heart rhythm.

12. The para-aortic blood pump device according to claim 10, wherein, upon receiving the assigned trigger timing, the micro controller unit sends commands to a motor controller to drive a piston of the electro-mechanical actuator, from eject-to-fill or from fill-to-eject positions, to provide counter-pulsatile circulatory support including contraction unloading during the cardiac systolic phase and perfusion augmentation during the cardiac diastolic phase, respectively.

13. The para-aortic blood pump device according to claim 1, wherein the driver further comprises a user interface, and the user interface comprises an indicator, an audio alarm, a button and a liquid crystal display (LCD).

14. The para-aortic blood pump device according to claim 7, wherein, when the micro controller unit loses the electrical blood pressure signal from the blood pump, a washout mode is launched automatically by the micro controller unit to drive the electro-mechanical actuator, operating at a predetermined pumping rate and driver stroke volume.

15. The para-aortic blood pump device according to claim 12, wherein the washout mode is used to prevent the formation of thrombus in the blood pump, which is a device protection mode instead of providing circulatory support.

16. The para-aortic blood pump device according to claim 3, wherein the blood sac is anchored via a proximal stem to a proximal shell of the pump housing and via a distal stem to a distal shell of the pump housing.

* * * * *